(12) United States Patent
Bamdad

(10) Patent No.: US 8,344,113 B2
(45) Date of Patent: Jan. 1, 2013

(54) DIAGNOSTIC TUMOR MARKERS, DRUG SCREENING FOR TUMORIGENESIS INHIBITION, AND COMPOSITIONS AND METHODS FOR TREATMENT OF CANCER

(75) Inventor: Cynthia C. Bamdad, Boston, MA (US)

(73) Assignee: Minerva Biotechnologies Corporation, Waltham, MA (US)

(*) Notice: Subject to any disclaimer, the term of this patent is extended or adjusted under 35 U.S.C. 154(b) by 0 days.

(21) Appl. No.: 12/695,070

(22) Filed: Jan. 27, 2010

(65) Prior Publication Data

US 2010/0136017 A1   Jun. 3, 2010

Related U.S. Application Data

(63) Continuation of application No. 09/996,069, filed on Nov. 27, 2001, now Pat. No. 7,700,715.

(60) Provisional application No. 60/253,361, filed on Nov. 27, 2000, provisional application No. 60/255,370, filed on Dec. 13, 2000, provisional application No. 60/256,027, filed on Dec. 15, 2000, provisional application No. 60/258,157, filed on Dec. 22, 2000, provisional application No. 60/259,615, filed on Jan. 3, 2001, provisional application No. 60/260,186, filed on Jan. 5, 2001, provisional application No. 60/266,169, filed on Feb. 2, 2001, provisional application No. 60/289,444, filed on May 7, 2001, provisional application No. 60/266,929, filed on Feb. 6, 2001, provisional application No. 60/278,093, filed on Mar. 23, 2001, provisional application No. 60/294,887, filed on May 31, 2001, provisional application No. 60/298,272, filed on Jun. 14, 2001.

(51) Int. Cl.
C07K 16/00 (2006.01)

(52) U.S. Cl. ............. 530/388.22; 530/350; 530/387.1; 530/387.9; 530/388.8; 530/389.1; 530/389.7

(58) Field of Classification Search .............. 530/350, 530/387.1, 387.7, 387.9, 388.22, 388.8, 389.1, 530/389.7
See application file for complete search history.

(56) References Cited

U.S. PATENT DOCUMENTS

| | | | |
|---|---|---|---|
| 3,854,480 A | 12/1974 | Zaffaroni | |
| 4,452,775 A | 6/1984 | Kent | |
| 4,675,189 A | 6/1987 | Kent et al. | |
| 5,075,109 A | 12/1991 | Tice et al. | |
| 5,108,933 A | 4/1992 | Liberti et al. | |
| 5,133,974 A | 7/1992 | Paradissis et al. | |
| 5,407,686 A | 4/1995 | Patel et al. | |
| 5,736,152 A | 4/1998 | Dunn | |
| 6,127,393 A | 10/2000 | Fernandez-Pol | |
| 6,548,643 B1 * | 4/2003 | McKenzie et al. | 530/395 |
| 2002/0156112 A1 | 10/2002 | Bamdad et al. | |
| 2003/0036199 A1 | 2/2003 | Bamdad et al. | |
| 2003/0119834 A1 | 6/2003 | Bamdad | |
| 2003/0130293 A1 | 7/2003 | Bamdad | |
| 2005/0019324 A1 | 1/2005 | Wreschner et al. | |

FOREIGN PATENT DOCUMENTS

| | | |
|---|---|---|
| EP | 0 369 816 A2 | 5/1990 |
| WO | WO 92/07000 | 4/1992 |
| WO | WO 95/24929 | 9/1995 |
| WO | WO 96/03502 A2 | 2/1996 |
| WO | WO 00/34783 | 6/2000 |
| WO | WO 00/43783 | 7/2000 |
| WO | WO 00/43791 | 7/2000 |
| WO | WO 01/34145 A1 | 5/2001 |
| WO | WO 02/22685 A2 | 3/2002 |
| WO | WO 03/020279 A2 | 3/2002 |
| WO | WO 02/056022 A2 | 7/2002 |
| WO | WO 02/078598 A2 | 10/2002 |
| WO | WO 03/020280 A2 | 3/2003 |
| WO | WO 03/089451 A2 | 3/2003 |
| WO | WO 03/054154 A2 | 7/2003 |
| WO | WO 2004/005470 A2 | 1/2004 |
| WO | WO 2005/019269 A2 | 3/2005 |

OTHER PUBLICATIONS

Pemberton et al. (Biochem. Biophys. Res. Commun. 1992; 185 (1): 167-175).*
Kufe et al. (Hybridoma. 1984 Fall; 3 (3): 223-232).*
Baldus et al. (Int. J. Cancer. Apr. 17, 1998; 79 (2): 133-138).*
Blockzjil et al. (Tumour Biol. 1998; 19 (Suppl. 1): 46-56).*
Byrd et al. (Biochem. J. Jul. 15, 1989; 261 (2): 617-25).*
Baeckstrom et al. (J. Biol. Chem. Nov. 15, 1991; 266 (32): 21537-47).*
Yonezawa et al. (Biochem. J. Jun. 15, 1991; 276 (Pt. 3): 599-605).*
Gendler et al. (J. Biol. Chem. Sep. 5, 1990; 265 (25): 15286-93).*
Devine et al. (Dis. Markers. Oct. 1998; 14 (2): 99-112).*
Sojar et al. (Arch. Biochem. Biophys. Nov. 15, 1987; 259 (1): 52-7).*
Muller et al. (J. Biol. Chem. Oct. 3, 1997; 272 (40): 24780-93).*
Mahanta et al. (PLoS One. Apr. 30, 2008; 3 (4): e2054; pp. 1-12).*
Girling et al., "A Core Protein Epitope of the Polymorphic Epithelial Mucin Detected by The Monoclonal Antibody SM-3 is Selectively Exposed in a Range of Primary Carcinomas." International Journal of Cancer, 43(6):1072-1076, 1989.
U.S. Appl. No. 09/631,818, filed Aug. 3, 2000, Bamdad.
Meerzaman, et al., "Involvement of the MAP kinase ERK2 in MUC1 mucin signalin", Am. J. Physiol. Lung Cell Mol. Physiol. (2001), 281: L86-L91.
Spicer, et al., "Molecular Cloning and Analysis of the Mouse Homologue of the Tumor-associated Mucin, MUC1, Reveals Conservation of Potential O-Glycosylation Sites, Transmembrane, and Cytoplasmic Domains and a Loss of Minisatellite-like Polymorphism", The Journal of Biological Chemistry (1991), 266(23): 15099-15109.
Varner, et al., "Integrins and cancer", Current Opinion in Cell Biology (1998), 8: 724-730.
Horton, The avb3 Integrin "Vitronectin Receptor", Int. J. Biochem. Cell Biol. (1997), 29(5), 721-725.
Ross, et al., "The HER-2/neu Oncogene in breast Cancer: Prognostic Factor, Predictive Factor, and Target for Therapy", Stem Cells (1998), 16: 413-428.

(Continued)

Primary Examiner — Stephen Rawlings
(74) Attorney, Agent, or Firm — Joseph Hyosuk Kim; JHK Law

(57) ABSTRACT

The invention provides a series of compositions, methods, kits, articles and species associated primarily with the diagnosis and/or treatment of cell proliferation, specifically cancer. Cell proliferation associated with aberrant expression of MUC1 is particularly focused upon. Mechanisms associated with MUC1 cell proliferation are discussed.

13 Claims, 23 Drawing Sheets

OTHER PUBLICATIONS

Treon, et el., "MUC-1 Core Protein is Expressed on Multiple Myeloma Cells and is Induced by Dexamethasone", Blood (1999), 93(4): 1287-1298.

Ligtenberg, et al., "Cell-associated Episialin is a Complex Containing Two Proteins Derived from a Common Precursor", The Journal of Biological Chemistry (1992), 267(9) 6171-6177.

Chen, et al., "Labeling of Proteins with [35S]Methionine and/or [35S]Cysteine in the Absence of Cells", Analytical Biochemistry (1999), 269: 179-188.

Sawhney, et al., "Bioerodible Hydrogeis Based on Photopolymerized Poly(ethylene glycol)-co-poly(a-hydroxy acid) Diacrylate Macromers", Macromolecules (1993), 26: 581-587.

Hieken, et al., "beta3 Integrin Expression in Melanoma Predicts Subsequent Metastasis", Journal of Surgical Research (1996): 63(1): 169-173(5).

Vailhe, et al., "In vitro angiogenesis is modulated by the mechanical properties of fibrin gels and is related to alpha(v)befa3 integrin loctization", In Vitro Cell Dev. Biol. Anim. (1997), 33(10): 753-773.

Pegram, et al., "Phase II study of receptor-enhanced chemosensitivity using recombinant humanized anti-p185HER2/neu monolonal antibody plus cisplatin in patients with HER2/neu-overexpressing metastic breast cancer refractory to chemotherapy treatment", Journal of Clinical Oncology (1996), 16: 2659-2671.

Fraley, et al., "New generation liposomes: the engineering of an efficient vehicle for intracellular delivery of nucleic acids", Trends in Biochemical Sciences(1981), 6: 77-80.

Kufe, et al., "Differential reactivity of a novel monoclonal antibody (DF3) with human malignant versus benign breast tumors", Hybridoma (1984), 3(3): 223-232.

Schneider, et al., "nm23 expression in advanced and borderiine ovarian carcinoma", Anticancer Res. (1996), 16 (3A): 1197-1202.

Mao, et al., "Loss nm23 expression predicts distal metastases and poorer suivival for breast cancer", Int. J. Oncol. (2001), 18(3): 587-591.

Gregoriadis, "Liposomes for drugs and vaccines", Trends in Biotechnology (1985), 3(9): 235-241.

Hartman, et al., "Muc1 isoform specific monoclonal antibody 6E6/2 detects preferential expression of the novel Muc1/Y protein in breast and ovarian cancer," Int. J. Cancer, 82:256-267, 1999.

Skolnick, et al., "From genes to protein structure and function novel applications of computational approaches in the genomic era," Trends in Biotechnology, 18(1):34-39, 2000.

Burgess, et al. "Possible Dissociation of the Heparin-binding and Mitogenic Activities of Heparin-Binding (Acidic Fibroblast) Growth Factor-1 from its Receptor-binding Activities by Site-directed Mutagenesis of a Single Lysine Residue," J Cell Biol, 111:2129-2138, 1990.

Lazar, et al., "Transforming Growth Factor alpha: Mutation of Aspartic Acid 47 and Leucine 48 Results in Different Biological Activities," Mol Cell Biol, 8(3): 1247-1252, 1988.

Lan, M.S., et al., "Cloning and Sequencing of a Human Pancreatic Tumor Mucin cDNA," J Biol Chem, 265(25):15294-15299, 1990.

ImmunoGlob GmbH website (pp.1-3; Sep. 14, 2011).

* cited by examiner

DIAGNOSTIC TUMOR MARKERS, DRUG SCREENING FOR TUMORIGENESIS INHIBITION, AND COMPOSITIONS AND METHODS FOR TREATMENT OF CANCER

CROSS-REFERENCE TO RELATED APPLICATIONS

The present application is a continuation application of U.S. patent application Ser. No. 09/996,069, filed Nov. 27, 2001 (now U.S. Pat. No. 7,700,715), which claims the benefit of priority to U.S. provisional application No. 60/253,361, filed Nov. 27, 2000, U.S. provisional application No. 60/255, 370, filed Dec. 13, 2000, U.S. provisional application No. 60/256,027, filed Dec. 15, 2000, U.S. provisional application No. 60/258,157, filed Dec. 22, 2000, U.S. provisional application No. 60/259,615, filed Jan. 3, 2001, U.S. provisional application No. 60/260,186, filed Jan. 5, 2001, U.S. provisional application No. 60/266,169, filed Feb. 2, 2001, U.S. provisional application No. 60/289,444, filed May 7, 2001, U.S. provisional application no. 60/266,929, filed Feb. 6, 2001, U.S. provisional application No. 60/278,093, filed Mar. 23, 2001, U.S. provisional application No. 60/294,887, filed May 31, 2001, and U.S. provisional application No. 60/298, 272, filed Jun. 14, 2001, the contents of which are incorporated by reference herein in its entirety.

FIELD OF THE INVENTION

The invention relates to assays using shed cell surface receptor interchain binding regions and cleavage products for cancer diagnosis, and for the evaluation of cancer treatment and using the portion of the receptor that remains on the cell as a molecular target for cancer therapeutics.

BACKGROUND OF THE INVENTION

Many of the biomolecular interactions that promote tumorigenesis involve cell surface proteins that mediate both intra- and intercellular signaling. "Tumor markers" are proteins on the surface of a cell that are exclusively expressed, over-expressed or show an altered expression pattern as a result of transformation to a neoplastic state. The surface concentration of certain tumor markers has been correlated to the progression of cancer. For example, the interaction between the cell surface receptor $\alpha V\beta 3$ and the cell adhesion molecule vitronectin has been implicated in angiogenesis (Varner J, Cheresh D: Integrins and cancer. *Curr Opin Cell Biol,* 1996, 8(5): 724-730; Vailhe B, Ronot X, Tracqui P, Usson Y, Tracqui L: In vitro angiogenesis is modulated by the mechanical properties of fibrin gels and is related to $\alpha V\beta 3$ integrin localization. *In Vitro Cell Dev Biol Anim,* 1997, 33(10): 763-773; Horton M: The ab$\beta 3$ integrin "vitronectin receptor". *Int J Biochem Cell Biol,* 1997, 29(5): 721-725) and the increased concentration of $\alpha V\beta 3$ on melanoma cells has been correlated with poor prognosis (Hieken T, Farolan M, Ronan S, Shilkaitis A, Wild L, Das Gupta T: $\beta 3$ integrin expression in melanoma predicts subsequent metastasis. *J Surg Res,* 1996, 63(1): 169-173).

Cell surface receptors, that have been linked to cancer, make up an important class of therapeutic targets. Many pharmaceutical companies are actively involved in screening drug libraries for compounds that bind to and block these cell surface receptors. For example, an important drug used to treat breast cancer is Herceptin (Pegram M, Lipton A, Hayes D, Webber B, Baselga J, Tripathy D, Baly D, Baughman S, Twaddell T, Glaspy J, Slamon D: Phase II study of receptor-enhanced chemosensitivity using recombinant humanized anti-p185 Her2/neu monoclonal antibody plus cisplatin, in patients with Her2/neu-overexpressing metastatic breast cancer refractory to chemotherapy treatment, *J Clin Oncol,* 1998, 16(8): 2659-2671). This drug binds to and blocks HER2/neu (Ross J, Fletcher J: review, The Her2/neu oncogene in breast cancer: prognostic factor, predictive factor, and target for therapy. *Stem Cells,* 1998, 16(6): 413-428) which is a cell surface receptor that is over-expressed on 30% of breast tumors.

Another cell surface receptor, called MUC1 (Treon S, Mollick J, Urashima M, Teoh G, Chauhan D, Ogata A, Raje N, Hilgers J, Nadler L, Belch A, Pilarski L and Anderson K: MUC1 core protein is expressed on multiple myeloma cells and is induced by dexamethasone. *Blood,* 1999, 93(4): 1287-1298), is especially interesting since it is aberrantly expressed on many human tumors, including 80% of breast tumors, and on a significant percentage of prostate, lung, ovarian, colorectal and perhaps brain, cancers. On healthy secretory epithelium, MUC1 is clustered at the apical border and is not expressed over other portions of the cell. However, in tumor cells, the receptor is homogeneously over-expressed over the entire cell surface (Kufe D., Inghirami G., Abe M., Hayes D, Justi-Wheeler H, Schlom J: Differential reactivity of a novel monoclonal antibody (DF3) with human malignant versus benign breast tumors. *Hybridoma,* 1984, 3: 223-232), rather than just at the apical border. It is also known that women with breast cancer have elevated levels of shed MUC1 receptor in their blood stream. Extracellular portions of the MUC1 receptor are cleaved or "shed", by at least one enzyme, and released into the blood stream. Levels of shed MUC1 receptor in serum are measured to track breast cancer patients for recurrence. However, the method is too variable and insensitive to be used as a general diagnostic.

Until now, the mechanistic link between the MUC1 receptor and tumorigenesis has not been understood. Attempts to correlate the number of repeat units, which varies from person to person, and susceptibility to cancer failed. Investigations of a possible connection, between glycosylation of the MUC1 receptor and cancer, produced conflicting results. Importantly, until now, a functional ligand(s) for the extracellular portion of the MUC1 receptor has not been identified.

Absent an understanding of the mechanism of the MUC1 receptor, and how it triggers tumorigenesis, it has not been possible to design or identify therapeutics that interfere with the disease-associated function of this receptor. Indeed, currently there is no drug in use or, to our knowledge, in clinical trials that is known to target the MUC1 receptor.

The present invention describes discoveries that elucidate critical aspects of the mechanism by which MUC1 triggers cell proliferation and tumorigenesis. These discoveries provide novel molecular targets for drug screening assays which the inventors have used to identify compounds that inhibit the MUC1-dependent tumorigenesis. These discoveries also enable an early diagnostic assay.

SUMMARY OF THE INVENTION

The present invention provides a variety of kits, methods, compositions, peptide species and articles associated with cell proliferation, specifically cancer. The invention involves primarily techniques and components for the diagnosis and treatment of cancer.

In one aspect, the invention provides a series of kits. One kit includes a first article having a surface, and a peptide sequence immobilized relative to or adapted to be immobilized relative to the surface. The peptide sequence includes a portion of a cell surface receptor that interacts with an activating ligand such as a growth factor to promote cell proliferation. Also included in the kit is a candidate drug for affecting the ability of the peptide sequence to bind to other identical peptide sequences in the presence of the activating ligand. The portion includes enough of the cell surface receptor to interact with the activating ligand and the portion is free of interchain binding region to the extent necessary to prevent spontaneous binding between the portions.

Another kit of the invention comprises a species able to become immobilized relative to a shed cell surface receptor interchain binding region, and a signaling entity immobilized relative to or adapted to be immobilized relative to the species.

Another kit of the invention comprises a species able to bind to a portion of a cell surface receptor that remains attached to the cell surface after shedding of a cell surface receptor interchain binding region, and a signaling entity immobilized relative to or adapted to be immobilized relative to the species.

Another kit of the invention comprises a species able to bind to a portion of a cell surface receptor that includes the interchain binding region, and a signaling entity immobilized relative to or adapted to be immobilized relative to the species.

Another kit of the invention comprises an article (which can be a particle), and at least a fragment of the sequence that corresponds to that portion of a cell surface receptor that interacts with an activating ligand such as a growth factor to promote cell proliferation, the fragment being detached from any cell, fastened to or adapted to be fastened to the article.

Another kit of the invention comprises an article having a surface, and a biomolecule that binds to a portion of a cell surface receptor that interacts with an activating ligand such as a growth factor to promote cell proliferation. The biomolecule is fastened to or adapted to be fastened to the surface of the article.

In another aspect, the invention provides a series of methods. One method comprises providing a peptide including a portion of a cell surface receptor that interacts with an activating ligand such as a growth factor to promote cell proliferation, exposing the peptide to a candidate drug for affecting the ability of the activating ligand to interact with the peptide, and to the activating ligand, and determining the ability of the candidate drug to prevent interaction of the activating ligand with the peptide. The portion includes enough of the cell surface receptor to interact with the activating ligand and the portion is free of interchain binding region to the extent necessary to prevent spontaneous binding between portions.

Another method of the invention involves treating a subject having cancer or being at risk for developing cancer, the method comprises administering to the subject an agent that reduces cleavage of a cell surface receptor.

Another method of the invention for treating a subject having cancer or at risk for developing cancer comprises administering to the subject an agent that reduces cleavage of a cell surface receptor interchain binding region from the cell surface.

Another method of the invention comprises determining an amount of cleavage of a cell surface receptor interchain binding region from a cell surface, and evaluating indication of cancer or potential for cancer based upon the determining step.

Another method of the invention comprises determining a site of cleavage of a cell surface receptor in a sample from a subject, and evaluating an indication of cancer or potential for cancer based upon the determining step.

Another method of the invention involves determining a cleavage site of a cell surface. The method comprises contacting a cell with an agent that binds specifically to one potential cell surface receptor cleavage site and another agent that binds specifically to another potential cell surface receptor cleavage site. The ratio of binding of the two agents to the cell surface is compared in the method.

Another method of the invention comprises determining a first amount of cleavage of a cell surface receptor interchain binding region from a cell surface of a sample from a subject. A second amount of cleavage of cell surface receptor interchain binding region from a cell surface of a sample from the subject is also determined, and the first amount is compared to the second amount.

Another method of the invention involves treating a subject to reduce the risk of or progression of cancer. The method comprises administering to a subject, who is known to be at risk for cancer or is diagnosed with cancer, an agent for inhibiting interaction of an activating ligand with a portion of a cell surface receptor that interacts with the activating ligand to promote cell proliferation.

Another method of the invention involves treating a subject to reduce the risk of or progression of cancer. The method comprises administering to a subject, who is known to be at risk of cancer or is diagnosed with cancer, an agent for preventing clustering of portions of cell surface receptors that interact with an activating ligand such as a growth factor to promote cell proliferation.

Another method of the invention comprises exposing a ligand capable of binding with a portion of a cell surface receptor that remains attached to the cell after shedding of the cell surface receptor interchain binding region, and an agent capable of blocking this binding, to a candidate drug for disruption of interaction between the ligand and the agent. Disruption of the interaction by the candidate drug is determined.

Another method of the invention comprises exposing a portion of a cell surface receptor that remains attached to the cell surface after shedding of a cell surface receptor interchain binding region which is capable of binding with a ligand, and an agent capable of blocking this binding, to a candidate drug for disruption of interaction between the portion and the agent, and determining disruption of the interaction by the candidate drug.

Another method of the invention comprises exposing a synthetic drug, and a biological target of the synthetic drug, to a candidate drug which may interact with a biological target to a degree greater than the interaction between the synthetic drug and the target, and determining disruption of the interaction by the candidate drug.

Another method involves diagnosing a physiological state indicative of cancer or potential for cancer. The method comprises determining a specific cleavage site of MUC1 distinguishable from a different cleavage state of MUC1.

Another method of the invention involves treating a subject having a cancer characterized by the aberrant expression of MUC1, comprising administering to the subject etomoxir in an amount effective to reduce tumor growth.

Another method of the invention involves treating a subject having a cancer characterized by the aberrant expression of MUC1, comprising administering to the subject L-α-methyldopa in an amount effective to reduce tumor growth.

Another method of the invention for treating a subject having cancer characterized by the aberrant expression of MUC1, comprises administering to the subject calcimycin in an amount effective to reduce tumor growth.

Another method for treating a subject having a cancer characterized by the aberrant expression of MUC1, comprises administering to the subject butylindazole in an amount effective to reduce tumor growth.

In another aspect, the invention provides compositions. One composition of the invention comprises at least a portion of a shed cell surface receptor interchain binding region, and a signaling entity immobilized relative to or adapted to be immobilized relative to the portion.

The invention also provides peptide species. One peptide species of the invention comprises at least a fragment of a sequence that corresponds to that portion of a cell surface receptor that interacts with an activating ligand such as a growth factor to promote cell proliferation, the portion being detached from any cell, and an affinity tag.

In one aspect, the invention is directed to a method of treating a subject to reduce the risk of or progression of cancer comprising: administering to a subject who is known to be at risk for cancer or is diagnosed with cancer an agent for inhibiting interaction of an activating ligand with a portion of a cell surface receptor that interacts with the activating ligand to promote cell proliferation, wherein the portion of the cell surface comprises at least 12 contiguous amino acids from the sequence GTINVHDVETQFNQYKTEAASPYNLTIS-DVSVSDVPFPFSAQSGA (SEQ ID NO: 7). In another aspect, the invention is directed to a method of treating a subject to reduce the risk of or progression of cancer comprising: administering to a subject who is known to be at risk for cancer or is diagnosed with cancer an agent for inhibiting interaction of an activating ligand with a portion of a cell surface receptor that interacts with the activating ligand to promote cell proliferation, wherein the portion of the cell surface receptor that remains attached to the cell surface after shedding of the cell surface receptor interchain binding region comprises at least 12 contiguous amino acids from the peptide sequence GTINVHDVETQFNQYKTEAASPYN-LTISDVSVS (SEQ ID NO:6).

In one aspect, the invention is directed to a method of treating a subject to reduce the risk or of progression of cancer comprising: administering to a subject who is known to be at risk of cancer or is diagnosed with cancer, an agent for preventative clustering of portions of cell surface receptors that interact with an activating ligand such as a growth factor to promote cell proliferation, wherein the portion of the cell surface receptor comprises at least 12 contiguous amino acids from the peptide sequence GTINVHDVETQFNQYK-TEAASPYNLTISDVSVSDVPFPFSAQSGA (SEQ ID NO: 7).

DETAILED DESCRIPTION OF THE INVENTION

Definitions

Figure 1:
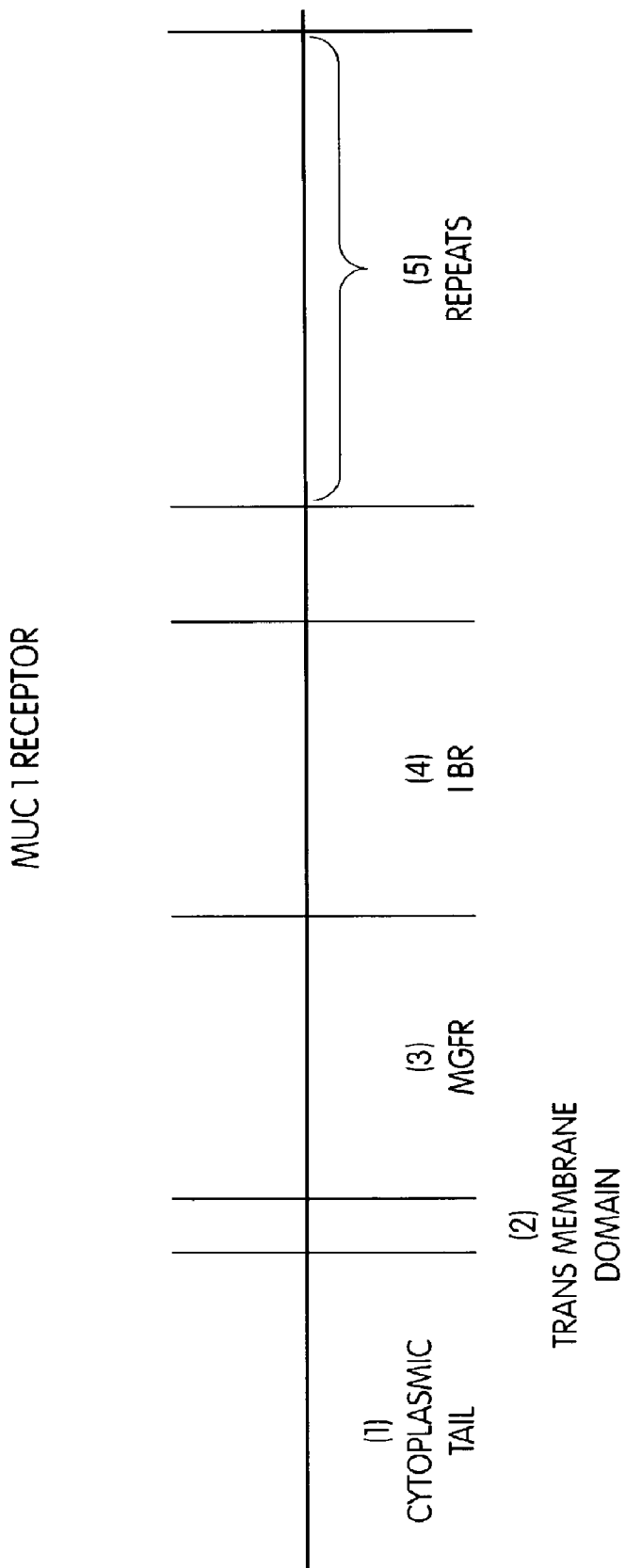
FIG. 1 is a schematic illustration of the MUC1 receptor.

The term "MUC1 Growth Factor Receptor" (MGFR) is a functional definition meaning that portion of the MUC1 receptor that interacts with an activating ligand, such as a growth factor, to promote cell proliferation. The MGFR region of MUC1 is that portion that is closest to the cell surface and is defined by most or all of the PSMGFR. The MGFR is inclusive of both unmodified peptides and peptides that have undergone enzyme modifications, such as, for example, phosphorylation, glycosylation, etc. Results of the invention are consistent with a mechanism in which this portion is made accessible to the ligand upon MUC1 cleavage at a site associated with tumorigenesis that causes release of the IBR from the cell.

The term "Interchain Binding Region" (IBR) is a functional definition meaning that portion of the MUC1 receptor that binds strongly to identical regions of other MUC 1 molecules giving MUC1 the ability to aggregate (i.e. self-aggregate) with other MUC1 receptors via the IBRs of the respective receptors. This self-aggregation may contribute to MUC1 receptor clustering, observed in healthy cells.

In a preferred embodiment, the IBR may be approximately defined as a stretch of at least 12 to 18 amino acid sequence within the region of the human MUC1 receptor defined as comprising amino acids 507 to 549 of the extracellular sequence of the MUC1 receptor, with amino acids 525 through 540 and 525 through 549 especially preferred (numbers refer to Andrew Spicer et al., J. Biol. Chem Vol 266 No. 23, 1991 pgs. 15099-15109; these amino acid numbers correspond to numbers 1067, 1109, 1085, 1100, 1085, 1109 of GENBANK® accession number P15941; PID G547937, SEQ ID NO: 10) or fragments, functional variants or conservative substitutions thereof.

The term "cleaved IBR" means the IBR (or a portion thereof) that has been released from the receptor molecule segment which remains attached to the cell surface. The release may be due to enzymatic or other cleavage of the IBR. As used herein, when the IBR is "at the surface of a cell", it means the IBR is attached to the portion of the cell surface receptor that has not been shed, or cleaved. The cleaved IBR of interest is a "disease-associated cleavage", i.e. that type of cleavage that can result in cancer.

The term "Constant Region" (CR) is any non-repeating sequence of MUC1 that exists in a 1:1 ratio with the IBR and forms part of the portion of MUC1 that is shed upon cleavage in healthy and tumorigenesic cells.

The term "Repeats" is given its normal meaning in the art.

The term "Primary Sequence of the MUC1 Growth Factor Receptor" (PSMGFR) is a peptide sequence, defined below (See Table 1—SEQ ID NO: 7), that defines most or all of the MGFR. The PSMGFR is inclusive of both unmodified peptides and peptides that have undergone enzyme modifications, such as, for example, phosphorylation, glycosylation, etc. The histidine-tagged PSMGFR (See Table 1—SEQ ID NO: 2) is abbreviated herein as His-PSMGFR.

The term "Extended Sequence of the MUC1 Growth Factor Receptor" (ESMGFR) is a peptide sequence, defined below (See Table 1—SEQ ID NO: 3), that defines all of His-PSMGFR plus 9 amino acids of the proximal end of PSIBR.

PSIBR is a peptide sequence, defined below (See Table 1—SEQ ID NO: 8), that defines most or all of the IBR.

The term "separation" means physical separation from a cell, i.e. a situation in which a portion of MUC 1 that was immobilized with respect to a cell is no longer immobilized with respect to that cell. E.g. in the case of cleavage of a portion of MUC1, the portion that is cleaved is "separated" if it is free to migrate away from the cell and thereafter may be detected in a bodily fluid, or immobilized at a location remote from the cell from which it was cleaved such as another cell, a lymph node, etc.

The term "binding" refers to the interaction between a corresponding pair of molecules that exhibit mutual affinity or binding capacity, typically specific or non-specific binding or interaction, including biochemical, physiological, and/or pharmaceutical interactions. Biological binding defines a type of interaction that occurs between pairs of molecules including proteins, nucleic acids, glycoproteins, carbohydrates, hormones and the like. Specific examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc.

The term "binding partner" refers to a molecule that can undergo binding with a particular molecule. Biological binding partners are examples. For example, Protein A is a binding partner of the biological molecule IgG, and vice versa.

The term "aggregate" (noun) means a plurality of cell surface receptors or fragments thereof (e.g. MUC 1) immobilized with respect to each other with or without an intermediate auxialliary to the host system. This includes self-aggregation of healthy receptors at a cell surface; self-aggregation of cleaved receptors or fragments bound to each other; cleaved receptors or fragments bound to receptors or fragments attached to a cell surface; receptors or fragments, whether attached to a cell or cleaved, immobilized with respect to each other via an intermediate auxialliary to the host. "Intermediate auxialliary to the host system" includes a synthetic species such as a polymer, dendrimer, etc., or a naturally-occurring species, for example an IgM antibody, which is not simply naturally present in the host system but is added to the host system from a source external to the host system. This excludes aggregation that is the result of an intermediate naturally present in the host system such as a growth factor that can cause disease-associated aggregation ("Inductive multimerization"). "Aggregate" (verb) or "aggregation" means the process of forming an aggregate (noun).

"Inductive multimerization" refers to aggregation wherein the aggregate formed can act to induce the cells to grow or proliferate. Inductive multimerization typically involves dimerization or tetramerization of cell surface receptors, for example by a growth factor or other activating ligand, but can also involve higher order multimerization, so long as the degree of multimerization is not so great as to mimic natural receptor clustering, in a particular cell type, which prevents receptors from signalling the cell to grow or proliferate.

"Preventative clustering" refers to multimerization of receptors to form an aggregate involving a sufficient number of receptors to mimic natural receptor clustering, in a particular cell type, which prevents receptors from signalling the cell to grow or proliferate, for example with an intermediate auxialliary to the host system.

A "ligand" to a cell surface receptor, refers to any substance that can interact with the receptor to temporarily or permanently alter its structure and/or function. Examples include, but are not limited to binding partners of the receptor and agents able to alter the chemical structure of the receptor (e.g. modifying enzymes).

An "activating ligand" refers to a ligand able to effect inductive multimerization of cell surface receptors. Activating ligands can include, but are not limited to, a single molecular species with greater than one active site able to bind to a receptor; a dimer, a tetramer, a higher multimer, or a complex comprising a plurality of molecular species. In the context of MUC1 tumor cells, an activating ligand can be a species produced by the cells that interacts with the MGFRs on the surface of the MUC1 tumor cells in a manner that effects inductive multimerization.

A "growth factor" refers to a species that may or may not fall into a class of previously-identified growth factors, but which acts as a growth factor in that it acts as an activating ligand.

A "MUC1 presenting cell" refers to both non-cancerous and cancerous cells expressing MUC1 and/or MGFRs on the surface. A "MUC1 tumor cell" or "MUC1 cancer cell" or "cancerous MUC1 cell" refers to a cancerous tumor cell that aberrantly expresses MUC1 and/or MGFR on its surface.

"Colloids", as used herein, means nanoparticles, i.e. very small, self-suspendable or fluid-suspendable particles including those made of material that is, e.g., inorganic or organic, polymeric, ceramic, semiconductor, metallic (e.g. gold), non-metallic, crystalline, amorphous, or a combination. Typically, colloid particles used in accordance with the invention are of less than 250 nm cross section in any dimension, more typically less than 100 nm cross section in any dimension, and in most cases are of about 2-30 nm cross section. One class of colloids suitable for use in the invention is 10-30 nm in cross section, and another about 2-10 nm in cross section. As used herein this term includes the definition commonly used in the field of biochemistry.

As used herein, a component that is "immobilized relative to" another component either is fastened to the other component or is indirectly fastened to the other component, e.g., by being fastened to a third component to which the other component also is fastened, or otherwise is transitionally associated with the other component. For example, a signaling entity is immobilized with respect to a binding species if the signaling entity is fastened to the binding species, is fastened to a colloid particle to which the binding species is fastened, is fastened to a dendrimer or polymer to which the binding species is fastened, etc. A colloid particle is immobilized relative to another colloid particle if a species fastened to the surface of the first colloid particle attaches to an entity, and a species on the surface of the second colloid particle attaches to the same entity, where the entity can be a single entity, a complex entity of multiple species, a cell, another particle, etc.

"Signaling entity" means an entity that is capable of indicating its existence in a particular sample or at a particular location. Signaling entities of the invention can be those that are identifiable by the unaided human eye, those that may be invisible in isolation but may be detectable by the unaided human eye if in sufficient quantity (e.g., colloid particles), entities that absorb or emit electromagnetic radiation at a level or within a wavelength range such that they can be readily detected visibly (unaided or with a microscope including an electron microscope or the like), or spectroscopically, entities that can be detected electronically or electrochemically, such as redox-active molecules exhibiting a characteristic oxidation/reduction pattern upon exposure to appropriate activation energy ("electronic signaling entities"), or the like. Examples include dyes, pigments, electroactive molecules such as redox-active molecules, fluorescent moieties (including, by definition, phosphorescent moieties), up-regulating phosphors, chemiluminescent entities, electrochemiluminescent entities, or enzyme-linked signaling moieties including horseradish peroxidase and alkaline phosphatase. "Precursors of signaling entities" are entities that by themselves may not have signaling capability but, upon chemical, electrochemical, electrical, magnetic, or physical interaction with another species, become signaling entities. An example includes a chromophore having the ability to emit radiation within a particular, detectable wavelength only upon chemical interaction with another molecule. Precursors of signaling entities are distinguishable from, but are included within the definition of, "signaling entities" as used herein.

As used herein, "fastened to or adapted to be fastened", in the context of a species relative to another species or to a surface of an article, means that the species is chemically or biochemically linked via covalent attachment, attachment via specific biological binding (e.g., biotin/streptavidin), coordinative bonding such as chelate/metal binding, or the like. For example, "fastened" in this context includes multiple chemical linkages, multiple chemical/biological linkages, etc., including, but not limited to, a binding species such as a peptide synthesized on a polystyrene bead, a binding species specifically biologically coupled to an antibody which is bound to a protein such as protein A, which is attached to a bead, a binding species that forms a part (via genetic engineering) of a molecule such as GST or Phage, which in turn is specifically biologically bound to a binding partner covalently fastened to a surface (e.g., glutathione in the case of GST), etc. As another example, a moiety covalently linked to a thiol is adapted to be fastened to a gold surface since thiols bind gold covalently. Similarly, a species carrying a metal binding tag is adapted to be fastened to a surface that carries a molecule covalently attached to the surface (such as thiol/gold binding) which molecule also presents a chelate coordinating a metal. A species also is adapted to be fastened to a surface if a surface carries a particular nucleotide sequence, and the species includes a complementary nucleotide sequence.

"Covalently fastened" means fastened via nothing other than one or more covalent bonds. E.g. a species that is covalently coupled, via EDC/NHS chemistry, to a carboxylate-presenting alkyl thiol which is in turn fastened to a gold surface, is covalently fastened to that surface.

"Specifically fastened" or "adapted to be specifically fastened" means a species is chemically or biochemically linked to another specimen or to a surface as described above with respect to the definition of "fastened to or adapted to be fastened", but excluding all non-specific binding.

Certain embodiments of the invention make use of self-assembled monolayers (SAMs) on surfaces, such as surfaces of colloid particles, and articles such as colloid particles having surfaces coated with SAMs. In one set of preferred embodiments, SAMs formed completely of synthetic molecules completely cover a surface or a region of a surface, e.g. completely cover the surface of a colloid particle. "Synthetic molecule", in this context, means a molecule that is not naturally occurring, rather, one synthesized under the direction of human or human-created or human-directed control. "Completely cover" in this context, means that there is no portion of the surface or region that directly contacts a protein, antibody, or other species that prevents complete, direct coverage with the SAM. I.e. in preferred embodiments the surface or region includes, across its entirety, a SAM consisting completely of non-naturally-occurring molecules (i.e. synthetic molecules). The SAM can be made up completely of SAM-forming species that form close-packed SAMs at surfaces, or these species in combination with molecular wires or other species able to promote electronic communication through the SAM (including defect-promoting species able to participate in a SAM), or other species able to participate in a SAM, and any combination of these. Preferably, all of the species that participate in the SAM include a functionality that binds, optionally covalently, to the surface, such as a thiol which will bind to a gold surface covalently. A self-assembled monolayer on a surface, in accordance with the invention, can be comprised of a mixture of species (e.g. thiol species when gold is the surface) that can present (expose) essentially any chemical or biological functionality. For example, they can include tri-ethylene glycol-terminated species (e.g. tri-ethylene glycol-terminated thiols) to resist non-specific adsorption, and other species (e.g. thiols) terminating in a binding partner of an affinity tag, e.g. terminating in a chelate that can coordinate a metal such as nitrilotriacetic acid which, when in complex with nickel atoms, captures a metal binding tagged-species such as a histidine-tagged binding species. The present invention provides a method for rigorously controlling the concentration of essentially any chemical or biological species presented on a colloid surface or any other surface. Without this rigorous control over peptide density on each colloid particle, co-immobilized peptides would readily aggregate with each other to form micro-hydrophobic-domains that would catalyze colloid-colloid aggregation in the absence of aggregate-forming species present in a sample. This is an advantage of the present invention, over existing colloid agglutination assays. In many embodiments of the invention the self-assembled monolayer is formed on gold colloid particles.

The kits described herein, contain one or more containers, which can contain compounds such as the species, signaling entities, biomolecules, and/or particles as described. The kits also may contain instructions for mixing, diluting, and/or administrating the compounds. The kits also can include other containers with one or more solvents, surfactants, preservative and/or diluents (e.g. normal saline (0.9% NaCl, or 5% dextrose) as well as containers for mixing, diluting or administering the components to the sample or to the patient in need of such treatment.

The compounds in the kit may be provided as liquid solutions or as dried powders. When the compound provided is a dry powder, the powder may be reconstituted by the addition of a suitable solvent, which also may be provided. Liquid forms of the compounds may be concentrated or ready to use. The solvent will depend on the compound and the mode of use or administration. Suitable solvents for are well known for drug compounds and are available in the literature.

The term "cancer", as used herein, may include but is not limited to: biliary tract cancer; bladder cancer; brain cancer including glioblastomas and medulloblastomas; breast cancer; cervical cancer; choriocarcinoma; colon cancer; endometrial cancer; esophageal cancer; gastric cancer; hematological neoplasms including acute lymphocytic and myelogenous leukemia; multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Preferred cancers are; breast, prostate, lung, ovarian, colorectal, and brain cancer.

The term "cancer treatment" as described herein, may include but is not limited to: chemotherapy, radiotherapy, adjuvant therapy, or any combination of the aforementioned methods. Aspects of treatment that may vary include, but are not limited to: dosages, timing of administration, or duration or therapy; and may or may not be combined with other treatments, which may also vary in dosage, timing, or duration. Another treatment for cancer is surgery, which can be utilized either alone or in combination with any of the aforementioned treatment methods. One of ordinary skill in the medical arts may determine an appropriate treatment.

An "agent for prevention of cancer or tumorigenesis" means any agent that counteracts any process associated with cancer or tumorigenesis described herein. For example, an agent that interacts with (e.g. binds to) to MGFR thereby reducing or preventing interaction, with MGFR, of an agent that promotes tumorigenesis by its interaction with MGFR.

An "agent that reduces cleavage of a cell surface receptor interchain binding region" as used herein is any composition that prevents or reduces cleavage of the MUC1 receptor between the MGFR and the IBR that would otherwise occur in the absence of the agent. Cleavage of the receptor between the MGFR and the IBR can be caused by activity of enzymes that are membrane-associated or soluble. Some of these enzymes are directly responsible for cleavage. Other enzymes can affect cleavage, (e.g. prevent cleavage at a particular location) by modifying MUC1 with sugar groups or phosphates that mask a recognition epitope associated with cleavage. Other enzymes can promote cleavage at a particular location by modifying MUC1 with sugar groups or phosphates that create a recognition motif for cleavage at that location. One way to select agents that reduce cleavage of a cell surface receptor IBR is to first identify enzymes that affect cleavage as described above, and screen agents, and their analogs, for their ability to alter the activity of those enzymes. Another way is to test agents that are known to affect the activity of similar enzymes (e.g. from the same family) for their ability to alter the site of cleavage of MUC1, and to similarly test analogs of these agents. Alternatively, agents are screened in a cell-free assay containing the enzyme and MUC1 receptors, and the rate or position of cleavage measured by antibody probing, Polymerase Chain Reaction (PCR), or the like. Alternatively, without first identifying enzymes that affect MUC1, agents are screened against cells that present MUC1 for the agents' ability to alter cleavage site or the rate of cleavage of MUC1. For example, agents can be screened in an assay containing whole cells that present MUC1 and aggregation potential of the cell supernatant can be measured, an indication of the amount of IBR that remains attached to the cleaved portion of MUC1, i.e. the degree of cleavage between MGFR and IBR. In another technique, agents can be screened in an assay containing whole cells that present MUC1, the supernatant removed, and the cell remain tested for accessibility of the MGFR portion, e.g. using a labeled antibody to the MGFR. Agents can be identified from commercially available sources such as molecular libraries, or rationally designed based on known agents having the same functional capacity and tested for activity using the screening assays.

An "agent that reduces cleavage of the MUC1 receptor" is any composition that prevents or reduces cleavage of the MUC1 receptor at any location. Such an agent can be used to treat a subject having cancer or at risk for developing cancer because if cleavage is prevented, then the accessibility of the MGFR, a functional receptor associated with cancer, is reduced or prevented. Such agents can be selected by exposing cells to a candidate agent and determine, in the supernatant, the amount of cleaved MUC1 receptor, relative to a control.

A subject, as used herein, refers to any mammal (preferably, a human), and preferably a mammal that may be susceptible to tumorigenesis or cancer associated with the abherrant expression of MUC1. Examples include a human, non-human primate, cow, horse, pig, sheep, goat, dog, or cat. Generally, the invention is directed toward use with humans.

The samples used herein are any body tissue or body fluid sample obtained from a subject. Preferred are body fluids, for example lymph, saliva, blood, urine, and the like. Blood is most preferred. Samples of tissue and/or cells for use in the various methods described herein can be obtained through standard methods including, but not limited to: tissue biopsy, including punch biopsy and cell scraping, needle biopsy, and collection of blood or other bodily fluids by aspiration or other methods.

The following patent applications and publications are incorporated herein by reference: international patent application serial no. PCT/US00/01997, filed Jan. 25, 2000, entitled "Rapid and Sensitive Detection of Aberrant Protein Aggregation in Neurodegenerative Diseases", published as no. WO 00/43791, international patent application serial no. PCT/US00/01504, filed Jan. 21, 2000, entitled "Assays involving Colloids and Non-Colloidal Structures", published Jul. 27, 2000 as international patent publication no. WO 00/34783, U.S. patent application Ser. No. 09/631,818, filed Aug. 3, 2000, entitled "Rapid and Sensitive Detection of Protein Aggregation", a U.S. provisional patent application by Bamdad, et al., Ser. No. 60/248,865, filed Nov. 15, 2000, entitled "Endostatin-Like Angiogenesis Inhibition," and a U.S. Utility Application Application of same title filed Nov. 15, 2001.

The present invention involves, generally, novel molecular targets for drug screening, therapeutics and diagnostics related to cancers that are characterized by the aberrant expression of a class of cell surface receptors characterized by interchain binding regions. One such set of cancers are those characterized by the aberrant expression of MUC1. Much of the description of the invention herein involves cells that aberrantly express MUC1. It is to be understood that in these instances the description is to be considered exemplary, and that the principles of the invention apply to other cell surface receptors that function by a similar mechanism. With the disclosure herein, those of ordinary skill in the art will readily be able to identify other cell surface receptors that function by this or a similar mechanism, and to apply the invention to those cancers characterized by aberrant expression of receptors. The invention is based on a novel mechanism involving cell surface receptors that have regions that self-aggregate, exemplified by MUC1, which was elucidated by the inventors.

MUC1 comprises several regions termed herein as follows, recited in an order starting from the region closest to the cell surface and progressing away from the cell. In at least one U.S. provisional patent application ("earlier application(s)") filed by the same inventors, entitled "Tumor Markers and Drug Screening for Tumorogenesis Inhibition", relating to MUC1 diagnostics and other techniques, at least one region of MUC1 was defined differently. It is to be understood that the following definition supercedes. Those of ordinary skill in the art will understand the invention in all its aspects from the description of portions of MUC1 referred to differently in the earlier application(s) and in the current application, and the relation of the earlier application(s) to this application. (1) the PSMGFR was referred to in the earlier application(s) as an FLR region or peptide); (2) the PSIBR was referred to in the earlier application(s) as a CM region or peptide. The basic structure of the MUC1 receptor is illustrated in FIG. 1. The receptor, as illustrated comprises: 1) cytoplasmic tail; 2) transmembrane section; 3) MGFR; 4) IBR, and 5) repeats.

One aspect of the present invention features the discovery that a specific region of the MUC1 receptor, i.e., the IBR, binds strongly to identical regions of other MUC1 molecules. That is, the MUC1 receptor has the ability to aggregate (i.e. self-aggregate) with other MUC1 receptors via the IBR of the respective receptors. This self-aggregation may contribute to MUC1 receptor clustering, observed in healthy cells. The discovery that the IBR portion of the MUC1 receptor self-aggregates is consistent with the following mechanistic model for which the inventors present supporting evidence. Mechanistic model: (1) receptor clustering is associated with the healthy state because the aggregated IBR portions block access of ligands, such as growth factors, modifying enzymes and the like to the neighboring extracellular portions of the MUC1 receptor that act as the functional receptor; clustering also blocks access of intracellular tails to intracellular modifying enzymes and signaling ligands; (2) when the MUC1 receptor is cleaved at a position that releases the IBR, the critical force that keeps the receptors clustered is lost and receptors are free to migrate within the cell membrane or interact with modifying enzymes, secreted ligands such as activating ligands or growth factors or other cell surface receptors; these interactions could involve a new, inductive multimerization state, such as dimerization, that triggers a cell proliferation signaling cascade.

Cleavage of MUC1 may occur at a site at or near the C-terminal boundary of the IBR in tumor or cancer cells (between the cell and the IBR), releasing the IBR from the cell. Alternatively, cleavage of MUC1 may occur within the IBR itself to cause sufficient disrupting of the IBRs such that the ability to self-aggregate is lost with the result that the MGFR becomes accessible to agents or ligands. As described in Example 1b, the addition of 9 amino acids of the IBR region to a peptide from the MGFR region (which does not self-aggregate), confers some ability to self-aggregate. Alternatively, loss of aggregation of MUC1 receptors need not necessarily be the result of cleavage. For example, an IBR can be absent as a result of alternative splicing of the MUC1 gene.

Before the present invention, a ligand(s) for the MUC1 receptor had not been conclusively identified. Research articles suggested that the shed portion of the MUC1 receptor becomes a ligand for the portion of the receptor that remains attached to the cell surface after cleavage. In the present invention, this hypothesis was tested, and it was determined not to be the case. Further, it was determined that altered sites of cleavage of the MUC1 receptor could result in altered function. In a colorimetric colloid binding assay (described in PCT/US00/01997, referenced above, as well as some other assays of the above-incorporated patent applications/publications) various fragments of the MUC1 receptor were tested for their ability to interact with each other fragment of MUC1 as well as for their ability to self-aggregate. We found that one portion of the receptor, fairly close to the cell surface, aggregated with itself in a high affinity interaction. This suggested that this portion of the MUC1 receptor, which we termed the interchain binding region, kept the receptors tightly clustered in a healthy cell, and that enzyme cleavage of MUC1 at a site that released the IBR, would cause the receptors not remain clustered. This clustering may affect cell signaling in two ways. First, the clustering of the receptors on the cell surface may restrict access to portions of the receptor that are binding sites for ligands such as modifying enzymes or growth factors. Secondly, as is appreciated by those skilled in the art, the intracellular portions (cytoplasmic tails) of many cell surface receptors are involved in signaling cascades that control programmed cell growth (proliferation) as well as programmed cell death (apoptosis). Receptors that are tightly clustered on the cell surface also have clustered cytoplasmic tails within the cell, which may prevent them from interacting with intracellular proteins involved in intracellular signaling.

In some cases, the MUC1 receptor may be cleaved to release the IBR, from the cell surface. Alternatively, cleavage can result in a release of a sufficient portion of the IBR that causes the MUC1 receptor to lose the ability to self-aggregate. Loss of aggregation of MUC1 may have several ramifications. Release of the IBR or sufficient portion of the IBR from the cell surface allows the receptors to evenly distribute on the cell surface, leaving the cytoplasmic tails free to associate with intracellular signaling proteins. External agents, such as modifying enzymes and/or activating ligands, are then able to bind to the remaining extracellular portion of the receptor and induce disease-associated signals, either via a change in the multimerization state, i.e., inductive multimerization, or as an induced conformational change. As is appreciated by those of ordinary skill in the art, ligands such as growth factors and hormones often induce receptor dimerization which triggers, in turn, an intracellular signaling cascade.

Cell proliferation may result from accessibility of the MGFR portion to an activating ligand which can interact with the MGFR portion. For example, the self-aggregating IBR of the MUC1 receptor may form a dense reticulum which sterically prevents a ligand such as a growth factor from interacting with the MGFR portion of the receptor, which is proximal to the cell relative to the IBR. In a cancerous or tumor cell, this reticulum may be lost, allowing ligand interaction with the MGFR.

The above mechanistic model is consistent with a mechanism whereby the portion of the MUC1 receptor, that remains attached to the cell surface after shedding of the IBR region, i.e. the MGFR, functions as a receptor for ligands that trigger cell proliferation. Evidence is also presented herein that indicates that this portion of the receptor is enzyme modified before it is able to be recognized by at least one of its ligands (See Example 8). This mechanism is demonstrated herein with a showing that: (a) an interaction between a ligand and this portion of the MUC1 receptor (MGFR), which dimerizes the receptor, triggers cell proliferation; and (b) blocking the interaction of this portion of the MUC1 receptor (MGFR) with its ligand(s), blocks cell proliferation. When tumor cell lines, in which the MUC1 receptor is homogeneously expressed across the entire cell surface, are treated with an IgG antibody raised against the MGFR portion of the MUC1 receptor, the rate of cell proliferation is greatly enhanced, see FIG. 5. Since IgG antibodies are bivalent, i.e. one antibody simultaneously binds to two adjacent MGFR portions on the cell surface, these results demonstrate that the antibody acts as an activating ligand, mimicking the effect of a growth factor, which dimerizes MGFR portions, and thus triggers a cell proliferation signaling cascade which is consistent with signaling via the cytoplasmic tails of the receptors. This finding leads to two conclusions. First, an activating ligand(s) that binds to the MGFR portion of the MUC1 receptor causes inductive multimerization of the receptor. Secondly, an effective therapeutic strategy is therefore to block the MGFR portion of the receptor with a monomeric composition, thus preventing inductive multimerization and subsequent signaling cascades. For example, a single chain, or monovalent, antibody raised against the MGFR portion of the MUC1 receptor would function as an effective anti-cancer therapeutic. Another therapeutic strategy is to block the activity of enzymes that modify the receptor, which may be required for some ligand binding The inventors have also discovered that cells that overexpress the MUC1 receptor also have increased levels of a ligand(s) that dimerizes the MGFR present in the lysates and supernatants of these cells, see Example 3b and FIG. 8A-D for details. In the colloid-colloid interaction experiment, described in Example 3b, ligands that simultaneously bind more than one colloid-immobilized receptor, i.e. dimerize, cause a solution color change from pink to blue. Gold colloids that presented synthetic peptides derived from the MGFR portion of the MUC1 receptor (His-PSMGFR) were incubated with lysates/supernatants from various cells lines known to overexpress, express, or not express the MUC1 receptor. Lysates from HTB-133 (T47D) cells, which overexpresses MUC1 (see Table 2), caused colloid suspensions to turn blue within 15 minutes, indicating a high concentration of a ligand(s) in the lysate that interacts with the colloid-immobilized MGFR-derived peptides. In experiments with lysates from other cell lines, the rate of color change of the colloid solution, which indicates the amount of ligand present, correlated to the degree of expression of the MUC1 receptor in those cell lines with cells.

Figure 20:
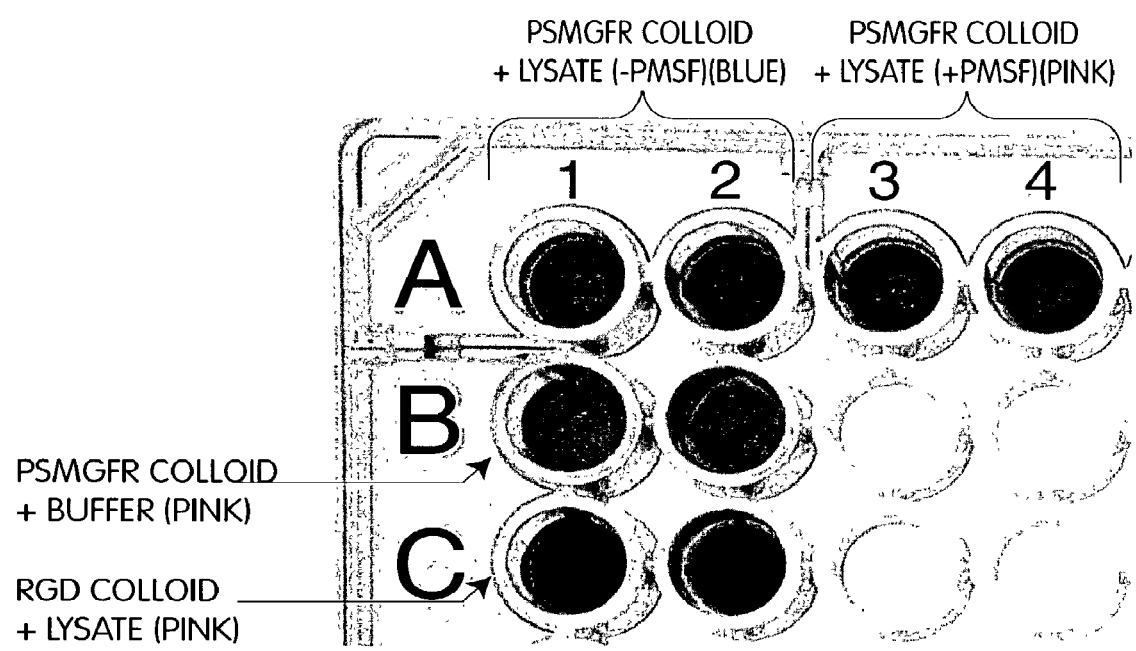
FIG. 20 is a black and white photocopy of an image of a 96-well plate illustrating a color-change ligand binding assay illustrating that inhibiting enzymatic modification of PSMGFR prevents it binding to ligands.

More than one species may be a physiologically relevant ligand for this portion of the MUC1 receptor. Enzymes that modify the receptor may be relevant ligands of this portion of the receptor. For example, one ligand may bind monomerically to an unmodified MGFR portion of the MUC1 receptor, while another ligand, with a different function, such as inductive multimerization, may recognize an enzyme-modified version of the receptor. Because the experiment described above, Example 3b, was performed in cell lysate/supernatants, it is important to note that several receptor-ligand interactions, including enzymatic modifications to the receptor, may be taking place, wherein only the ligand(s) dimerization (or multimerization) of the MGFR portion, results in a solution color change. In an experiment similar to Example 3b, (Example 8) the enzyme inhibitor, PMSF was added to the lysate prior to the introduction of the colloids bearing the synthetic peptide His-PSMGFR, see Table 1 SEQ ID # 2. Referring now to FIG. 20, solutions that contained PMSF did not undergo the solution color change. This result is consistent with a mechanism in which the MGFR portion of the MUC1 receptor is first enzyme modified before it is recognized by the ligand(s) that dimerize or multimerize the receptor The inventors reasoned that prior attempts by others to identify ligands for the MUC1 receptor were hampered by the self-aggregation properties of the receptor. Therefore, only the MGFR portion of the receptor was used as bait to fish ligands out of lysates and supernatants. The His-PSMGFR sequence of Table 1, was immobilized on NTA-nickel beads via the histidine tag of the peptide, the beads were then incubated with lysates and supernatants from a variety of cell types, including cancer cell lines that overexpress MUC1. Enzyme inhibitors such as PMSF were added to some of the lysates and supernatants to circumvent problems of alternative ligands binding to modified versions of the peptide. Following incubation of the cell supernatants with the PSMGFR-presenting beads, the beads were washed, then the peptide-ligand complexes eluted from the NTA-Nickel beads by adding excess imidazole. Captured ligands from the probe peptides, eluates, were separated using standard SDS-PAGE methods. Protein bands were excised from the gels and analyzed to identify the target ligands. Standard methods for protein analysis including peptide micro sequencing and tandem mass spec were used in these studies. Other methods can be used to identify MUC1 ligands, including ligand fishing with beads, MALDI mass spec, and the like.

Figure 9:
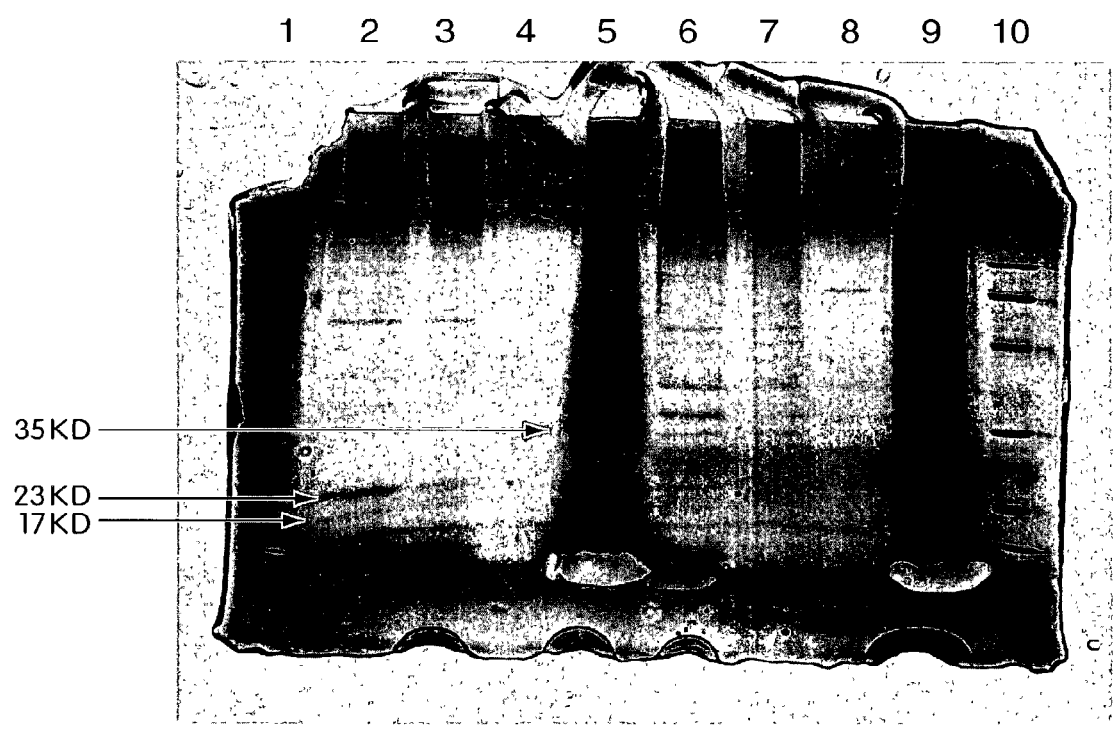
FIG. 9 is a black and white photocopy of a silver-stained gel showing ligands that were fished out of cell lysates using the PSMGFR peptide, in the presence of the protease inhibitor PMSF.
Figure 10:
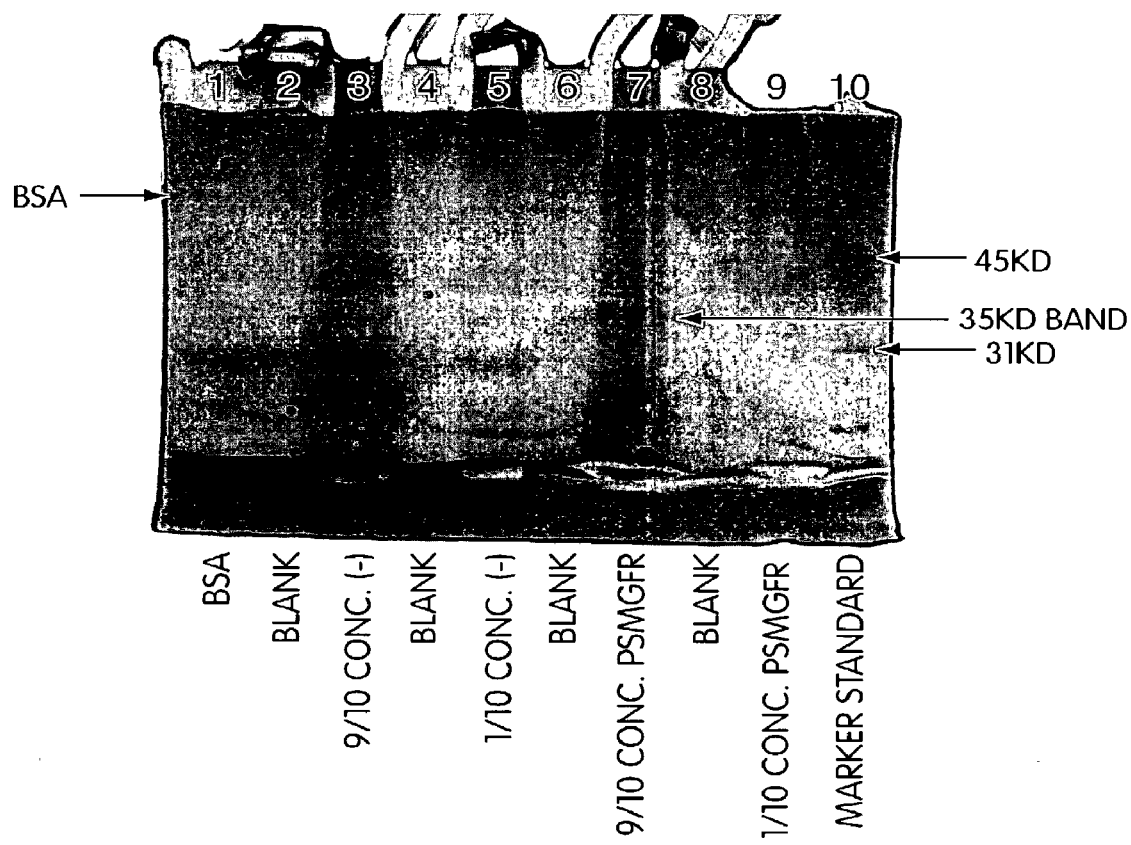
FIG. 10 is a black and white photocopy of a silver-stained gel showing ligands that were fished out of cell lysates using the PSMGFR peptide, in the absence of the protease inhibitor PMSF.

Accordingly, another aspect of the invention involves the identification of ligands, derived from lysates from a cell line selected from the group consisting of HTB-133, CRL-1504, and CRL-1500, that bind to the MGFR portion of the MUC1 cell surface receptor, see FIGS. 9 and 10. In some embodiments, the ligands may include sequence(s) from: Metastasis Inhibition Factor NM23, 14-3-3, Cathepsin D, annexin, Beta lipotropin (Beta-LPH), beta-melanotropin or Beta-MSH. In other embodiments, the biomolecule that binds to the MGFR portion may be a cleavage product of proopiomelanocortin (POMC). In all embodiments, the preferred cell surface receptor is MUC1. In one embodiment, the MGFR portion includes some or all of the sequence from the PSMGFR peptide (SEQ ID NO: 7). These ligands may exist in a multimeric state including dimers, tetramers, or complexes containing some or all of these ligand species. In one aspect, the invention involves modification and use of the above species as anti-cancer agents.

In one embodiment the ligand is a 23 kD protein. In another embodiment, the ligand is approximately 17 kD. In a preferred embodiment, the ligand identified is a protein that migrates through a gel with an apparent molecular weight of 35 kD. Since this species is much more apparent when the protease inhibitor PMSF is not added to the lysate (FIG. 10), this protein may be an enzyme that modifies the MUC1 receptor or a ligand that recognizes the unmodified version of the receptor. Experiments were performed as described in more detail below in Example 4b to characterize these species.

Peptide sequences contained within both the 17 kD and the 23 kD bands (PMSF added to lysate) corresponded to a protein known as Metastasis Inhibition Factor NM23, which has been implicated in both the promotion and inhibition of metastasis of human cancers. Whether the role of NM23 is a tumor supressor or promoter may depend on the type of cancer. In ovarian, colon and neuroblastoma tumors, NM23 overexpression has been linked to a more malignant phenotype (Schneider J, Romero H, Ruiz R, Centeno M M, Rodriguez-Escudero F J, "NM23 expression in advanced and borderline ovarian carcinoma", *Anticancer Res*, 1996; 16(3A): 1197-202). However, breast cancer studies indicate that reduced expression of NM23 correlates with poor prognosis (Mao H, Liu H, Fu X, Fang Z, Abrams J, Worsham M J, "Loss of NM23 expression predicts distal metastases and poorer survival for breast cancer", Int J Oncol 2001 March; 18(3):587-91). Because NM23 exists as a hexamer, in MUC1-presenting cells, it may function to hold MUC1 receptors in a clustered configuration to restrict access of the MGFR to modifying and activating ligands. The sequences that were identified from the protein gel band described in FIGS. 9 and 10 and that also exist in Metastasis Inhibition Factor NM23 are shown below in Table 4

Peptide sequences that are associated with the 35 kD gel band (PMSF NOT added to lysate) corresponded to more than one protein species, including 14-3-3, which is a signaling protein implicated in many cancers, and cathepsin D, which is a protease and is also implicated in tumor progression. 14-3-3 exists as a dimer and can simultaneously bind to two, identical phospho-serine peptides. This protein has been shown to be involved in intracellular signaling, but particularly relevant to this invention is the fact that 14-3-3 has been shown to be secreted by some cell types, including dendritic cells. Ligands that bind to the MGFR portion of the receptor to induce inductive multimerization would tend to be secreted factors. This protein would dimerize the MUC1 receptor to trigger cell proliferation, which is consistent with the mechanism presented herein. Cathepsin D is a protease and may be involved in the cleavage of the MUC1 receptor.

Yet another aspect of the invention involves the identification of other ligands, also derived from supernatants from a cell line selected from the group consisting of HTB-133, CRL-1504, and CRL-1500, that bind to the MGFR portion of the MUC1 cell surface receptor. In one embodiment, the ligand identified is a protein that migrates through a gel with an apparent molecular weight of 55kD. In another embodiment, the ligand is approximately 70kD; 80kD; or 100kD. In a particular embodiment, the ligand present in cell supernatants is a 13kD protein, see FIG. 9., which migrates though gel with apparent molecular weight of 13kD. The protein with an apparent molecular weight of about 13kD appears upon polyacrylamide gel electrophoresis as a smeared band which may indicate that the protein is glycosylated, enzyme modified, or that the band contains more than one protein species. Using mass spec and maldi mass spec techniques, combined with homolgy to peptide sequences in the GENBANK® database, it was determined that two fragments derived from the 13kD corresponded with a high degree of homology to beta-lipotropin (Odell W, Wolfsen A, Bachelot I, and Hirose F, (1979) "Ectopic production of lipotropin by cancer" *The American Journal of Medicine* 66; pgs. 631-638), which was previously known as beta-MSH (beta-melanotropin). Beta-lipotropin (beta- LPH: 98 amino acids or about 10kd) and ACTH (aa' 130-169) are cleavage products of proopiomelanocortin (Publisher Williams & Wilkins, chapter authors: Faye W, Lemke T, Williams D, Text book—Principles of Medicinal Chemistry; Fourth edition 1995) (POMC: 260 amino acids). Because these peptides are glycosylated, their apparent molecular weights can be altered from their actual molecular weights. These cell surface receptor binding ligands can be purified or produced using techniques known to those of skill in the art. It is also possible that in certain situations an external ligand does not bind to and dimerize the MGFR portions of the MUC1 receptor to trigger cell proliferation, but rather the receptors become covalently coupled to each other, for example by an enzyme that covalently links the two. One way this could be accomplished is by an enzyme that attaches an entity, such as a sugar group, to both receptors.

Because the portion of the MUC1 receptor that self-aggregates (IBR), and in doing so may protect intracellular signaling sequences from participating in signaling cascades that induce proliferation, can be cleaved and shed from the cell surface, it can be beneficial to identify small molecules that interact with the MGFR portion of MUC1 that remains cell-attached (MGFR). These small molecules that bind to the portion of MUC1 that remains cell-attached (MGFR) can then be used in two ways. First, they can be used to block the remaining, cell-attached portion of the MUC1 receptor so that it cannot interact with activating ligands that induce proliferation and metastasis. For example, a ligand to the cell-attached portion of MUC1 may effect inductive multimerization of the receptor, causing a signaling cascade inside the cell. Blocking binding of the ligand to the MGFR region can inhibit the signaling cascade that causes proliferation. Secondly, as discussed in more detail below, the small molecules can be polymerized or attached to dendrimers to artificially cause preventative clustering the cell-attached MGFR portions of the MUC1 receptors and thus shield the cytoplasmic tails from interaction with intracellular signaling proteins.

The findings of the invention have important implications for diagnostic and therapeutic procedures. For instance our finding that a fragment of the MUC1 receptor that is close to the cell surface aggregates with itself, indicates that the position of enzyme cleavage is associated with receptor clustering, accessibility of adjacent portions of the receptor to putative ligands, and thus cancer. Agents that modulate the activity of this enzyme may be potent anti-cancer agents. Additionally, an early diagnostic test for cancers that aberrantly express MUC1 may be based on detecting the portion of MUC1 that self-aggregates (IBR) circulating in bodily fluids. This portion of MUC1 includes part or all of the PSIBR (sequence shown in Table 1). Agents that bind to the portion (some or all of the PSMGFR sequence) of MUC1 that remains attached to the cell surface after the release of the portion that self-aggregates (IBR—some or all of the PSIBR sequence) may be potent anti-cancer drugs. In addition, agents that block binding of the natural ligand to the remaining portion after the release of the IBR, may also be useful as anticancer drugs. Drug candidates that target portions of the MGFR, ie., sequences including some or all of the amino acids contained within the PSMGFR, of the receptor can be used either as monomers, to block the interaction of the MGFR portion of MUC1 with extracellular agents or biomolecules, or as a polymer, dendrimer, etc. to both block the interaction with external biomolecules and to artificially cluster the MGFRs. Another alternative agent, which can be used to artificially cluster the MGFRs is an IgM antibody raised against the MGFR or PSMGFR. This artificially-induced clustering may serve to keep the cytoplasmic tails clustered to prevent interaction with intracellular signaling agents, thereby effecting preventative clustering.

One aspect of the invention involves novel drug screening assays, that identify therapeutics that interfere with the proliferation of tumor cells that aberrantly express MUC1. The drug screen makes use of the new molecular target for cancer that is disclosed herein. Another aspect of the invention involves therapeutics identified by the drug screen. Yet another aspect of the invention involves methods for diagnosing MUC1$^+$ cancers, which is based upon the mechanism elucidated by the inventors.

Figure 12:
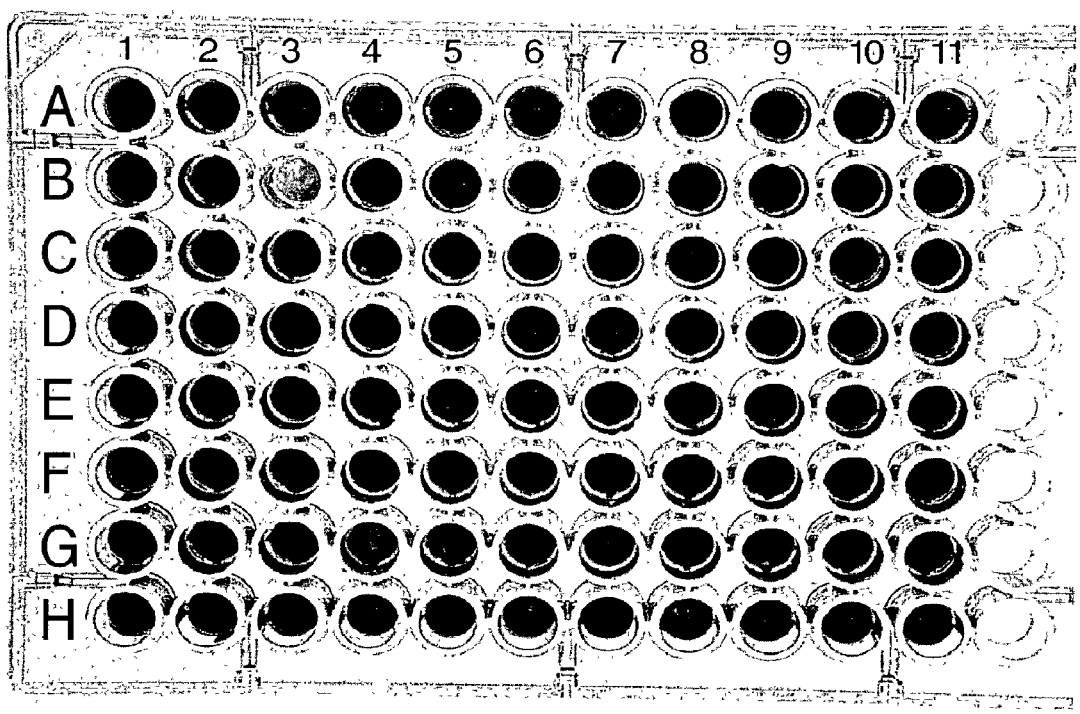
FIG. 12 is a black and white photocopy of an image of a 96-well plate illustrating a color-change drug-screening assay used to detect inhibitors of the MUC1-Ligand interaction.

One embodiment of the invention involves a drug screening assay which can rapidly identify agents that interrupt the interaction between the MGFR and its ligand(s) and thus can be used as cancer therapeutics, (see Example 5a and FIG. 12 for details). The fact that an activating ligand(s) that binds to the MGFR portion of the MUC1 receptor can result in inductive multimerization of the receptor, allows us to construct a convenient drug-screening assay to identify compounds that inhibit this interaction or inhibit enzymes that modify the MGFR portion required for ligand binding and thus inhibit the proliferation signal. In one assay of the invention, synthetic peptides which include much or all of the MGFR sequence are attached to nanoparticles such as gold colloids. Gold colloids have the intrinsic optical property that when in a disperse, homogeneous solution, the solution appears pink, but when the colloids are forced into close proximity, the solution turns blue. When cell lysates or supernatants, which contain a ligand(s) that dimerizes the colloid-attached peptides, are added, the colloids becomes aggregated and the solution turns blue. Drug candidates that interrupt this ligand-receptor interaction are easily identified because they cause the solution to remain pink.

As discussed above, it appears that the ligand that binds to the MGFR portion of the receptor to trigger inductive multimerization may recognize an enzyme-modified form of the receptor. Therefore the above-described drug screening assay can identify compounds that: a) inhibit enzyme modification of the MGFR portion of the MUC1 receptor; b) bind to the MGFR region and block its interaction with an activating ligand of the MGFR portion; or c) bind to an activating ligand, such as a growth factor and block its interaction with the MGFR portion. Drugs that act according to (a) or (b) are predicted to selectively inhibit MUC1-dependent cell proliferation, whereas drugs that act according to (c), on agents such as growth factors, are expected to inhibit proliferation of a variety of cell types, see Examples 5a-d.

Drugs that have been found by the above protocol to disrupt an interaction between the MGFR portion of the MUC1 receor and its ligand(s) are described in much greater detail below and include, for example, calcimycin, fusaric acid, L-α-methyl-dopa, butylindazone, NS1619 or etomoxir. Additional drugs are described in greater detail in applicant's co-pending U.S. Provisional Patent Application Ser. Nos. 60/317,302 and 60/317,314, both filed on Sep. 5, 2001 and entitled COMPOSITIONS AND METHODS OF TREATMENT OF CANCER.

Agents so identified may be potent anti-cancer agents either in monomeric form or as polymers or dendrimers. Drug libraries and peptide libraries can be screened for molecules that inhibit binding of the ligand to its target.

Alternatively, standard methods can also be used to identify agents that interrupt the interaction between the MGFR and its ligand(s). These methods can be used to identify agents that bind: (1) to the MGFR portion of the MUC1 receptor, or (2) to one or more of its ligands. These methods include but are not limited to phage display methods, yeast two-hybrid system, sandwich assays, surface plasmon resonance-based assays, antibody-based assays, peptide bead assays for testing with drug libraries, bead assays, GFP-reporter assays, and the like. Ligands to the MGFR portion of the MUC1 receptor can be identified by a number of methods including using a peptide whose sequence corresponds to some or all of the MGFR, ie. the PSMGFR peptide (Sequence ID 7), as bait to fish out ligands. Another way to do this is to attach a signaling entity, such as GFP (green fluorescent protein), directly or indirectly to the ligand and attach the receptor-derived peptide to a solid support. Compounds that interfere with the interaction will cause a loss of signal.

As an alternative to the natural ligand competition assays described above, direct binding assays can be employed to identify drug agents able to interact with the MGFR. Small molecules that bind to the remaining extracellular portion of cleaved MUC1 (MGFR region: exemplified by most or all of the PSMGFR peptide sequence), can be identified using standard methods (MALDI, western blotting, gel electrophoresis, ELISA, etc) or using colloid-colloid or colloid-bead binding assays. For example, in one embodiment, small molecules can be synthesized on beads or attached to colloids either by attachment to a thiol and direct incorporation into a SAM on the colloid or by EDC/NHS coupling of molecules containing a primary amine. A histidine-tagged peptide including the desired MUC1 (e.g. His-PSMGFR) sequence can be bound to colloids and assayed for interaction with a second set of colloids presenting a candidate drug. A color change from pink to blue would indicate an interaction between the MUC1 peptide and the small molecule. Alternatively, the MUC1-bearing colloids can be assayed for an interaction with a small molecule attached to a bead. Red coloration of the bead surface would signify that the MUC1 peptide bound to the bead-immobilized small molecule.

Any drugs or small molecules identified as binding to the MUC1 sequence can potentially be used to block binding of the remaining extracellular portion of cleaved MUC1 to its natural ligand, and can potentially inhibit cancer growth.

In another embodiment, the above-described competition assays are employed to identify "second generation" drug candidates by assaying such candidates for their ability to disrupt an interaction between the MGFR portion of the MUC1 receptor and a synthetic ligand found, according to the inventive methods described above, to bind to the MGFR, e.g. calcimycin, fusaric acid, L-α-methyl-dopa, butylindazone, NS1619 or etomoxir. In this way, drugs that bind the MGFR with higher affinity than the "first generation" drug can be identified. For example, in performing the drug screen, a synthetic ligand such as calcimycin, fusaric acid, L-α-methyl-dopa, butylindazone, NS1619 or etomoxir is modified to facilitate attachment to surfaces, such as colloids. A peptide derived from the MGFR region of the MUC1 receptor, such as the His-PSMGFR, is attached to a second set of colloids. Direct binding between the synthetic ligand and the MGFR peptide is confirmed, a library of drug candidates are then assayed for their ability to disrupt the interaction. It is not intended that this aspect of the invention be limited to the competition techniques or assays explicitly described herein. Several techniques, including standard methods, could potentially be used to detect binding between the MGFR and a synthetic ligand or drug, then competitive inhibition of binding by a drug candidate.

Another aspect of the invention is a drug screening assay for identification of drugs that can be useful for prevention and/or treatment of cancer by altering the cleavage state of MUC 1 receptors on cells. In such assays, described in more detail below, cultured cells are exposed to candidate drugs. The cleavage state of MUC 1 in the cells is determined, optionally as a function of time and/or dosage or other conditions involving exposure to the drugs. These cells can be derived from a particular patient, or can be tumor-associated or non-tumor-associated cell lines. Customized therapeutic protocols can be determined for a particular patient in this manner. The invention involves, in one aspect, treating a patient with a drug, as discussed in greater detail below, shown to affect the cleavage state of MUC 1 of the patient's cells in a manner that prevents, inhibits, or reverses cancer.

Because it is suspected that the incorrect cleavage of MUC1 on the surface of the cell causes the cascade leading to proliferation and tumorigenesis, it would be advantageous to test candidate drugs in a whole cell assay for their ability to affect enzyme cleavage or the position of enzyme cleavage of MUC1. Drugs can be screened for their ability to effect MUC1 cleavage, either directly or indirectly. This can enable the identification of upstream effectors of MUC1 cleavage. Cells or tissue samples can be assayed for MUC1 cleavage potential in several ways. For example, cells or a tissue sample can be treated with a drug candidate and grown for some period of time. Colloids bearing an antibody, natural ligand, or small molecule that binds to either the cleaved portion of MUC1, or the remaining extracellular portion (plus or minus a signaling moiety) can be added and allowed to bind to the cells or tissue sample. The expression of cleaved MUC1 or uncleaved MUC1 on the cell surface as compared to a control sample, not treated with the candidate drug, would indicate whether the drug candidate effected MUC1 expression or cleavage.

Alternatively, MUC1 expressing cells can be assayed for MUC1 cleavage in the presence of a drug candidate by testing the surrounding cell growth media for the presence of cleaved MUC1 or the potential of the cleaved portion to self-aggregate. For example, cells expressing MUC1 would be treated with a drug candidate suspected of interfering with enzyme cleavage. After some incubation period, the cell media would be removed and tested for its aggregation potential, i.e. to determine whether the self-aggregating portion of MUC1 was contained within the shed fragment. The aggregation potential of peptides released into the cell media is tested by adding colloids bearing an antibody to a sequence distal from the self-aggregating portion, but not a repeat sequence. In this way, antibody-presenting colloids would attach to upstream regions of MUC1. If the self-aggregating region was also attached to the released fragment, then this would cause aggregation of the attached colloids and a solution change from pink to blue would result. Accordingly, one aspect of the invention provides a composition (drug or agent) that, in contrast to preventing inductive multimerization of cleaved or modified MUC1 receptors as discussed previously, instead prevents disease-associated MUC 1 cleavage or modification itself. MUC 1 cleavage is an enzymatic process. The determination of the mechanism involved by the inventors can lead to identification of a drug that inhibits disease-associated cleavage.

As mentioned above, another aspect of the invention provides an agent that binds together MGFR portions of MUC 1 following disease-associated cleavage to effect preventative clustering of the receptors. The agent can be any species that includes multiple sites each able to bind to a MFGR portion, and immobilized with respect to each other. E.g. a polymer or dendrimer or other continuous entity can include multiple sites each able to bind to a MGFR portion, causing clustering of these portions or other structural constraint that inhibits their association with factors that promote cell proliferation. Alternatively, IgM-type monoclonal or polyclonal antibodies raised against the MGFR or PSMGFR could be utilized. Each anti-MGFR IgM antibody could be able to aggregate ten MGFRs on the cell surface to form preventative clusters.

Accordingly, an aspect of the invention is an antibody or antigen-binding fragment thereof that specifically binds to MUC1 by binding to an epitope thereof contained within a region of the polypeptide consisting of at least 12 contiguous amino acids of the sequence at positions 1110-1154 of SEQ ID NO: 10, or alternatively at least 12 contiguous amino acids of the sequence at positions 1110-1142 of SEQ ID NO: 10.

In addition, some or all of the above-identified ligand species that bind to the MGFR can be modified to allow the ligands to act as a targeted delivery agent by attaching a cytotoxic drug or other agent (e.g. a radioactive substance) able to selectively kill cells to which the ligands become immobilized. In addition, synthetic ligands, such as calcimycin, fusaric acid, L-α-methyl-dopa, butylindazone, NS1619 or etomoxir, discussed in more detail below, that were found to bind to the MGFR portion of the MUC1 receptor can similarly be modified with other therapeutic agents. In this way, such a therapeutic can be directed to the tumor cells. For example, an agent that binds to the MGFR region of the MUC1 receptor can be modified with a radioactive substance to destroy tumor cells that aberrantly express the MUC1 receptor. Other toxic substances, such as ricin, as well as other therapeutics, can be attached to agents that bind the MGFR.

Alternatively, identified ligand species that bind to the MGFR could be modified to present a imaging agent for use in diagnostic imaging of MUC 1$^+$ tumors and metastases. Such ligands can also, alternatively, be modified to act as drugs that can be useful for prevention and/or treatment of cancer. In one embodiment, a ligand, which in its unmodified form binds to multiple MGFRs causing inductive multimerization, is modified to remove or de-activate all but one of its active binding sites for MGFR, such that each modified ligand is able to bind to only a single receptor. In another embodiment, individual ligand molecules/peptides are modified such that they are immobilized with respect to additional ligand molecules/peptides also able to bind MGFR, e.g. through covalent coupling, non-covalent coupling, co-immobilization with respect to a substrate, etc., such that the modified, multi-unit ligand is able to effect preventative clustering of the receptors to which it binds.

Identification of the ligand(s) for the portion of MUC1 that remains bound to the cell after cleavage can allow, as discussed further below, for development of powerful assays to screen for drugs that disrupt this interaction. Interaction of potential binding partners with the extracellular portion of MUC1 that remains after cleavage can be studied both by conventional techniques (western blotting, ELISA, MALDI, etc.) and using our colloid-colloid color change assay or colloid-bead coloration assay. The peptide sequence of the remaining extracellular portion of MUC1 can be attached to beads or colloids via a histidine tag. Potential binding partners can be histidine-tagged and attached to a second set of colloids (or beads) and assayed for binding to the colloid-immobilized portion of MUC1. Alternatively, potential binding partners can be attached to beads or colloids by EDC/NHS coupling or can be nonspecifically adsorbed to beads for the assay. An interaction between the MUC1 peptide and the potential binding partner can be detected by either a change in solution color (for the colloid-colloid assay) or by agglomeration of the colloids onto the bead, causing the bead to appear red (for the colloid-bead assay). An entire cDNA library can be screened using this technique in a short period of time to identify the natural ligand of the remaining extracellular MUC1. (see PCT/US00/01997, WO 00/34783, Ser. No. 09/631,818, and "Detection of Binding Species with Colloidal and Non-Colloidal Structures", filed Nov. 15, 2000, incorporated above).

The discoveries presented herein: (1) that the IBR of MUC1 self-aggregates; (2) that an antibody that dimerizes adjacent MGFR portions of the MUC1 receptor leads to proliferation of MUC1 presenting tumor cells; and (3) that proliferation of MUC1 presenting tumor cells can be inhibited by treatment with agents that target the MGFR and block the MGFR against interaction with a ligand, are consistent with a mechanism in which, in a healthy cell, MUC1 cleavage occurs such that enough of the IBR remains on the cell that MUC1 remains clustered, and the MGFR is inaccessible to ligands such as growth factors, and in a tumor cell, MUC1 cleavage occurs such that enough of the IBR is cleaved from the cell such that MUC1 does not remain clustered, and the MGFR is accessible to ligand interaction. This leads to diagnostics, provided by the present invention, in which the shed portion of MUC1 is analyzed to determine the degree of IBR present.

The above-mentioned mechanistic model predicts that in a subject with a MUC1-dependent tumor or who is prone to developing such a tumor, the portion of the MUC1 receptor that is shed will contain the IBR region of the receptor, leaving the MGFR portion of the receptor accessible for interactions with ligands and growth factors. An early diagnostic would consist of detecting the IBR region in the portion of the MUC1 receptor which is shed.

In one embodiment, loss of aggregation of MUC1 receptors can result from the "cleavage state" of MUC 1. "Cleavage state" defines the result of cleavage of MUC 1. The cleavage state will differ between a healthy cell and a cell with tumor potential. The cleavage state determination can involve determining whether cleavage occurs in a manner such that the normal interaction between the IBRs of neighboring receptors is disrupted (these regions no longer remain bound to each other at the cell) and MUC 1 is free to spread across the cell surface. More specifically, determination of the cleavage state can include determining a site of cleavage of MUC1, determining the identity of a portion of MUC 1 that remains at a cell following cleavage, determining the identity of a portion of MUC 1 that is separated from the cell following cleavage ("cleaved or shed portion"), determining the accessibility of MGFR, or a combination.

In one embodiment, an assay is provided that can determine whether the MUC1 IBR remains fastened to the cell, or is separated from the cell upon cleavage. The product of MUC1 cleavage from the cell is exposed to at least one surface adapted to bind the IBR and to another surface and/or a signaling entity. Generally, an assay as described in WO 00/43791 or WO 00/34783 can be used. In a specific example, antibodies to a portion of MUC1 that would remain fastened to the IBR if the IBR is cleaved from the cell, such as antibodies to the repeats domain, are fastened to colloids. Exposure of these colloids to the MUC1 cleavage products will allow the IBR regions to self-aggregate which in turn will result in colloid/colloid aggregation (color change to blue) for cases in which the IBR portion is separated from the cell. This is because each colloid will fasten to a MUC 1 region which is connected to an IBR which is fastened to another IBR which is in turn fastened to another colloid.

The discovery that tumor cells can be treated with an agent that binds to the MGFR of MUC 1, or a ligand of MGFR, in a manner that inhibits cell proliferation leads to the conclusion that, in a diseased cell (a cancerous cell or a cell with potential for becoming cancerous), cleavage of MUC 1 occurs in a manner that allows MGFR to interact with at least one ligand in a manner that promotes tumorigenesis or cancer. Interaction with the ligand may be due to cleavage that disrupts binding between different MUC 1 molecules at the cell surface, either via separation from the cell of the IBR during cleavage, or cleavage within the IBR at a location that frees MUC 1 molecules from each other.

In one aspect of the invention, a diagnostic is provided wherein an amount of cleavage of a cell surface receptor IBR from the cell surface is determined. This involves the determination of the amount of cell surface receptor IBR that is separated from the cell surface upon cleavage, which can be relative to the level determined in past samples, the level in control samples, or can be determined as a ratio of the amount of IBR to the amount of a constant region of the receptor in a sample. The constant region is any non-repeating sequence which is N-terminal to the boundary of the PSIBR, that is, this region is present in a 1:1 ratio with the PSIBR prior to cleavage—determination of the ratio of IBR to constant region subsequent to cleavage indicates the extent to which the IBR is cleaved and separated from the cell. The amounts of various receptor regions may be determined with any type of binding assay, e.g. an antibody-binding assay. For example, antibodies that specifically bind to the constant region or the repeats may be attached to surfaces (e.g. magnetic beads) to preconcentrate shed MUC 1 receptors prior to determining levels of IBR present. Then, for example, after pre-concentration of circulating MUC 1 receptors, antibodies to the IBR and antibodies to the constant region can be allowed to bind to the cleaved receptors, and determination of the ratio of binding of these antibodies reveals the ratio of IBR present relative to constant region present in the cleaved receptors, which in turn reveals the amount of cleavage that occurred in a manner that caused separation of the IBR from the cell. A ratio that displays a trend toward less than one (less than a 1:1 ratio of IBR relative to constant region present) for detecting IBR at a cell surface is an indicator of the presence of a tumor or the potential for the development of a tumor. A ratio that approaches 1:1 when detecting these regions in shed receptors is likewise an indicator of cancer potential. This determination can indicate potential for tumor formation, existence of a tumor, progression of tumorigenesis, etc., and can thereby serve as a diagnostic and/or a evaluator of treatment for tumorigenesis Another diagnostic aspect of the invention involves determining levels of shed IBRs in sample from a subject. Methods for such determination can include determining the aggregation potential of the circulating shed receptors, for example via colloid-binding assays such as a colloid-colloid assay or a colloid bead assay (See above discussion and Examples, below). Alternative techniques involve determining the presence of the IBR using antibody probing assays, hybridization, PCR Reverse Transcriptase PCR (rtPCR), Ligase Chain Reaction (LCR), cycling probe technology, etc. In a preferred embodiment of the invention, the cell surface receptor is MUC1.

The determination, in a blood sample, of the amount of cleaved receptor carrying IBR, either involving antibody binding ratios, colloid binding assays, or the like can be made on a bodily fluid sample, such as a blood sample and optionally compared with other samples (e.g. to monitor the subject's progression of tumorigenesis or progression for treatment of the same) and/or controls.

Alternatively, biopsy specimens can be studied, or tissue can be studied interoperatively (e.g. tissue at a surgical site can be studied without removal of the tissue from the subject). In either of these studies, a primary indicator of tumorigenesis or potential for tumorigenesis is the amount of MGFR at a cell surface accessible to interaction with external agents such as growth factors, etc. This determination can be made, for example, by determining the amount of an antibody to the MGFR region that binds to the sample, either using standard antibody binding study techniques, or by exposing the sample to colloids to which antibodies specific to the MGFR region have been immobilized and determining binding of the colloids to the samples using techniques described in International patent publication numbers WO 00/34783 and WO 00/43791, referenced above. In another technique (perhaps more suited for an excised sample), antibodies to the MGFR region and to the IBR can be exposed to the sample and a determination made of the ratio of binding of each to the sample. A healthy sample will exhibit little or no antibody binding to the MGFR region. A sample indicating tumorigenesis or potential for tumorigenesis will show a non-zero ratio of MGFR antibody binding to IBR antibody binding.

Whether shed MUC1 contains the IBR can be identified by methods known to those of ordinary skill in the art, including ELISA and colloidal assays as described in international patent application serial no. PCT/US00/01997, filed Jan. 25, 2000, entitled "Rapid and Sensitive Detection of Aberrant Protein Aggregation in Neurodegenerative Diseases", published as no. WO 00/43791, and U.S. patent application Ser. No. 09/631,818, filed Aug. 3, 2000, entitled "Rapid and Sensitive Detection of Protein Aggregation", by Bamdad et al. In a preferred embodiment of the invention, the cell surface receptor is MUC1.

Another aspect of the invention involves determining the site of cleavage of the MUC1 receptor from a cell surface (rather than the amount of IBR in a shed portion) in a sample from a subject to evaluate cancer, or the potential to develop cancer in a subject. Determination of the site of cleavage will give information as to whether the IBR remains on the cell surface, or was shed from the cell surface, giving indication of cancer or tumorigenesis or the potential for either, as discussed above. Determining the site of cleavage can be accomplished by using enzyme-amplification methods such as PCR. Specifically, using alternative primer sites in PCR amplification of shed MUC1 from subject's sample will indicate where cleavage occurred.

In one aspect of the invention, differences in pre- and post-treatment levels of cleaved cell surface receptor IBR, or cell surface receptor IBR at the surface of a cell, in cancer cells or tissues may be used to diagnose cancer in a subject or assess the effectiveness of treatment in a cancer patient. In a preferred embodiment the cell surface receptor is MUC1.

Comparison of the levels of the above-mentioned regions with levels from subjects known to be free of cancer may allow determination of the presence of cancer in the subject. An example, although not intended to be limiting, is that a determination of the presence of elevated levels of cleaved cell surface IBR in a sample from a subject, when compared to a level determined in samples from control subjects, may suggest the presence of cancer in the subject with elevated levels. Such methods of comparing levels of cancer-associated markers between a sample from a subject and a control sample for diagnostic purposes would be understood by one of ordinary skill in the medical arts. Examples of such methods include Western blotting, ELISA, antibody precipitation, PCR, LCR, rtPCR, cycling probe technology, and colloidal assays as described in international patent application serial no. PCT/US00/01997, filed Jan. 25, 2000, entitled "Rapid and Sensitive Detection of Aberrant Protein Aggregation in Neurodegenerative Diseases", published as no. WO 00/43791, and U.S. patent application Ser. No. 09/631,818, filed Aug. 3, 2000, entitled "Rapid and Sensitive Detection of Protein Aggregation", by Bamdad et al. In a preferred embodiment the cell surface receptor is MUC 1.

In another aspect of the invention, the cleavage state of MUC 1 can be used to determine progression or regression of a subject's cancer over time. The cleavage state also can be used to assess treatment parameters including, but not limited to: dosage, method of administration, timing of administration, and combination with other treatments as described herein.

Another aspect of the invention involves extremely early-stage cancer diagnosis. This aspect involves identification of patients who may be at risk for developing tumor or cancer associated with abnormal cleavage of MUC1. These patients may not have developed tumors, but may exhibit a cleavage state indicative of a condition that can lead to cancer. In some instances, the subjects will already be undergoing treatment for cancer, while in other instances the subjects will be without present cancer treatment. A test for a genetic predisposition to cancers characterized by aberrant MUC1 expression of the invention is based on detecting genetic alterations in the MUC1 cleavage enzyme(s), over expression of MUC1 activating ligands, and/or overexpression of enzymes that modify the MGFR portion of the receptor.

The fact that elevated levels of cleaved MUC1 are found in the blood of cancer patients is the basis for a blood test for breast cancer, which is not described herein. MUC1 is cleaved by at least one enzyme and may be cleaved at more than one site before it is released into the blood stream. Several protease cleavage sites within the MUC1 sequence are predicted. Predicted sites for enzyme cleavage are at or near amino acid 540, 528, 530, 542, and 550 (numbers are as listed in Andrew Spicer et al., J. Biol. Chem Vol 266 No. 23, 1991 pgs. 15099-15109; these amino acid numbers correspond to numbers 1100, 1088, 1090, 1102, 1110 of GENBANK® accession number P15941; PID G547937; Boshel M., et al, BBRC vol. 185 pgs 1-8; Hilkens J., et al, *Journal of Biological Chemistry* vol 267 pgs 6171-6177). The exact site of cleavage may vary depending on cell type or in response to a disease. The enzyme that cleaves MUC1 may be a membrane-associated enzyme, since the clustered IBRs of the MUC1 receptor limit access to the cleavage sites.

One aspect of the invention is the identification of compounds that directly bind to the PSMGFR portion of the receptor. Therefore, a sensitive method for diagnosing early tumors is to administer to the patient, compounds that bind to the PSMGFR region that have also been derivatized with contrast or imaging agents. These compounds will agglomerate onto tumors wherein this portion of the MUC1 receptor is accessible. Compounds described herein that bind to the PSMGFR region as well as other compounds that can be identified using methods of the invention can be readily modified to carry imaging agents. Such imaging agents may include but are not limited to, technetium, rhenium, $^{123}$I, and other contrast agents or radioactive entities commonly used in imaging techniques. Imaging techniques include but are not limited to single photon computed tomography (SPECT), MRI, microscopy and the like. In some applications, an attached colloid can act as an imaging agent. Since the carrier for the imaging agent can also be a therapeutic, this technique can combine an early diagnostic with a directed therapeutic.

As referred to previously, one aspect of the invention is directed to methods for treating a subject diagnosed with or at risk of developing a cancer or tumor characterized by the aberrant expression of MUC1. The treatments of the present invention involve the use of drugs or "agents" as described herein. That is, one aspect involves a series of compositions useful for treatment of cancer or tumor characterized by the aberrant expression of MUC1, including these compositions packaged in kits including instructions for use of the composition for the treatment of such conditions. That is, the kit can include a description of use of the composition for participation in any biological or chemical mechanism disclosed herein that is associated with cancer or tumor. The kit also can include instructions for use of a combination of two or more compositions of some embodiments of the invention. Instructions also may be provided for administering the drug orally, intravenously, or via another known route of drug delivery. These and other embodiments of the invention can also involve promotion of the treatment of cancer or tumor according to any of the techniques and compositions and combinations of compositions described herein.

In one set of embodiments, patients can be treated with compositions of the invention even though the patients exhibit indication for treatment of one of the compositions of the invention for a condition different from cancer or tumor, including conditions that can be unrelated to cell proliferation or conditions that can accompany cell proliferation, cancer, or tumor. That is, if a composition of the invention is known for treatment of a different condition, some embodiments of the present invention also involve use of that composition for treatments that accompany cell proliferation, cancer, or tumor disease where indicated. These and other embodiments of the invention can include such treatment where the dosage, delivery technique or vehicle, combination with other pharmaceutical compositions or lack of combination with other pharmaceutical compositions, rate of administration, timing of administration, or other factor differs from the use of the composition for treatment of the condition different from cell proliferation, cancer, or tumor. In another set of embodiments, treatment of cell proliferation, cancer, or tumor with compositions of the invention may occur under conditions that are similar to or overlap the use of compositions of the invention for treatment of a different condition, but the compositions of the invention are promoted for treatments that accompany cell proliferation, cancer, or tumor or includes instructions for treatments that accompany cell proliferation, cancer, or tumor as mentioned above. As used herein, "promoted" includes all methods of doing business including methods of education, hospital and other clinical instruction, pharmaceutical industry activity including pharmaceutical sales, and any advertising or other promotional activity including written, oral, and electronic communication of any form, associated with compositions of the invention in connection with treatments that accompany cell proliferation, cancer, or tumor. "Instructions" can and often do define a component of promotion, and typically involve written instructions on or associated with packaging of compositions of the invention. Instructions also can include any oral or electronic instructions provided in any manner. The "kit" typically, and preferably, defines a package including both any one or a combination of the compositions of the invention and the instructions, but can also include the composition of the invention and instructions of any form that are provided in connection with the composition in a manner such that a clinical professional will clearly recognize that the instructions are to be associated with the specific composition.

Subjects for whom certain treatment methods of the invention (with specific compositions directed toward cell proliferation, cancer, or tumor) are not intended are those who are diagnosed with a condition which may already call for treatment with the specific composition. Accordingly, one aspect of the invention involves treatment of cell proliferation, cancer, or tumor with a specific composition disclosed herein for that purpose, not in combination with another agent where the other agent has been taught previously for use in treatment of cell proliferation, cancer, or tumor itself. Another embodiment involves treatment of cell proliferation, cancer, or tumor with this specific composition alone, not in combination with any other active agent. Another embodiment involves treatment of cell proliferation, cancer, or tumor with this specific composition where the use of the composition in the treatment is specifically instructed (through, e.g. written instructions that can accompany the composition) for the treatment of cell proliferation, cancer, or tumor. In a preferred embodiment of this aspect, the invention involves treatment of cell proliferation, cancer, or tumor with the specific composition where the use of the composition in the treatment is specifically instructed to affect a mechanism associated with cell proliferation, cancer, or tumor as disclosed herein.

In yet another set of embodiments, the drugs and agents of the invention can be used for the purpose of disease prevention. In this context, the invention is particularly directed to a patient population never before treated with drugs useful according to certain methods of the invention, including patients who are not suffering from cell proliferation, cancer, or tumor and who may or may not be presently indicating susceptibility to cell proliferation, cancer, or tumor. In other words, the preventative treatment preferably is directed to patient populations that otherwise are free of disease symptoms that call for active treatment with any of the drugs described herein as useful according to the invention.

In one aspect, the invention involves the discovery that calcimycin, fusaric acid, L-α-methyl-dopa, butylindazone, NS1619 and etomoxir interrupt the interaction of MGFR with its ligand(s) that otherwise would bind to MGFR and promote tumorigenesis. In this aspect, the invention involves treatment of subjects associated with tumor or cancer associated with aberrant expression of MUC1 with these agents or a combination. These compounds were identified when a drug library was screened using the in vitro color change colloid aggregation assay described in Example 5a. These compounds were then tested in a whole cell assay to determine if they produced the desired activity, namely if they inhibited cell proliferation by interfering with the MGFR-ligand interaction. All of the compounds inhibited cell proliferation, but roughly half of the compounds were toxic to both tumor cells that presented the MUC1 receptor as well as cells that did not present this receptor. As discussed herein, the drug screen described in Example 5a does not differentiate among drugs that inhibit cell proliferation by: (a) binding to or otherwise blocking the activity of a MUC1-associated activating ligand(s), such as growth factors; b) directly binding to the MGFR portion of the MUC1 receptor and blocking its interaction with its activating ligands; or (c) inhibiting the activity of enzymes that modify the MGFR portion of the Muc1 receptor. Drugs that act according to the mode of action described in (a) will not be selective for MUC1-presenting cells and are likely to be somewhat cytotoxic since they inhibit essential growth factors. Drugs that act according to (b) and (c) will selectively inhibit the proliferation of MUC1-presenting cells and further, those that directly bind to the MGFR portion will have little or no toxic effects. Fusaric acid, L-α-methyl-dopa and etomoxir selectively inhibited proliferation of tumor cells presenting MUC1 while leaving control cells unaffected, see FIG. 13.

In one embodiment, the subject to be treated with the above agents can be otherwise free of signs, symptoms or evidence of disorders for which the agents of the invention would normally be or have previously been described. Preferably, the subject is otherwise free of symptoms calling for treatment involving the use of at least any one of calcimycin, fusaric acid, L-α-methyl-dopa, butylindazone, NS1619 and etomoxir, alone or in combination with each other or with other pharmaceutically acceptable substances. For example, calcimycin, fusaric acid, L-α-methyl-dopa, butylindazone, NS1619 and etomoxir may have been suggested for treatment of subjects having certain diseases; thus, in one embodiment, the preferred subjects are free of those disease for which the agents of the present invention have been previously prescribed.

Figure 3:
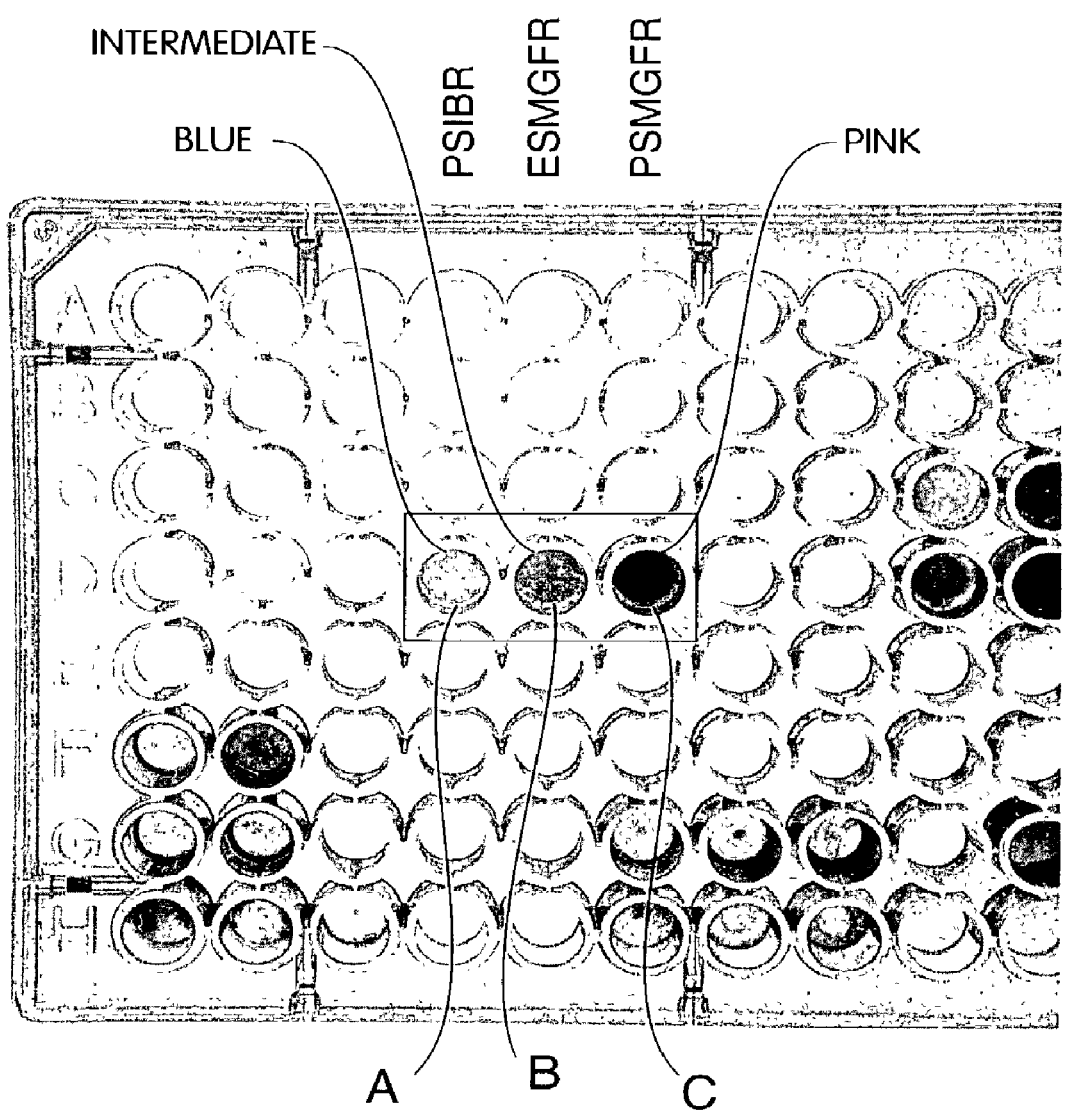
FIG. 3 is a black and white photocopy of an image from a colloid-based color change experiment in which the ability of peptides to self-aggregate was used to help determine a boundary between a portion of the MUC1 receptor that self-aggregates the cell-proximal portion that does not; results imply a disease-related cleavage site on the MUC1 receptor.

Fusaric acid. Subjects for whom the methods of the invention involving treatment with fusaric acid are not intended are those diagnosed with diseases which already call for treatment with fusaric acid, but where the call for treatment with fusaric acid did not specifically call for treatment directed toward tumors or cancers associated with the abherrant expression of MUC1, particularly in the dosages or other specific protocols described previously in U.S. Pat. No. 6,127,393. Specific diseases listed in U.S. Pat. No. 6,127,393 include skin cancer, breast cancer, prostate cancer, cervical cancer, colon cancer, liver cancer and lung cancer. In one embodiment, the methods of the present invention involve treatment with fusaric acid in dosages lower than that described in U.S. Pat. No. 6,127,393, as evidenced by graphs of FIG. 13 which are analogous to FIGS. 3A-3C in U.S. Pat. No. 6,127,393 which depict an amount of fusaric acid needed to inhibit cell growth.

In one embodiment, the invention provides a fusaric acid treatment in a lower dosage to provide a less than daily administration regimen. For example, the fusaric acid can be provided every other day or once weekly.

Etomoxir. Subjects for whom the methods of the invention involving treatment with etomoxir are not intended are those diagnosed with diseases which already call for treatment with etomoxir, particularly those subjects who have diseases associated with chronic heart failure calling for treatment with etomoxir. Such diseases include failing cardiac hypertrophy associated with an inadequate sarcoplasmic reticulum function.

NS1619. Although NS1619 is currently known as a biochemical tool as a K(ca) channel activator, subjects for whom the methods of the invention involving treatment with NS1619 are not intended are those diagnosed with diseases which already call for treatment with NS1619 requiring K(ca) channel modulation.

Calcimycin. Calcimycin is an ionophorous, polyether antibiotic from *streptomyces chartreusensis*. Calcimycin binds and transports cations across membranes and uncouples oxidative phosphorylation while inhibiting atpase of rat liver mitochondria. The substance is used mostly as a biochemical tool to study the role of divalent cations in various biological systems. Subjects for whom the methods of the invention involving treatment with calcimycin are not intended are those diagnosed with diseases which already call for treatment with calcimycin in this function.

Butylindazone. R(+)-butylindazone is a KCl cotransport inhibitor, and subjects for whom the methods of the invention involving treatment with butylindazone, specifically R(+)-butylindazone, are not intended are those diagnosed with diseases which already call for treatment with butylindazone requiring inhibition of KCl cotransport.

The method comprises administering to the subject calcimycin, fusaric acid, L-α-methyl-dopa, butylindazone, NS1619 and etomoxir in an amount effective to provide a medically desirable result. In one embodiment, the method comprises administering to the subject any one of calcimycin, fusaric acid, L-α-methyl-dopa, butylindazone, NS1619 and etomoxir in an amount effective to lower the risk/prevent/reduce/inhibit tumors or cancer associated with aberrant expression of MUC1.

The effective amount will vary with the particular condition being treated, the age and physical condition of the subject being treated, the severity of the condition, the duration of the treatment, the nature of the concurrent therapy (if any), the specific route of administration and like factors within the knowledge and expertise of the health practitioner. For example, in connection with tumor or cancer associated with abherrant expression of MUC1, an effective amount is that amount which prevents interaction of MGFR with its ligand that otherwise would promote cell proliferation (for agents that act according to that mechanism, including calcimycin, fusaric acid, L-α-methyl-dopa, butylindazone, NS1619 and etomoxir).

According to alternate mechanisms of drug activity, an effective amount is that amount which maintains self-aggregation of MUC1 receptors (for agents such as polymers or dendrimers that act according to that mechanism). Alternatively, an effective amount is one which reduces levels of cleaved MUC1 IBRs, or maintains low levels of cleaved MUC1 IBRs (for agents that act according to that mechanism). Likewise, an effective amount for treatment would be an amount sufficient to lessen or inhibit altogether the levels of cleaved MUC1 IBR (for agents that act according to that mechanism) so as to slow or halt the development of or the progression of tumor or cancer associated with aberrant expression of MUC1. It is preferred generally that a maximum dose be used, that is, the highest safe dose according to sound medical judgment When used therapeutically, the agents of the invention are administered in therapeutically effective amounts. In general, a therapeutically effective amount means that amount necessary to delay the onset of, inhibit the progression of, or halt altogether the particular condition being treated. Generally, a therapeutically effective amount will vary with the subject's age, condition, and sex, as well as the nature and extent of the disease in the subject, all of which can be determined by one of ordinary skill in the art. The dosage may be adjusted by the individual physician or veterinarian, particularly in the event of any complication. A therapeutically effective amount typically varies from 0.01 mg/kg to about 1000 mg/kg. It is expected that does ranging from 1-500 mg/kg, and preferably doses ranging from 1-50 mg/kg will be suitable. In other embodiments, the agents will be administered in doses ranging from 1 µg/kg/day to 10 mg/kg/day, with even more preferred doses ranging from 1-200 µg/kg/day, 1-100 µg/kg/day, 1-50 µg/kg/day or from 1-25 µg/kg/day. In other embodiments, dosages may range from about 0.1 mg/kg to about 200 mg/kg, and most preferably from about 0.2 mg/kg to about 20 mg/kg. These dosages can be applied in one or more dose administrations daily, for one or more days.

The agent of the invention should be administered for a length of time sufficient to provide either or both therapeutic and prophylactic benefit to the subject. Generally, the agent is administered for at least one day. In some instances, the agent may be administered for the remainder of the subject's life. The rate at which the agent is administered may vary depending upon the needs of the subject and the mode of administration. For example, it may be necessary in some instances to administer higher and more frequent doses of the agent to a subject for example during or immediately following a event associated with tumor or cancer, provided still that such doses achieve the medically desirable result. On the other hand, it may be desirable to administer lower doses in order to maintain the medically desirable result once it is achieved. In still other embodiments, the same dose of agent may be administered throughout the treatment period which as described herein may extend throughout the lifetime of the subject. The frequency of administration may vary depending upon the characteristics of the subject. The agent may be administered daily, every 2 days, every 3 days, every 4 days, every 5 days, every week, every 10 days, every 2 weeks, every month, or more, or any time there between as if such time was explicitly recited herein.

In one embodiment, daily doses of active compounds will be from about 0.01 milligrams/kg per day to 1000 milligrams/kg per day. It is expected that oral doses in the range of 50 to 500 milligrams/kg, in one or several administrations per day, will yield the desired results. Dosage may be adjusted appropriately to achieve desired drug levels, local or systemic, depending upon the mode of administration. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

Preferably, such agents are used in a dose, formulation and administration schedule which favor the activity of the agent and do not impact significantly, if at all, on normal cellular functions.

As noted, different drugs act according to different mechanisms. Drugs according to one mechanism interfere with MGFR binding to a tumorigenesis-promoting ligand, and do so to a particular degree relative to natural conditions for the subject in the absence of the drug. Drugs according to another mechanism reduce overall cleavage of MUC1, and do so to a particular degree relative to natural conditions for the subject in the absence of the drug. Drugs according to another mechanism maintain self-aggregation of MUC1 receptors, and do so to a particular degree relative to natural conditions for the subject in the absence of the drug. In one embodiment, the degree of activity of the drug is at least 10%. In other embodiments, the degree of activity of the drug is as least 20%, at least 30%, at least 40%, at least 50%, at least 60%, at least 70%, at least 80%, at least 90%, or at least 95%.

When administered to subjects for therapeutic purposes, the formulations of the invention are applied in pharmaceutically acceptable amounts and in pharmaceutically acceptable compositions. Such a pharmaceutical composition may include the agents of the invention in combination with any standard physiologically and/or pharmaceutically acceptable carriers which are known in the art. The compositions should be sterile and contain a therapeutically effective amount of the agent in a unit of weight or volume suitable for administration to a patient. The term "pharmaceutically-acceptable carrier" as used herein means one or more compatible solid or liquid filler, diluents or encapsulating substances which are suitable for administration into a human or other animal. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy. Pharmaceutically acceptable further means a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

Such preparations may routinely contain salts, buffering agents, preservatives, compatible carriers, and optionally other therapeutic ingredients. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulfonic, tartaric, citric, methane sulfonic, formic, malonic, succinic, naphthalene-2-sulfonic, and benzene sulfonic. Also, pharmaceutically acceptable salts can be prepared as alkaline metal or alkaline earth salts, such as sodium, potassium or calcium salts of the carboxylic acid group.

Suitable buffering agents include: acetic acid and a salt (1-2% W/V); citric acid and a salt (1-3% W/V); boric acid and a salt (0.5-2.5% W/V); and phosphoric acid and a salt (0.8-2% W/V).

Suitable preservatives include benzalkonium chloride (0.003-0.03% W/V); chlorobutanol (0.3-0.9% W/V); parabens (0.01-0.25% W/V) and thimerosal (0.004-0.02% W/V).

A variety of administration routes are available. The particular mode selected will depend, of course, upon the particular combination of drugs selected, the severity of the cancer condition being treated, the condition of the patient, and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, topical, nasal, other mucosal forms, direct injection, transdermal, sublingual or other routes. "Parenteral" routes include subcutaneous, intravenous, intramuscular, or infusion. Direct injection may be preferred for local delivery to the site of the cancer. Oral administration may be preferred for prophylactic treatment e.g., in a subject at risk of developing a cancer, because of the convenience to the patient as well as the dosing schedule.

Chemical/physical vectors may be used to deliver the agents of the invention to a target (e.g. cell) and facilitate uptake thereby. As used herein, a "chemical/physical vector" refers to a natural or synthetic molecule, other than those derived from bacteriological or viral sources, capable of delivering the agent of the invention to a target (e.g. cell).

A preferred chemical/physical vector of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2-4.0.mu. can encapsulate large macromolecules. RNA, DNA, and intact virions can be encapsulated within the aqueous interior and be delivered to cells in a biologically active form (Fraley, et al., Trends Biochem. Sci., v. 6, p. 77 (1981)). In order for a liposome to be an efficient gene transfer vector, one or more of the following characteristics should be present: (1) encapsulation of the gene of interest at high efficiency with retention of biological activity; (2) preferential and substantial binding to a target cell in comparison to non-target cells; (3) delivery of the aqueous contents of the vesicle to the target cell cytoplasm at high efficiency; and (4) accurate and effective expression of genetic information.

Liposomes may be targeted to a particular (e.g. tissue), such as (e.g. the vascular cell wall), by coupling the liposome to a specific ligand such as a monoclonal antibody, sugar, glycolipid, or protein.

Liposomes are commercially available from Gibco BRL, for example, as LIPOFECTIN™. and LIPOFECTACE™., which are formed of cationic lipids such as N-[1-(2,3 dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in Trends in Biotechnology, V. 3, p. 235-241 (1985).

In one particular embodiment, the preferred vehicle is a biocompatible micro particle or implant that is suitable for implantation into the mammalian recipient. Exemplary bioerodible implants that are useful in accordance with this method are described in PCT International application no. PCT/US/03307 (Publication No. WO 95/24929, entitled "Polymeric Gene Delivery System", claiming priority to U.S. patent application Ser. No. 213,668, filed Mar. 15, 1994).

PCT/US/0307 describes a biocompatible, preferably biodegradable polymeric matrix for containing an exogenous gene under the control of an appropriate promoter. The polymeric matrix is used to achieve sustained release of the exogenous gene in the patient. In accordance with the instant invention, the agent of the invention is encapsulated or dispersed within the biocompatible, preferably biodegradable polymeric matrix disclosed in PCT/US/03307. The polymeric matrix preferably is in the form of a micro particle such as a micro sphere (wherein the agent is dispersed throughout a solid polymeric matrix) or a microcapsule (wherein the agent is stored in the core of a polymeric shell). Other forms of the polymeric matrix for containing the agents of the invention include films, coatings, gels, implants, and stents. The size and composition of the polymeric matrix device is selected to result in favorable release kinetics in the tissue into which the matrix device is implanted. The size of the polymeric matrix devise further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the devise is administered to a vascular surface. The matrix composition also can be selected not to degrade, but rather, to release by diffusion over an extended period of time.

Both non-biodegradable and biodegradable polymeric matrices can be used to deliver agents of the invention of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multi-valent ions or other polymers.

In general, the agents of the invention are delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly (ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C P Pathak and J. A. Hubell in Macromolecules, 1993, 26, 581-587, the teachings of which are incorporated herein by reference, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate). Thus, the invention provides a composition of the above-described agents for use as a medicament, methods for preparing the medicament and methods for the sustained release of the medicament in vivo.

The compositions may conveniently be presented in unit dosage form and may be prepared by any of the methods well known in the art of pharmacy. All methods include the step of bringing the therapeutic agents into association with a carrier which constitutes one or more accessory ingredients. In general, the compositions are prepared by uniformly and intimately bringing the therapeutic agent into association with a liquid carrier, a finely divided solid carrier, or both, and then, if necessary, shaping the product.

Compositions suitable for parenteral administration conveniently comprise a sterile aqueous preparation of the therapeutic agent, which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono or di-glycerides. In addition, fatty acids such as oleic acid find use in the preparation of injectables. Carrier formulations suitable for oral, subcutaneous, intravenous, intramuscular, etc. can be found in Remington's Pharmaceutical Sciences, Mack Publishing Company, Easton, Pa.

Compositions suitable for oral administration may be presented as discrete units such as capsules, cachets, tablets, or lozenges, each containing a predetermined amount of the therapeutic agent. Other compositions include suspensions in aqueous liquors or non-aqueous liquids such as a syrup, an elixir, or an emulsion.

Other delivery systems can include time-release, delayed release or sustained release delivery systems. Such systems can avoid repeated administrations of the therapeutic agent of the invention, increasing convenience to the subject and the physician. Many types of release delivery systems are available and known to those of ordinary skill in the art. They include polymer based systems such as polylactic and polyglycolic acid, poly(lactide-glycolide), copolyoxalates, polyanhydrides, polyesteramides, polyorthoesters, polyhydroxybutyric acid, and polycaprolactone. Microcapsules of the foregoing polymers containing drugs are described in, for example, U.S. Pat. No. 5,075,109. Nonpolymer systems that are lipids including sterols such as cholesterol, cholesterol esters and fatty acids or neutral fats such as mono-, di- and tri-glycerides; liposomes; phospholipids; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment of established cancer conditions as well as subjects at risk of developing a cancer. "Long-term" release, as used herein, means that the implant is constructed and arranged to deliver therapeutic levels of the active ingredient for at least 7 days, and preferably 30-60 days. The implant may be positioned at the site of the tumor. Long-term sustained release implants are well known to those of ordinary skill in the art and include some of the release systems described above.

The therapeutic agent may be administered in alone or in combination with an anti-cancer drug. If the therapeutic agent is administered in combination the compounds may be administered by the same method, e.g. intravenous, oral, etc. or may be administered separately by different modes, e.g. therapeutic agent administered orally, anti-cancer drug administered intravenously, etc. In one embodiment of the invention the therapeutic agent and the anti-cancer drug are co-administered intravenously. In another embodiment the therapeutic agent and the anti-cancer drug are administered separately.

Anti-cancer drugs that can be co-administered with the compounds of the invention include, but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-Ia; Interferon Gamma- Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; TAXOL®; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division).

TABLE 1

Peptide sequences:

Histidine-Tagged Truncated receptor (His-TR):
(SEQ ID NO: 1)
GTINVHDVETQFNQYKTEAASPYNLTISDVSVSHHHHHH Histidine-Tagged Primary Sequence of the MUC1
Growth Factor Receptor (His-PSMGFR):
(SEQ ID NO: 2)
GTINVHDVETQFNQYKTEAASPYNLTISDVSVSDVPFPFSAQSGAHHHHHH Histidine-Tagged Extended Sequence of MUC1
Growth Factor Receptor (ESMGFR)
(SEQ ID NO: 3)
VQLTLAFREGTINVHDVETQFNQYKTEAASPYNLTISDVSVS
DVPFPFHHHHHH Histidine-Tagged Primary Sequence of the
Interchain binding Region (His-PSIBR):
(SEQ ID NO: 4)

TABLE 1-continued

Peptide sequences:

HHHHHHGFLGLSNIKFRPGSVVVQLTLAFRE

Histidine-Tagged Repeat Motif 2 (His-RM2):
(SEQ ID NO: 5)
PDTRPAPGSTAPPAHGVTSAPDTRPAPGSTAPPAHGVTSAHHHHHH Truncated receptor (TR):
(SEQ ID NO: 6)
GTINVHDVETQFNQYKTEAASPYNLTISDVSVS Primary Sequence of the MUC1 Growth Factor
Receptor (PSMGFR):
(SEQ ID NO: 7)
GTINVHDVETQFNQYKTEAASPYNLTISDVSVSDVPFPFSAQSGA Primary Sequence of the Interchain Binding Region)
(PSIBR):
(SEQ ID NO: 8)
GFLGLSNIKFRPGSVVVQLTLAFRE Repeat Motif 2 (RM2):
(SEQ ID NO: 9)
PDTRPAPGSTAPPAHGVTSAPDTRPAPGSTAPPAHGVTSA MUC1 Receptor
(Mucin 1 precursor, GENBANK ® Accession number:
P15941
(SEQ ID NO: 10)
MTPGTQSPFF LLLLLTVLTV VTGSGHASST PGGEKETSAT
QRSSVPSSTE KNAVSMTSSV LSSHSPGSGS STTQGQDVTL
APATEPASGS AATWGQDVTS VPVTRPALGS TTPPAHDVTS
APDNKPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDTRPAPGS TAPPAHGVTS
APDTRPAPGS TAPPAHGVTS APDNRPALGS TAPPVHNVTS
ASGSASGSAS TLVHNGTSAR ATTTPASKST PFSIPSHHSD
TPTTLASHST KTDASSTHHS SVPPLTSSNH STSPQLSTGV
SFFFLSFHIS NLQFNSSLED PSTDYYQELQ RDISEMFLQI
YKQGGFLGLS NIKFRPGSVV VQLTLAFREG TINVHDVETQ
FNQYKTEAAS RYNLTISDVS VSDVPFPFSA QSGAGVPGWG
IALLVLVCVL VALAIVYLIA LAVCQCRRKN YGQLDIFPAR
DTYHPMSEYP TYHTHGRYVP PSSTDRSPYE KVSAGNGGSS
LSYTNPAVAA ASANL Proopiomelanocortin (adrenocorticotropin/beta-
lipotropin/alpha-melanocyte stimulating hormone/
beta-melanocyte stimulating hormone/beta-
endorphin) [Homo sapiens].
Accession number: XP_002485
(SEQ ID NO: 11)
AAAKEGKKSR DRERPPSVPA LREQPPETEP QPAWKMPRSC
CSRSGALLLA LLLQASMEVR GWCLESSQCQ DLTTESNLLE
CIRACKPDLS AETPMFPGNG DEQPLTENPR KYVMGHFRWD
RFGRRNSSSS GSSGAGQKRE DVSAGEDCGP LPEGGPEPRS
DGAKPGPREG KRSYSMEHFR WGKPVGKKRR PVKVYPNGAE

TABLE 1-continued

Peptide sequences:

DESAEAFPLE FKRELTGQRL REGDGPDGPA DDGAGAQADL
EHSLLVAAEK KDEGPYRMEH FRWGSPPKDK RYGGFMTSEK
SQTPLVTLFK NAIIKNAYKK
GE (SEQ ID NO: 12)
RGDHHHHHHSSSSGSSSSGSSSSGGRGDSGRGDS

The function and advantage of these and other embodiments of the present invention will be more fully understood from the examples below. The following examples are intended to illustrate the benefits of the present invention, but do not exemplify the full scope of the invention.

EXAMPLES

Colloid Preparation/Drug Screening Methods Employed in the Examples

In certain examples and embodiments of the invention, use is made of self-assembled monolayers (SAMs) on surfaces of colloid particles. Colloids were derivatized with SAMs and prepared for drug screening in a manner similar to that described in International Patent Publication No. WO 00/43791, published Jul. 27, 2000, entitled "Rapid and Sensitive Detection of Aberrant Protein Aggregation in Neurodegenerative Diseases", incorporated herein by reference.

In a typical example, 1.5 ml of commercially available gold colloid (Auro Dye by Amersham) were pelleted by centrifugation in a microfuge on high for 10 minutes. The pellet was resuspended in 100 µL of the storage buffer (sodium citrate and tween-20). 100 µL of a dimethyl formamide (DMF) solution containing thiols. Following a 3-hour incubation in the thiol solution, the colloids were pelleted and the supernatant discarded. They were then heat cycled in 100 µL of 400 µM tri-ethylene glycol-terminated thiol in DMF for 2 minutes at 55° C., 2 minutes at 37° C., 1 minute at 55° C., 2 minutes at 37° C., then room temperature for 10 minutes. Heat cycling results in the elimination of any species that are not in the lowest energy confirmation, resulting in a stable, close-packed, self-assembled monolayer. Heat cycling can be carried out with any of a wide variety of self-assembled monolayer-forming species. The colloids were then pelleted and 100 µL 100 mM NaCl phosphate buffer were added. The colloids were then diluted 1:1 with 180 µM $NiSO_4$ in the colloid storage buffer.

Thiols used in coating colloids typically were derived from solutions containing about 40 µM nitrilo tri-acetic acid (NTA)-thiol, and other thiols such as methyl-terminated thiol (HS—(CH2)15 CH3), 40% tri-ethylene glycol-terminated thiol, $HS(CH_2)_{11}(CH_2CH2)_3OH$, (formula) and 50% poly (ethynylphenyl) thiol ($C_{16}H_{10}S$). Different thiols were used to selectively inhibit non-specific binding optimally.

Colloid aggregation can be sensitively detected by monitoring color change of colloid particles which are initially disperse in suspension. Aggregation results in a color change to blue. No auxiliary signaling entity is necessary. In drug screening, aggregation (or lack thereof) is observed in the presence of candidate drugs.

Example 1a

Determination of Self-Aggregation of PSIBR Peptide of MUC1

Figure 2:
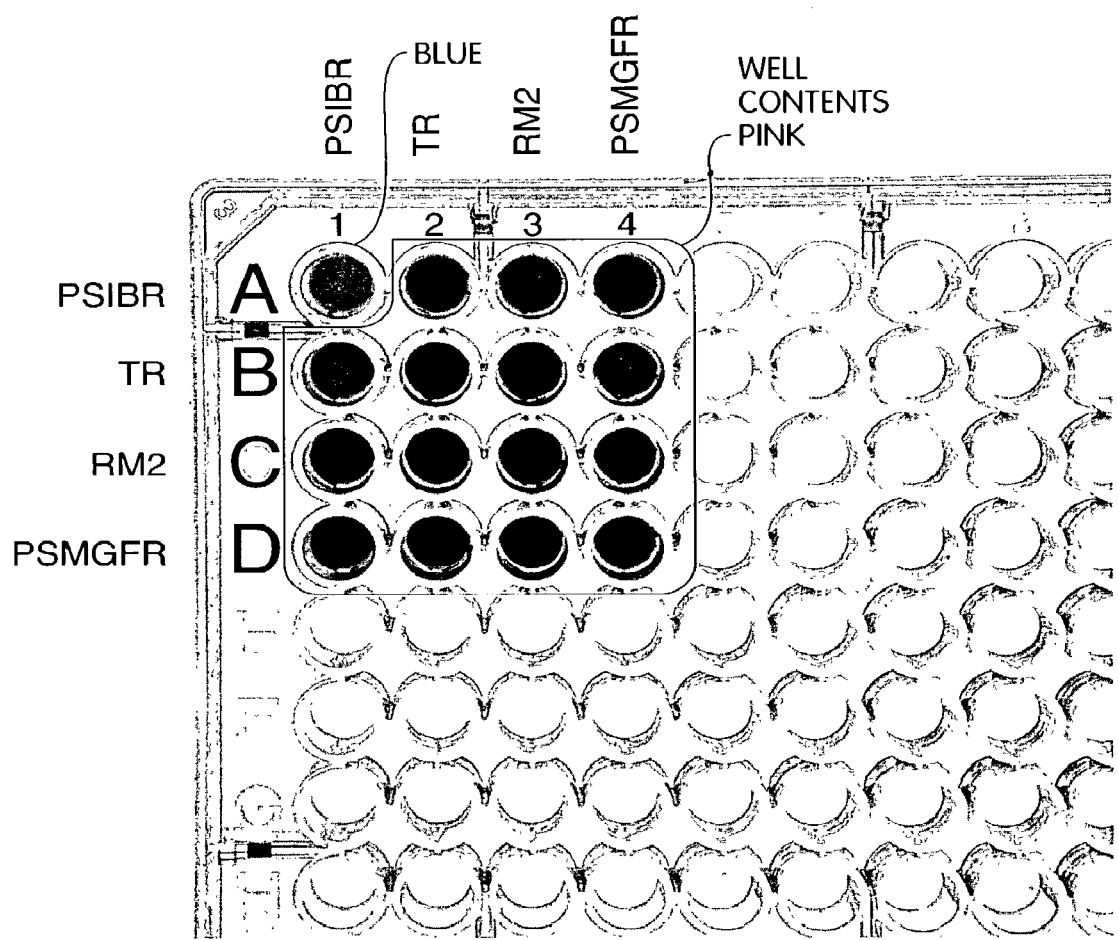
FIG. 2 is a black and white photocopy of an image from a colloid-based, color change binding experiment that shows which portions of soluble MUC1 bind to each other or self-aggregate.

The following experiment was designed to challenge the hypothesis proposed by others that a cleaved portion of the MUC1 receptor becomes the ligand for that portion of the receptor that remains attached to the cell surface after shedding. However, surprising results indicate that a portion of the MUC1 receptor, close to the cell surface, self-aggregates in a high affinity interaction, see FIG. 2. In FIG. 2, all wells of Row A, columns 1-4 and Column 1, rows A-D turned blue within a few minutes, while the remaining 9 wells (rows B-D, columns 2-4) remained pink. This experiment tested various fragments of the MUC1 receptor for their ability to bind to each other or to themselves (self-aggregate). Results show that none of the fragments bind to other portions of the receptor. However, a portion defined at least in part by the sequence of the PSIBR peptide (Table 1) self-aggregates in a high affinity interaction. We termed this region the IBR (interchain binding region) of the receptor.

Histidine-tagged peptides were synthesized with the sequences shown in table 1 (the various regions of MUC1). The lyophilized peptides were dissolved in DMSO to give a final concentration of 5 mM. A stock solution of each peptide was made by dissolving 4 µl 5 mM DMSO stock in 196 µl Phosphate-Buffered-Saline (PBS) for a resulting concentration of 100 µM. 20 µl of each 100 µM peptide solution was added to 100 µl colloids presenting NTA-Ni to capture the histidine tag of the peptides. The colloids were incubated with the histidine-tagged peptides at room temperature for 10 minutes to allow binding of the histidine-tags to the NTA-Ni on the surface of the colloids. 20 µl aliquots of each peptides species on colloids was then mixed with 20 µl of every other peptide species and with 60 µl of phosphate buffer pH 7.4. The color change of the colloid solutions was recorded after 15 minutes, see FIG. 2. Row A contains the His-PSIBR (primary sequence interchain binding region) peptide; Row B contains the His-TR peptide; Row C contains the His-RM2 peptide; Row D contains the His-PSMGFR peptide. Column 1 contains the His-PSIBR peptide; Column 2 contains the His-TR peptide; Column 3 contains the His-RM2 peptide; and Column 4 contains the His-PSMGFR peptide. The solutions were observed for a color change. A change in solution color from pink to blue indicates that the colloids have been forced together by a binding interaction. During this period, the set of colloids incubated with the His-PSIBR peptide changed color from pink to blue. Only the well of Row A, Column 1, which is the cross section of PSIBR with itself, turned from pink to blue within the first 10 minutes. Results show that none of the receptor fragments bind to other portions of the receptor, but importantly, one region which we term the primary sequence of the interchain binding region (PSIBR), self-aggregates in a high affinity interaction, suggesting a mechanism by which the MUC1 receptor confers tumorigenesis.

No color changes were observed in wells that did not contain PSIBR, indicating that the other peptide portions of MUC1 do not interact with one another. However, after an hour-long incubation period, solutions that contained PSIBR and any other peptide, which included MUC1-derived peptides as well as control peptides, turned purple, presumably due to self-aggregation of the PSIBR, which was somewhat inhibited due to the presence of irrelevant peptides.

The colloid sets were centrifuged to form a pellet and were resuspended in phosphate buffer. The PSIBR-peptide-bound colloids would not resuspend in buffer, indicating that the binding interaction that had forced the colloids together was a tight interaction. Since there was only one peptide species on the colloids, the binding interaction must be the PSIBR peptide binding to itself. The other sets of colloids bound to peptides were assayed for their interaction with one another by mixing 15 µl of one colloid type with 15 µl of a second colloid type and 70 µl phosphate buffer.

Example 1b

Relationship Between MUC1 Cleavage Site in Tumor Conditions and MUC1 Interchain Binding This example investigates the ability of peptide sequences near the boundary between the MGFR and PSIBR of the MUC1 receptor to participate in self-aggregation, and thereby elucidates a probable cleavage site of MUC1 that is associated with tumorigenesis or cancer.

A histidine-tagged peptide (ESMGFR) whose sequence contained all of the amino acids in the His-PSMGFR peptide plus 9 additional amino acids from the PSIBR region, adjacent to the PSMGFR, were added to the N-terminus of the peptide. N-terminus-VQLTLAFREGTINVHDVETQFN-QYKTEAASPYNLTISDVSVSDVPFPFHHHHHH (SEQ ID NO:3)-C-terminus.

The peptide was attached to colloid particles presenting NTA thiols, as in other experiments described herein. The colloid-immobilized ESMGFR peptides self-aggregated, which caused the colloid solution to change color (from pink toward blue, see well B of FIG. 3, which has changed from pink to blue). However, the extent of color change, which indicates the extent of particle-immobilized peptide aggregation, was not nearly as dramatic as in identical experiments in which the colloid-immobilized His-PSIBR peptide was allowed to self-aggregate (well A of FIG. 3—blue), demonstrating some self-aggregation when a portion of the IBR region was attached to the non-aggregating His-PSMGFR peptide. The His-PSMGFR peptide sequence was demonstrated to be completely free of self-aggregation. Specifically, the His-PSMGFR peptide was fastened to colloid particles and in an aggregation assay was shown not to self-aggregate (well C of FIG. 3—pink).

This strongly suggests that cleavage of the MUC1 receptor in tumors or cancers associated with aberrant expression of MUC1 occurs at or near the boundary between the PSMGFR and PSIBR sequences, since it is demonstrated herein that in tumor cells that overexpress MUC1, the MGFR is accessible by agents that reduce cell proliferation by inhibiting the interaction between MGFR and ligands that could be growth factors, and that otherwise would promote cell proliferation. This also strongly suggests that the IBR is shed in cleavage of MUC1 receptor in tumor or cancer associated with aberrant expression of MUC1, but is not shed in cleavage of MUC1 when MUC1 is normally expressed in healthy cells. That is, that the cleavage site of MUC1 is at or near the C-terminal boundary of the IBR in tumor or cancer cells and IBR at or near the N-terminal boundary of the IBR in healthy cells.

In the remaining examples, the mechanism described above for cancer associated with aberrant expression of MUC1, in which an activating ligand (which is a growth factor) binds to multiple MGFRs at a cell surface and thereby triggers a signal within the cell which causes proliferation (inductive multimerization), is confirmed. Briefly, the mechanism is confirmed by showing that exposure of cells to a bivalent antibody raised against MGFR induces cell proliferation characterized by a growth/response curve typical of a growth factor/receptor-antibody response (Example 2, below); the activating ligand produced by MUC1-presenting cells binds multiple PSMGFRs, and the amount of activating ligand produced by each cell type is proportional to the amount of MUC1 receptor produced by that cell type (Example 3a-b, below); MUC1 tumor cells produce a species that is a multimer (Example 4b, below); and drugs found to be specific for MUC1 tumor cells (drugs that inhibit proliferation in MUC1 tumor cells but not other cells) are shown to bind to MGFR at cells, while those that are not specific (those that inhibit MUC1 tumor cells and other cells) are toxic in that they bind to the multimeric ligand and thereby remove it from interaction with the cells (Example 5b2, below).

Example 2

Dimerization of the MGFR Portion of the MUC1 Receptor Triggers Enhanced Cell Proliferation Consistent with the Mechanism Presented for MUC1 Tumor Cells This example demonstrates the effect of dimerization on the MUC1 receptor. In this example it is shown that exposure of cells to a bivalent antibody grown against the MGFR region of the MUC1 receptor, at varying concentration, results in enhanced cell proliferation (or lack thereof) consistent with the mechanism presented for MUC1 tumor cells. A bivalent antibody was raised against PSMGFR (i.e., a single antibody having the ability to bind simultaneously to two MGFRs was produced). MUC1 tumor cells (T47Ds) were exposed to this antibody, and cell proliferation was studied as a function of concentration of the antibody. A growth/response curve typical of a growth factor/receptor-antibody response was observed. Specifically, at concentration low enough that only a small portion of the cells were exposed to the antibody, cell proliferation was low. At a concentration of antibody high enough that one antibody could bind adjacent MGFRs, cell proliferation was maximized. At a high excess of antibody, each antibody bound only a single MGFR, rather than dimerizing adjacent MGFRs, and proliferation was reduced.

Figure 4:
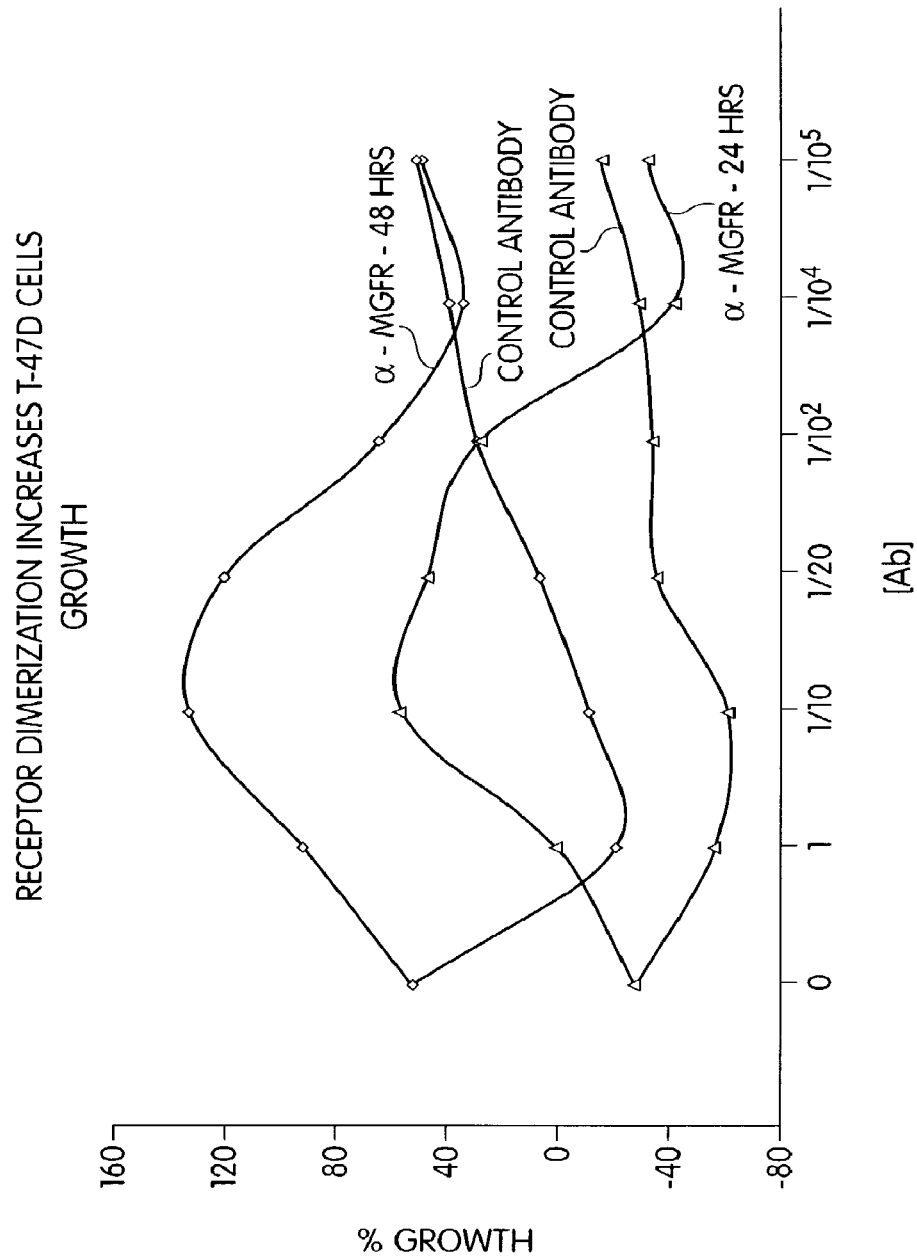
FIG. 4 is a graph of percent cell proliferation that shows that an antibody against an epitope of the MUC1 receptor which is proximal to the cell surface, and that dimerizes the receptor, enhances cell proliferation in a manner typical of a growth factor/receptor-antibody interaction.

T47D (HTB-133) cells, a human breast cancer cell line that overexpresses MUC1, were cultured to 30% confluency. An antibody raised against the PSMGFR portion of the MUC1 receptor, i.e. an antibody to the MFGR (Zymed, San Francisco, Calif., USA), was added to cells at varying concentrations in a multi-well cell culture plate. As a negative control, a second set of T47D cells was treated with an irrelevant antibody (anti-streptavidin). Prior to adding antibody, cells were counted (at time zero). All experiments were performed in triplicate. Cells were allowed to grow in a $CO_2$ incubator under normal conditions. Cells were counted using a hemacytometer (3 counts per well) at 24 hours and again at 48 hours. Results, see FIG. 4, show that in a concentration-dependent manner, addition of antibody caused enhanced cell proliferation compared to the proliferation of the same cells treated with a control antibody. FIG. 4 is a graph in which measured cell growth at 24 and 48 hours is plotted as a function of anti-PSMGFR concentration. At the optimal antibody concentration, when presumably one antibody binds bivalently to two MGFR portions of the MUC1 receptor, i.e. dimerizes the receptor, cell proliferation is at a maximum.

Figure 5:
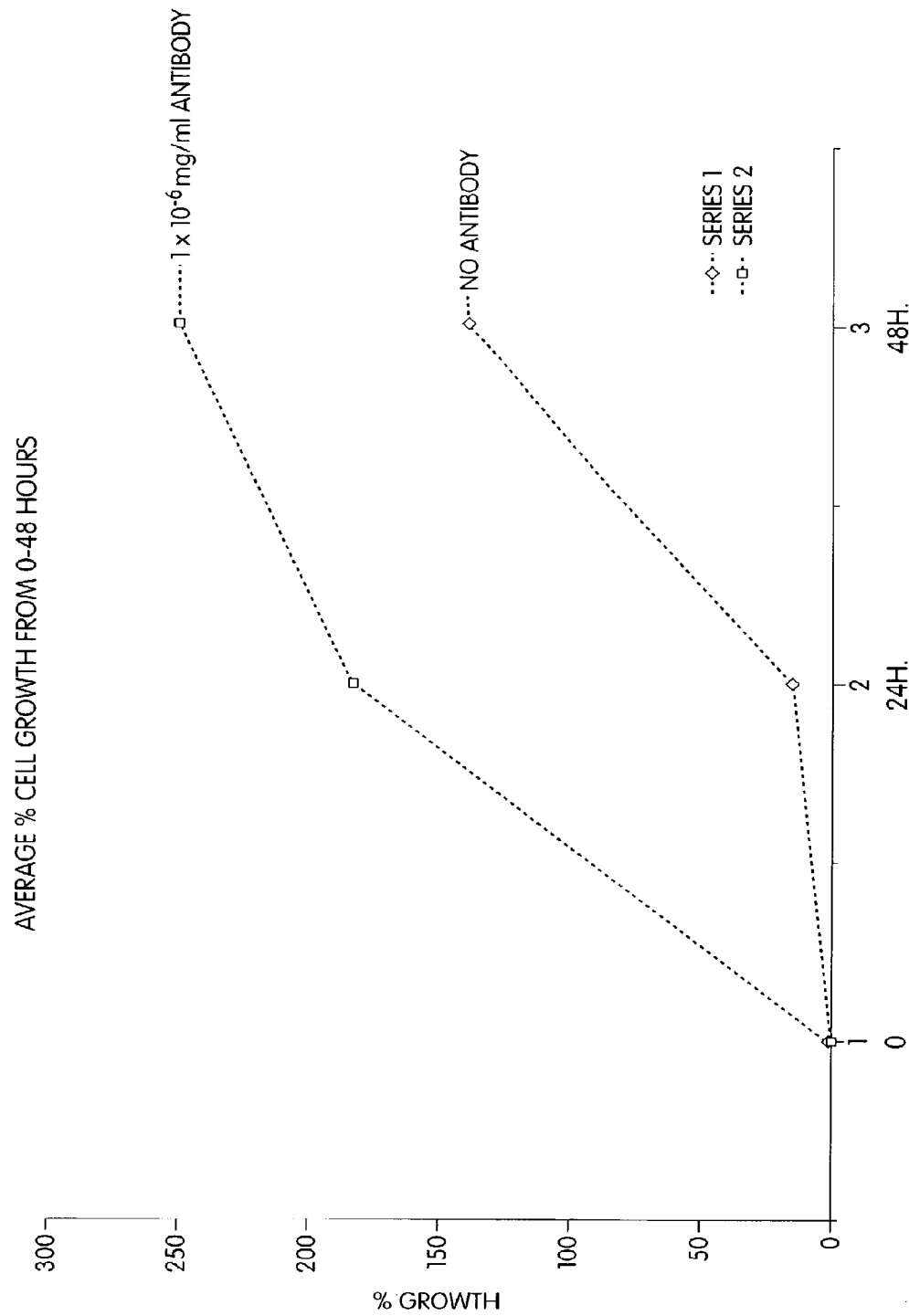
FIG. 5 is a graph of percent cell proliferation that shows that an antibody against an epitope of the MUC1 receptor which is proximal to the cell surface, and that dimerizes the receptor, dramatically enhances cell proliferation.

In a similar experiment, a concentration of the anti-PSMGFR antibody, identified to maximize cell proliferation, was added to a first group of T47D tumor cells, grown as described above. The same amount of the anti-PSMGFR antibody was added to a set of control cells, K293 cells. FIG. 5 shows that the addition of the anti-PSMGFR antibody to MUC1 tumor cells (T47D) enhanced proliferation by 180% 24 hours, but had no effect on the control cells. The growth of the T47D cells plateaued to saturation, for cells with added antibody, at 48 hours. Control cells never reached saturation within the time frame of the experiment and were at 70% confluency at 48 hours.

Example 3a

The Activating Ligand Produced by MUC1-Presenting Cells Binds Multiple PSMGFRs In this example, it is demonstrated that the activating ligand that triggers MUC1 tumor cell proliferation binds multiple PSMGFRs simultaneously. Colloid particles were produced that carry immobilized PSMGFRs, and suspensions of these colloids were exposed to lysate and supernatants of (1) MUC1 tumor cells, or (2) control cells. MUC1 tumor cell lysates/supernatants caused the colloids to aggregate (suspension turns blue) because the activating ligand contained in them binds MGFRs on different colloid particle, causing the colloid particles to aggregate. The control cell lysates/supernatants do not.

20 microliters of a 100 micro molar solution of the His-PSMGFR peptide, described in Table 1, were added to 100 microliters of colloids which were derivatized with a SAM including NTA-Nickel moieties to capture the histidine-tagged peptides. Lysates and supernatants from four different tumor-associated cell lines (HTB-133 (also called T47D), CRL-1500, CRL 1504 and CRL-1902; ATTC, American Type Culture Collection, Manasses, Va.) were added to aliquots of the peptide-presenting colloids. To each well of a 96-well plate, 30 uL of each lysate/supernatant was added to 40 uL of PBS, 30 ul of the His-PSMGFR-bearing or as a negative control, the GST-bearing colloids. A color change from pink to blue rapidly occurred for the two cell lines that overexpress the MUC1 receptor. A color change was observed for the CRL-1504 cells, which express MUC1, but after a much longer incubation period. No color change occurred for the cell line CRL-1902, which are not known to express the MUC1 receptor. As a negative control, the lysates were also added to colloids presenting an irrelevant peptide, the GST protein. As an additional negative control (data not shown), growth media for the different cell lines was added to colloid preparations. No color change was observed for the negative controls.

Figure 6:
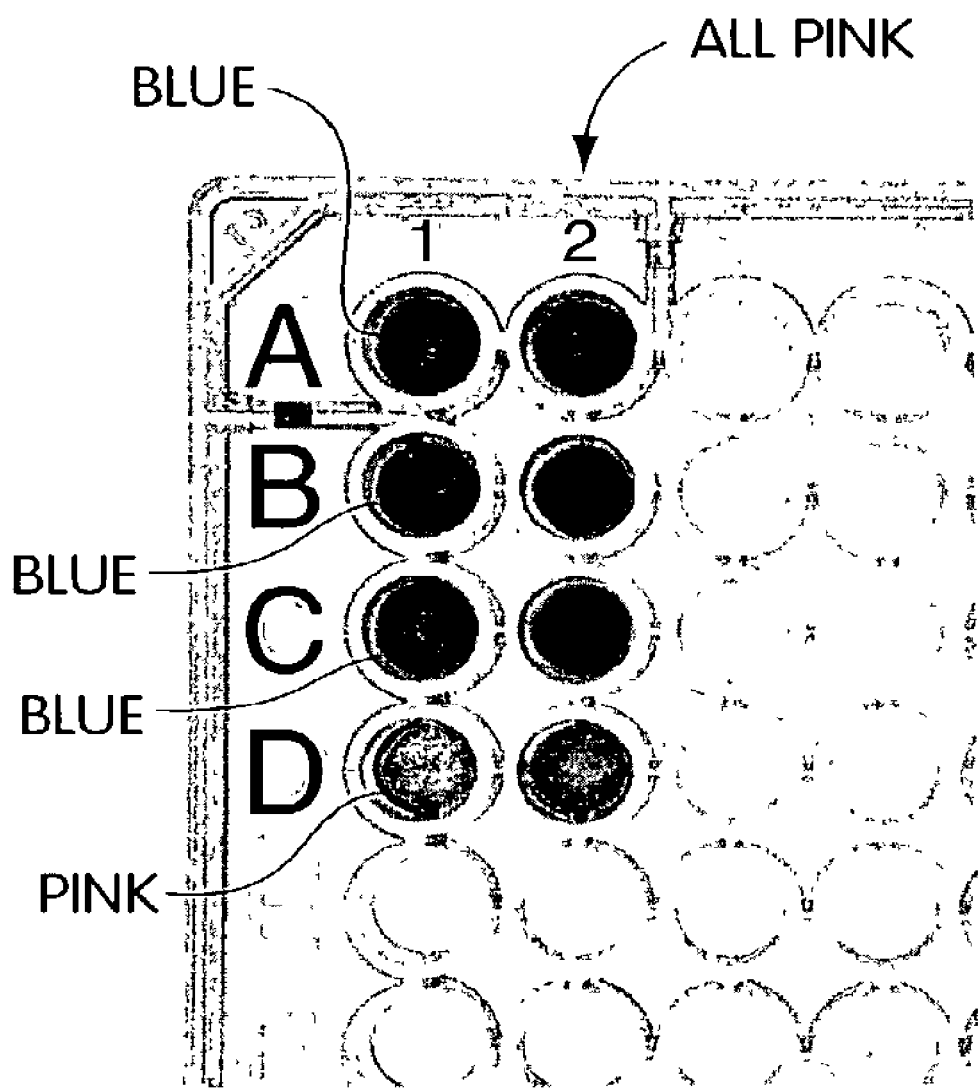
FIG. 6 is a black and white photocopy of an image of a section of a 96-well plate illustrating a color change assay in which a ligand(s) present in the lysates of cells that express MUC1, binds to and dimerize the His-PSMGFR peptide, derived from MUC1, which is immobilized on gold colloids, while lysates from cells that do not express MUC1 do not.

Results are shown in FIG. 6, which is an image of a section of a 96-well plate illustrating the colloid-based color change assay.

Referring still to FIG. 6, wells in Column 1 contain colloids bearing His-PSMGFR. Wells in Column 2 contain colloids bearing GST (glutathione-S-transferase) protein as a negative control. Row B: HTB-133 (also known as T47D) color change from pink to blue; Row C: CRL-1500 color change from pink to blue; Row A: CRL-1504 color change from pink to blue, but after a much longer incubation period; Row D: CRL-1902 no color change was produced. As a negative control, the lysate/supernatants were also added to colloids presenting an irrelevant peptide, the GST protein, but no color change was observed for any cell line.

Figure 7:
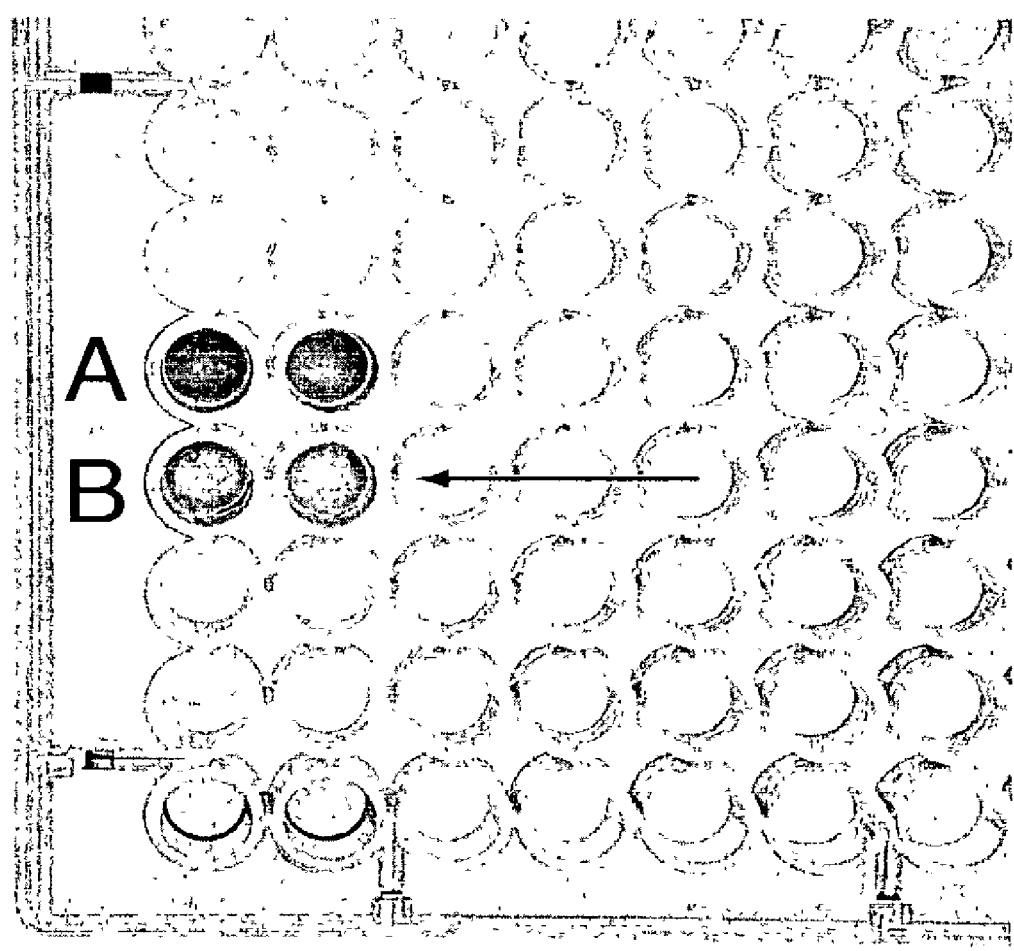
FIG. 7 is a black and white photocopy of an image of 96-well plate illustrating a colloid-based color-change binding assay between a MUC1-derived peptide and a ligand(s) present in a crude cell lysate; addition of imidazole, which releases the probe peptide from the colloid, causes a reversal of the color change, which argues that the color change is the result of a specific interaction rather than random colloid aggregation.

The results of FIG. 7 argue that this is a specific interaction between the PSMGFR peptide and a ligand(s) rather than random precipitation of colloids. FIG. 7 is an image of 96-well plate illustrating a colloid-based color-change binding assay between the His-PSMGFR, MUC1-derived peptide and a ligand(s) present in a crude cell lysate. The addition of imidazole, which releases the histidine-tagged probe peptide from the NTA moiety on the colloid, caused a reversal of the color change, which argues that the color change is the result of a specific interaction rather than random colloid aggregation. Addition of a ligand present in a crude cell lysate of T47D cells, which may be a dimer under these conditions, to the peptide-presenting colloid solutions, caused the solution to turn blue, see FIG. 7 Row B, (at arrow). A drug candidate that disrupts the peptide-ligand interaction will cause the solution to remain or revert to pink. In this way, high throughput drug screening is achieved and may also be automated by analyzing color change on a spectrophotometer.

These results indicate that cell lines HTB-133 (T47D) and CRL-1500 secrete high levels of the ligand for the MUC1 receptor and that the ligand acts to dimerize or multimerize the receptor.

Example 3b

Relationship Between Degree of Expression of MUC1 in Cell Lines and Presence of Ligand that Interacts with PSMGFR In this example, it was shown that there is a direct correlation between the expression of MUC1 and the presence of a ligand or ligands that binds to a peptide derived from the portion of the MUC1 receptor that is directly adjacent to the cell surface (MGFR).

Colloid particles carrying immobilized PSMGFR (His-PSMGFR linked to NTA-presenting thiols in SAMs on the colloids) were observed for their aggregation potential (color change from pink to blue in suspension) upon exposure to lysates from various cells lines know to overexpress, express, or not express MUC1. HTB-133, CRL-1500, CRL-1504, and CRL-1902 lines were studied. Lysates from a cell line that overexpresses MUC1 (HTB-133) caused colloid suspensions to turn blue within 15 minutes, indicating a high concentration of a ligand(s) in the lysate that interacts with the colloid-immobilized MGFR-derived peptides. Lysates from cell lines that express, but do not overexpresses, MUC1 (CRL-1500 and CRL-1504) caused colloid suspensions to turn blue within 3 hours, indicating moderate concentration of ligand(s) in the lysate. Lysates from a cell line that is not known to express MUC 1 (CRL-1902) caused colloid suspensions to begin to turn blue only after 10 hours, indicating a low concentration of a ligand(s) in the lysate. Controls involved immobilized RGD peptide (which is not dimerized by components of these cell lysates). The control suspensions remained pink indefinitely, indicating no aggregation.

Figure 8A:
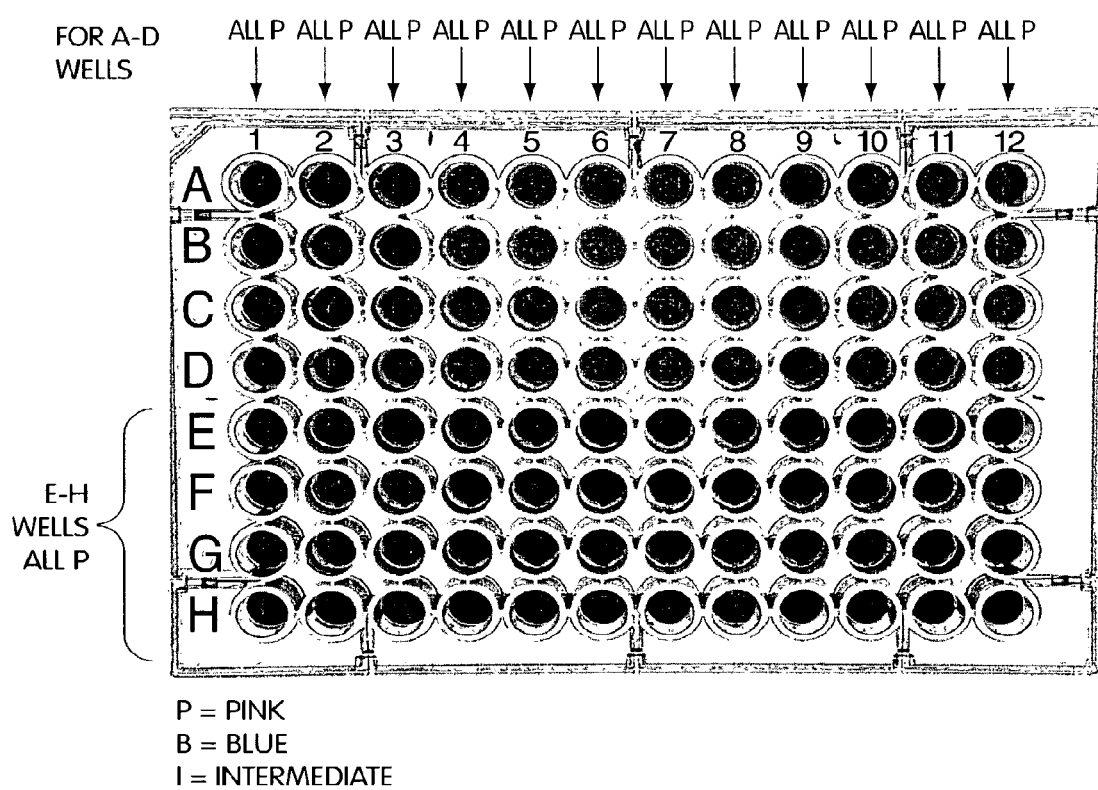
FIGS. 8A-D is a black and white photocopy of an image that shows a colloid-based color change assay in 96-well plates in which a ligand present in a cell lysate caused dimerization of a MUC1-derived peptide and that the degree of color change, which indicates an amount of ligand present, was a function of which cell line supplied the lysate.
Figure 8B:
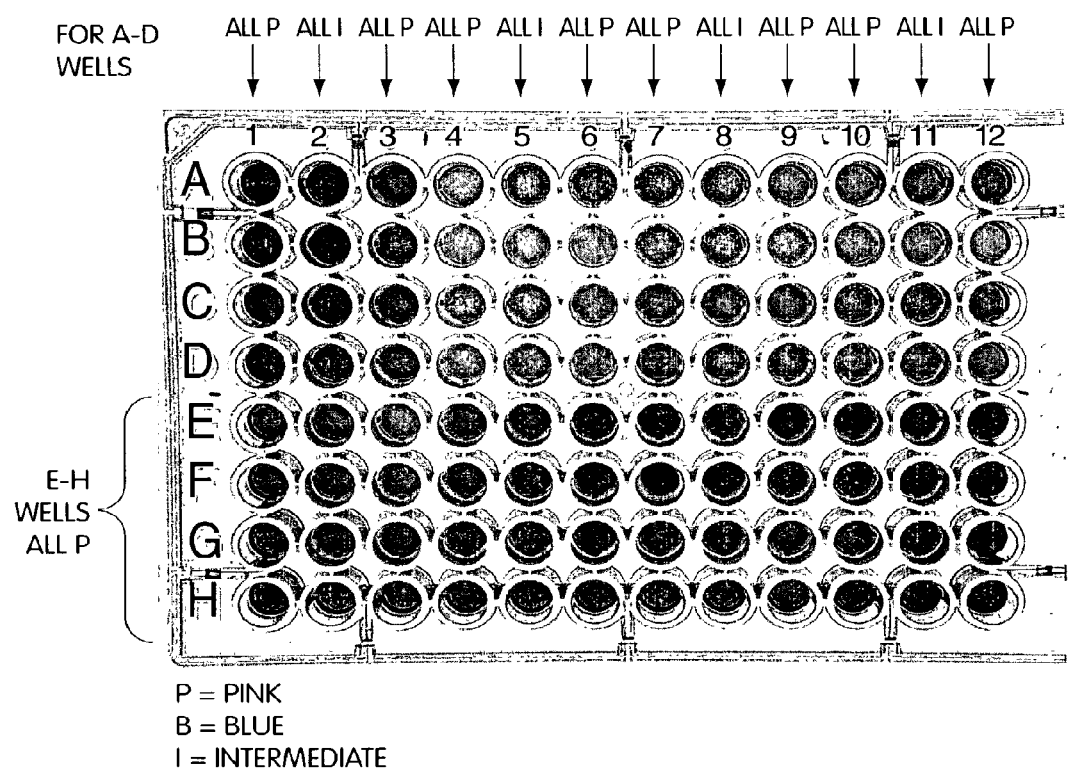
Figure 8C:
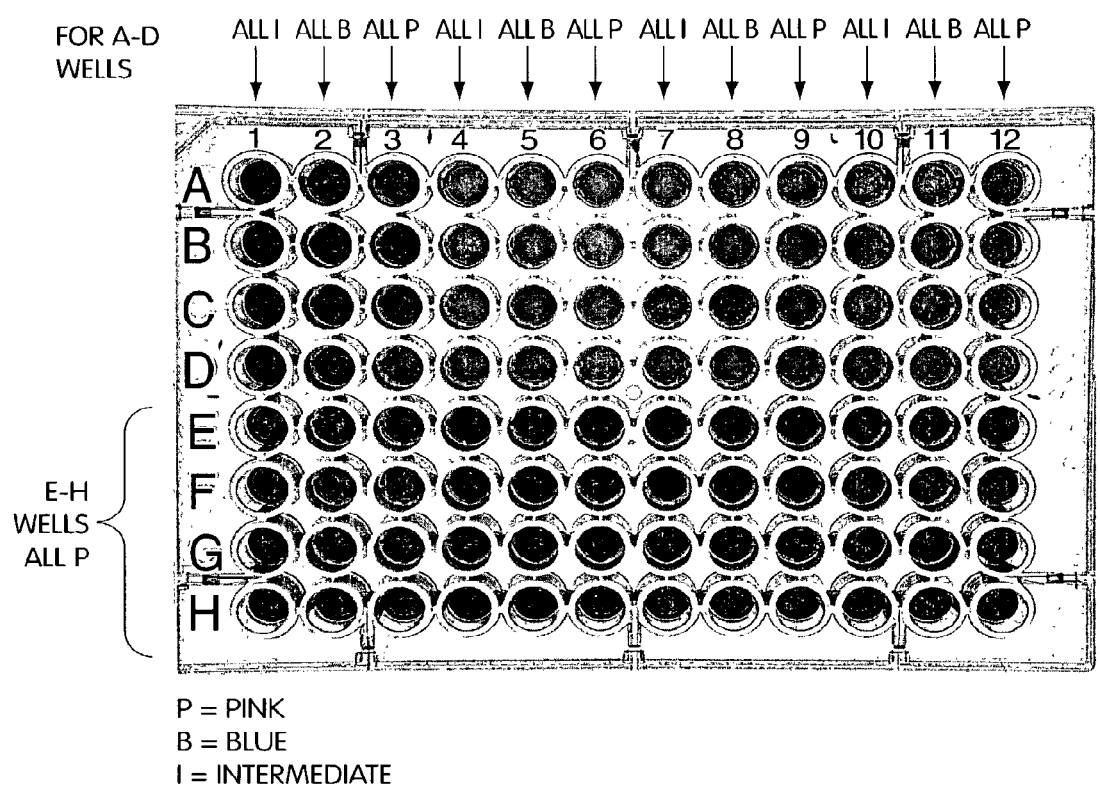
Figure 8D:
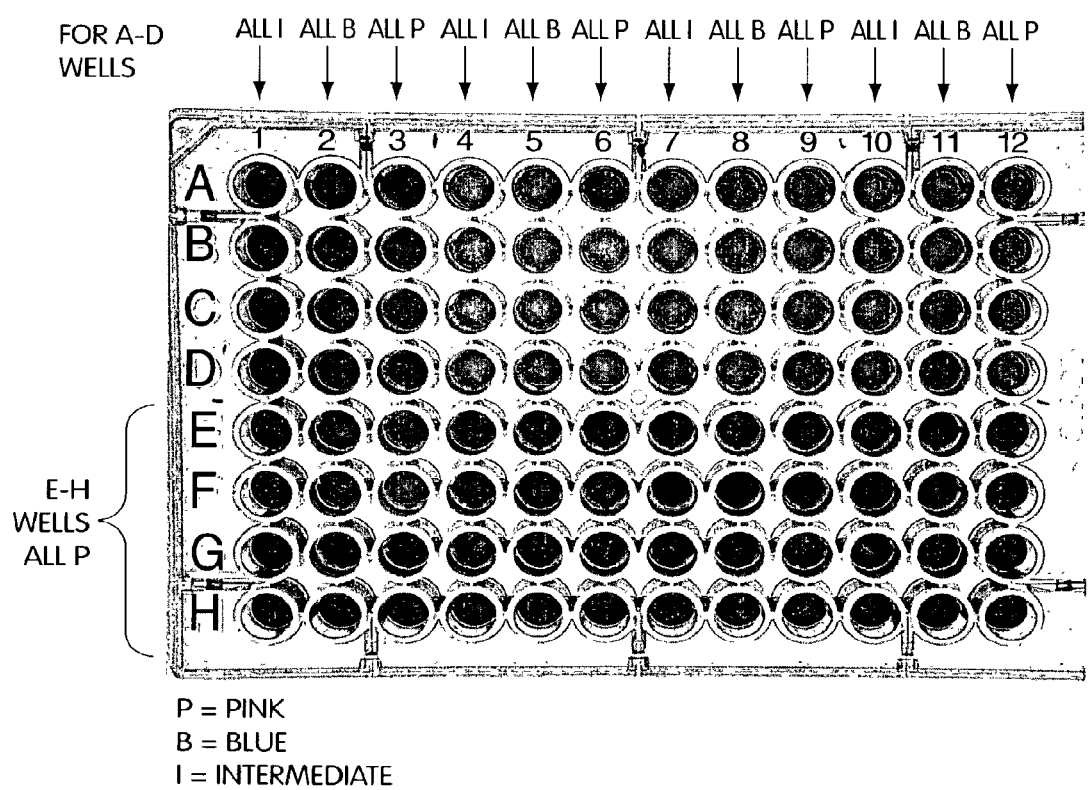

See FIGS. 8A-15D. Rows A-D contained colloid particles carrying immobilized His-PSMGFR. Rows E-H contained colloid particles carrying a random sequence peptide. Columns 2, 5, 8, and 11 contained lysates from a tumor cell line that overexpresses MUC1 (HTB-133). Columns 3, 6, 9, and 12 contained lysates from a tumor cell line that does not expresses MUC1 (CRL-1902). Columns 1, 4, 7, and 10 contain lysates from a tumor cell line that expresses, but does not overexpress, MUC1 (CRL-1504). Columns 1-3: NTA concentration on colloid: 20 micromolar; columns 4-6: 40 micromolar; columns 7-9: 60 micromolar; columns 10-12: 80 micromolar, all in total thiol concentration of 600 micromolar in deposition solution. FIG. 8A: time=0; FIG. 8B: time=15 minutes; FIG. 8C: time=1 hour; FIG. 8D: time=3 hours.

Overall, these results point to a mechanism involving a feedback loop involving both ligand production and aberrant expression of the MUC1 receptor.

Example 4a

Identification of Ligands that Bind to the MGFR Portion of the MUC1 Receptor In an effort to identify ligands to the MUC1 receptor, synthetic, His-PSMGFR peptides, GTINVHDVETQFN- QYKTEAASPYNLTISDVSVSDVPF-
PFSAQSGAHHHHHH (SEQ ID NO:2), which represents the portion of the MUC1 receptor, that remains attached to the cell surface after cleavage of the interchain binding region, were loaded onto NTA-Ni beads (cat. #1000630; available from Qiagen GmbH, Germany) and incubated with cell lysates in the presence (FIG. 9) or absence (FIG. 10) of the protease inhibitor PMSF (phenyl methyl sulfonyl fluoride). Lysates from T47D cells were used because this breast tumor cell line was known to overexpress MUC1; additionally, the inventors presented evidence herein (see FIG. 8A-D) that this cell line also overexpresses MUC1 ligand(s). T47D cells were cultured then sonicated for 1 minute to lyse the cells. Lysates were mixed with the PSMGFR peptide-presenting beads and incubated on ice with intermittent mixing for 1hr. As a negative control, an irrelevant peptide, HHHHHHRGEFTGTYI-
TAVT (SEQ ID NO:13), was attached to NTA-Ni beads and treated identically. Both sets of beads were washed 2× with phosphate buffer pH 7.4. Bound protein species were eluted by 3 additions of 100 uL of phosphate buffer that also contained 250 mM imidazole. For both the peptides, a portion of the first elution was removed and reserved to run as a separate sample, while the remainder was combined with the other 2 elutions and concentrated by TCA (tri-chloro acetic acid)-precipitation (Chen, L. et al., Anal. Biochem. Vol 269; pgs 179-188; 1999). Eluates were run on a 12% SDS gel, see FIG. 9. The gel was then silver stained (Schevchenko, A et al; Anal. Chem., Vol. 68; pg 850-858; 1996). Lanes were loaded as follows: (from left to right) (1) Benchmark pre-stained protein ladder (Gibco); (2) first eluate from the MUC1 peptide; (3) $1/10^{th}$ of TCA-concentrated sample; (4) blank; (5) $9/10^{th}$ TCA-concentrated sample; (6) first eluate negative control peptide; (7) $1/10^{th}$ of TCA-concentrated sample from the negative control peptide; (8) 0.5 picomoles BSA (as a standard); (9) $9/10^{th}$ TCA-concentrated sample from the negative control peptide; (10) silver stain SDS page standard (BioRad cat. #1610314). Referring now to FIG. 9, comparing lanes 2 and 6 (control), it can be seen that the MUC1 PSMGFR peptide bound distinguishably to three peptides: a first unique peptide that runs at an apparent molecular weight of 17kD; and a second peptide (more intense band) that runs at an apparent molecular weight of 23kD. Note that in lane 5, where the sample is the most concentrated, a third unique band is seen at about 35kD.

FIG. 10 shows the results of an experiment, which was identical to that shown in FIG. 9, with the exception that the protease inhibitor PMSF was not added. PMSF binds to and blocks the action of several enzymes, such as proteases. This experiment was performed, in the absence of PMSF, to determine whether an enzyme present in the lysate was a ligand of the MUC1 receptor. Referring now to FIG. 10, comparing lanes 3 (control) and 7, it can be seen that the MUC1, PSMGFR peptide bound distinguishably to one peptide, with an apparent molecular weight of 35 kD. Note that this band was visible in FIG. 9 (with PMSF), but was much fainter and only co-eluted from the most concentrated sample. These results are consistent with the idea that the PFMGFR portion of the MUC1 receptor is a substrate for a ligand of apparent molecular weight of about 35 kD and which may bean enzyme. As mentioned elsewhere herein, drug screens based on inhibition of binding between the PSMGFR and this ligand or the ligand in a crude cell lysate can identify compounds that inhibit the action of this enzyme.

TABLE 2

Cell lines were purchased from the ATCC (American Type Culture Collection, Manasses, VA) and are all breast carcinoma cell lines. Some lines have been shown to express or over express the tumor marker receptor MUC1, Her2/neu or the oncogenic enzyme cathepsin K.

| Cell line | Gel Result Co-elutes with PSMGFR peptide | Color change assay - yes, turned blue | Expression of species in cell line | Common name | ATCC name |
|---|---|---|---|---|---|
| 1. | +++ | ++++ | Expresses MUC1 | T-47D | HTB-133 |
| 2. | + | − | ND on MUC1 over expresses HER2/neu | UACC-893 | CRL-1902 |
| 3. | +++ | ++++ | Overexpresses MUC1 | ZR-75-1 | CRL-1500 |
| 4. | ++ | + | Express MUC1 over express cathepsin K | ZR-75-30 | CRL-1504 |

TABLE 3

| Cell line | Growth Media |
|---|---|
| HTB-133 | RPMI 1640 media, purchased from Mediatech supplemented with 1 mM sodium pyruvate, 10% FBS, 4.5 g/L glucose and 1.5 g/L sodium bicarbonate, with 2 IU bovine insulin per mL. |
| CRL-1902 | Liebovitz L-15 media (Sigma), supplemented with 10% FBS |
| CRL-1500 | RPMI 1640 media from Mediatech supplemented with 1 mM sodium pyruvate, 10% FBS, 4.5 g/L glucose and 1.5 g/L sodium bicarbonate |
| CRL-1504 | RPMI 1640 media from Mediatech supplemented with 1 mM sodium pyruvate, 10% FBS |

Example 4b

Demonstration that the Ligand that Interacts with MUC1 Cancer Cells is a Multimer In this example, it is demonstrated that a ligand produced by MUC1 cancer cells that triggers cell proliferation in these cells is a multimer.

Protein bands at 17 kD, 23 kD, and 35 kD were excised from the gels described above in Example 4a and submitted for peptide analysis. These gel bands purportedly contained ligands to the MGFR region of the MUC1 receptor. Recall that the 17 kD and 23 kD species bound to the MGFR peptide in the presence of the protease inhibitor, PMSF, while the 35 kD species bound when PMSF was not added to the cell lysate mixture.

The following peptide analysis was performed. Samples derived from the gel slices were proteolytically digested.

Fragments were then separated by microcapillary HPLC which was directly coupled to a nano-electrospray ionization source of an ion trap mass spectrometer. MS/MS spectra was obtained on-line. These fragmentation spectra were then correlated to known sequences using the SEQUEST® algorithm in conjunction with other algorithms Results were then manually reviewed to confirm consensus with sequences of known proteins.

Peptide sequences contained within both the 17 kD and the 23 kD bands (PMSF added to lysate) corresponded to a protein known as Metastasis Inhibition Factor NM23, which has been implicated in both the promotion and inhibition of metastasis of human cancers. Whether the role of NM23 is a tumor supressor or promoter may depend on the type of cancer. In ovarian, colon and neuroblastoma tumors, NM23 overexpression has been linked to a more malignant phenotype (Schneider J, Romero H, Ruiz R, Centeno M M, Rodriguez-Escudero F J, "NM23 expression in advanced and borderline ovarian carcinoma", *Anticancer Res,* 1996; 16(3A): 1197-202). However, breast cancer studies indicate that reduced expression of NM23 correlates with poor prognosis (Mao H, Liu H, Fu X, Fang Z, Abrams J, Worsham M J, "Loss of nm23 expression predicts distal metastases and poorer survival for breast cancer", Int J Oncol 2001 March; 18(3):587-91).

The sequences that were identified from the protein gel band described in FIGS. 9 and 10 and that are derived from a protein implicated in many cancers called Metastasis Inhibition Factor NM23 are shown below in Table 4. NM23 exists as a hexamer and may recognize an unmodified form of the MGFR portion of the MUC1 receptor.

Peptide sequences that were identified from the 35 kD gel band (PMSF NOT added to lysate) corresponded to more than one protein species, including 14-3-3, which is a signaling protein implicated in many cancers, and cathepsin D, which is a protease and is also implicated in tumor progression. 14-3-3 exists as a dimer and can simultaneously bind to two, identical phospho-serine peptides. This would dimerize the MGFR portion of the MUC1 receptor to trigger cell proliferation, which is consistent with the mechanism presented herein. Cathepsin D is a protease and may be involved in the cleavage of the MUC1 receptor.

The identity of these ligands is consistent with the MUC1-dependent cell proliferation mechanism that is disclosed herein, i.e., a ligand that dimerizes the MGFR portion of the MUC1 receptor triggers cell proliferation and cleavage of only a portion of the MUC1 extracellular domain exposes the functional part of the receptor which is defined by most or all of the PSMGFR sequence given in Table 1.

Consistent with methods of the invention, a therapeutic strategy is to identify compounds that either interrupt the interaction of one of the ligands with the MGFR portion of the MUC1 receptor, or to identify compounds that bind to and block the action of the ligand(s).

TABLE 4

17 kD species identified herein from gel band

1) Metastasis Inhibition Factor NM23     gi: 127982
TFIAIKPDGVQR (SEQ ID NO: 14)
VM*LGETNPADSKPGTIR (SEQ ID NO: 15)
VMLGETNPADSKPGTIR (SEQ ID NO: 16)
NIIHGSDSVK (SEQ ID NO: 17)

TABLE 4-continued

GLVGEIIKR (SEQ ID NO: 18)
GLVGEIIK (SEQ ID NO: 19)
23 kD species identified herein from gel band 1) Metastasis Inhibition Factor NM23     gi: 127982
TFIAIKPDGVQR (SEQ ID NO: 20)
YM*HSGPVVAM*VWEGLNVVK (SEQ ID NO: 21)
35 kD identified herein from gel band 1) 14-3-3 epsilon     gi: 5803225
AAFDDAIAELDTLSEESYK (SEQ ID NO: 22)
AASDIAM*TELPPTHPIR (SEQ ID NO: 23)
YLAEFATGNDR (SEQ ID NO: 24)
DSTLIMQLLR (SEQ ID NO: 25)
YDEMVESMK (SEQ ID NO: 26)
VAGM*DVELTVEER (SEQ ID NO: 27)
HLIPAANTGESK (SEQ ID NO: 28)
2) cathepsin D     gi: 4503143
DPDAQPGGELM*LGGTDSK (SEQ ID NO: 29)
DPDAQPGGELMLGGTDSK (SEQ ID NO: 30)
ISVNNVLPVFDNLM*QQK (SEQ ID NO: 31)
ISVNNVLPVFDNLMQQK (SEQ ID NO: 32)
QPGITFIAAK (SEQ ID NO: 33)
3) human annexin V with Proline substitution by Thrionine     gi: 3212603
GLGTDEESILTLLTSR (SEQ ID NO: 34)
DLLDDLKSELTGK (SEQ ID NO: 35)
SEIDLFNIR (SEQ ID NO: 36)

Examples 5a-d

Drug Studies Consistent with Mechanism Presented for MUC1 Cancer

In these examples, drugs that inhibit proliferation in MUC1 tumor cells specifically were compared to drugs that inhibit proliferation in both MUC1 tumor cells and other cells. Drugs, both specific and non-specific, were identified by exposing them to PSMGFR-presenting colloids in the presence of MUC1 tumor cell lysates. Drugs were identified as those that prevented colloid-colloid interactions. Cell studies resulted in a separation of these drugs into two groups—a group specific for MUC1 tumor cells and a non-specific group. Non-specific drugs did not bind to PSMGFR, but are presumed to bind the activating ligand, and inhibit proliferation of control cells as well as MUC1-presenting cells. Additionally, this group of drugs was somewhat toxic to both cell types, since they remove the activating ligand from interaction with the cells. Drugs specific for MUC1 tumor cells were found to bind to PSMGFR on beads, as demonstrated by HPLC analysis of the product of cleavage of PSMGFR from the beads.

Example 5a

Drug Screening Assay Using Colloid-Based Colorimetric Detection to Identify Agents that block the Interaction of the MGFR Portion of the MUC1 Receptor with its Activating Ligand(s)

The following is an example of a working drug screening assay to identify anti-cancer agents. In this example, a histidine-tagged peptide derived from the portion of the MUC1 receptor that remains attached to the cell surface after receptor cleavage (His-PSMGFR) was attached to NTA-nickel-SAM-coated gold colloids. The peptide-presenting colloids were incubated with lysates/supernatants from MUC1 presenting cells that were shown herein to contain ligands that cause dimerization or multimerization of that portion of the MUC1 receptor. This ligand-induced multimerization of the MGFR portion of the receptor causes the attached colloids to be drawn close together, which causes a change in the color of the colloid solution from pink to blue. Drugs that interfere with the binding of activating ligands to the MGFR portion of the receptor cause the solution to remain pink.

Figure 11:
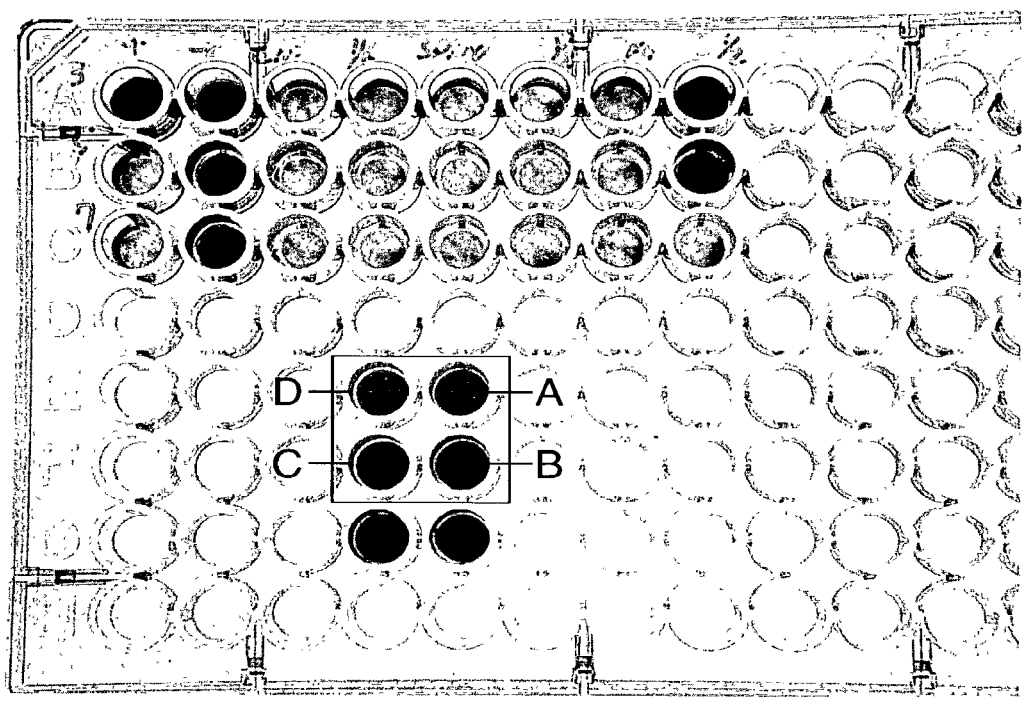
FIG. 11 is a black and white photocopy of an image of a 96-well plate illustrating a color-change binding assay between a MUC1-derived peptide and a ligand(s) present in a crude cell lysate from cells that overexpress MUC1.

NTA-SAM-coated colloids presenting the PSMGFR peptide were incubated with cell lysates/supernatants from T47D cells, which we previously showed by gel-electrophoresis to contain the ligand to MUC1 (Example 4a). Negative control wells contained colloids bound with a random sequence histidine-tagged peptide in place of the MUC1 peptide. FIG. 11, which is an image of 96-well plate illustrating a color-change binding assay, shows the results of the experiment. The well containing colloids that presented the PSMGFR peptide plus T47D cell lysates (Well A) changed color from pink to blue, indicating the presence of a multimerizing ligand. Wells that contained a random sequence peptide (RGD) in place of the PSMGFR peptide (Well B) remained pink. Wells that contained phosphate buffer in place of cell lysate also remained pink (Wells C and D).

The data below demonstrates the ability of anti-tumor drugs identified in accordance with the invention, specifically, calcimycin, fusaric acid, L-α-methyl-dopa, butylindazone, NS1619 and etomoxir to inhibit proliferation of cells that aberrantly express MUC1, by blocking the interaction of MGFR with ligands that promote cell proliferation.

An experiment similar to that described above was run in the presence of drug candidates to determine whether candidates could be identified that interfere with ligand/MGFR binding.

T47D cells were trypsinized from a T25 flask, pelleted, resuspended in phosphate buffer, and lysed by sonication to release the ligand into solution. NTA-SAM-coated colloids were bound with the His-PSMGFR peptide: GTINVHDVETQFNQYKTEAASPYNLTIS-DVSVSDVPFPFSAQSGAHHHHHH (SEQ ID NO:2), 200 µl NTA-SAM-coated colloids were incubated with 20 µl 100 µM peptide in phosphate buffer for 15 minutes, pelleted to remove unbound peptide, and resuspended in phosphate buffer. Negative control colloids were incubated with a random sequence histidine-tagged peptide in place of the MUC1 peptide. The cell lysate (65 µl) was mixed with 5 µl drug candidate in DMSO and added to 30 µl MUC1-peptide-bound colloids in the wells of an ELISA plate for a final drug concentration of approximately 100 µM. Positive controls contained DMSO in place of a drug candidate; negative controls contained DMSO in place of a drug candidate, and colloids bound with a random sequence peptide in place of the MUC1 peptide. A color change from pink to blue indicates that the ligand in the cell lysate bound to the MUC1-peptide, dimerizing the peptide, and bringing the colloids into close enough proximity with one another to cause a color change. Positive controls, which do not contain a drug candidate, change color from pink to blue within two hours, as there is nothing to inhibit the interaction between the MUC1 peptide and the ligand present in the cell lysate. A lack of color change (wells remain pink) indicates that the drug candidate blocked the interaction between the MUC1 peptide and the cognate ligand, either by binding to the MGFR portion of the MUC1 receptor, inhibiting a modifying enzyme, or by binding to its activating ligand. Negative control wells, which contain colloids presenting a random sequence peptide in place of the MUC1 peptide, remain pink, as the ligand to the MUC1 peptide will not dimerize the random sequence peptide. FIG. 12 shows a sample drug-screening plate used in the assay described above. Positive control wells (A1-D1) changed color from pink to blue within two hours, while negative control wells (E1-H1) remained pink. Well E6 contains a drug that inhibited the interaction between the MUC1 peptide and the cognate ligand, causing the well to remain pink.

Example 5b1

Secondary Screen to Determine Mode of Action of Identified Drug Agents—Proliferation of Cells Treated with Drug Candidates that Disrupt the Interaction of MUC1 with its Natural Ligand Previously, we showed in vitro that the ligand to the MGFR portion of the MUC1 receptor caused dimerization, or multimerization of the PSMGFR peptide on colloids, see Example 3a. We also showed that dimerization of the MGFR portion of the receptor induced an enhanced cell proliferation, see Example 2. It then follows that agents that block the interaction of the MGFR portion of the receptor with its activating ligands will block the proliferation of MUC1-presenting tumor cells. Therefore, drugs that were identified using the in vitro drug screening assay described in Example 5a were tested in a functional assay to determine their ability to inhibit MUC1-dependent cell proliferation.

Figure 13:
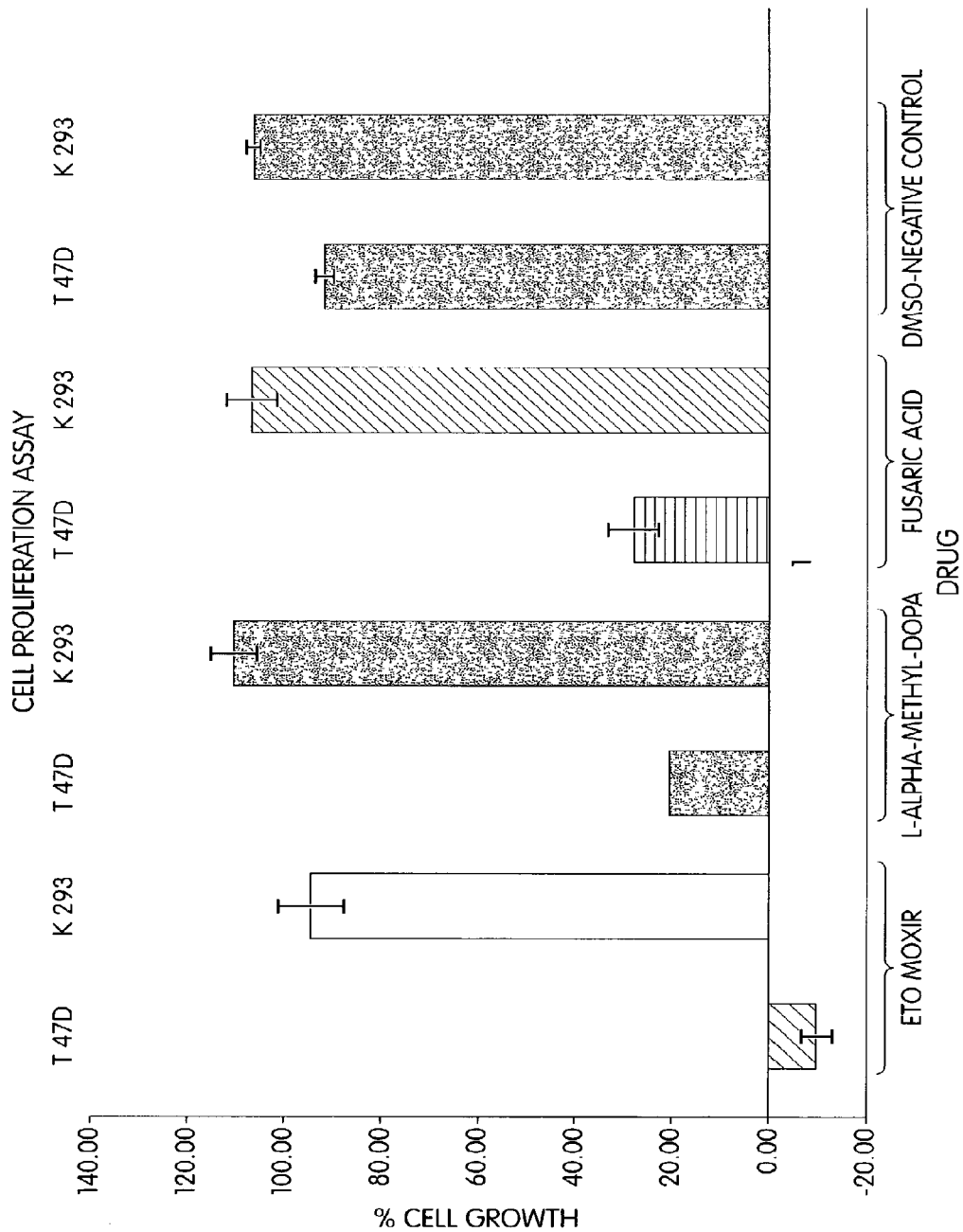
FIG. 13 shows a histogram illustrating the selective inhibition of proliferation of tumor cells that aberrantly express the MUC1 receptor, in response to treatment with compounds of the invention, and lack of an effect on cells that do not express MUC1.

T47D cells, mammary carcinoma cells known to overexpress MUC1, were grown in the wells of an ELISA plate along with K293 cells, human embryonic kidney cells which will serve as the negative control. 100 µl cells in growth media were added to the wells of an ELISA plate and the cells were allowed to adhere overnight. The number of cells in each well on the plate were then counted and recorded. 1 µl of a drug candidate in DMSO was then added to each well of both the T47D cells and the K293 cells. 1 µl DMSO alone was added to control wells. Each well was repeated in triplet. The cells were allowed to grow for 48 hours, the normal doubling time for these cell lines. The number of cells in each well was again counted and recorded. The percent cell growth over this 48-hour period was calculated, and the percent cell growth for wells containing a drug candidate versus DMSO were compared. As seen in FIG. 13, Etomoxir, L-alpha-methyl DOPA, and Fusaric acid selectively inhibited proliferation of the MUC1-expressing tumor cells over K293 negative control cells. The DMSO control cells (both T47D and K293) show that DMSO alone does not effect cell proliferation. FIG. 13 is a histogram illustrating the selective inhibition of proliferation of tumor cells that aberrantly express the MUC1 receptor (T47D cell line), in response to treatment with compounds of the invention, and lack of an effect on cells that do not express MUC1 (K293). Cell growth in the presence of Etomoxir was ±10.2% for T47D cells and 94% for control cells (K293); Cell growth in the presence of L-alpha-methyl-DOPA was 20% for T47D cells and 110% for control cells (K293); Cell growth in the presence of Fusaric acid was 27.7% for T47D cells, and 106.7% for control cells (K293); Cell growth in the absence of any drug (but with an equivalent amount of DMSO added) was 91.3% for T47D cells, and 106.2% for control cells (K293).

Example 5b2

Drugs Identified with the Colorimetric in vitro Drug Screen Separate into Two Categories—Selective for MUC1-Presenting Cells and Non-Selective As discussed, compounds identified in the in vitro drug screening assay (described in Example 5a), which identifies compounds that interfere with the interaction between the MGFR portion of the MUC1 receptor and its activating ligands, can inhibit cell proliferation by three modes of action. These drugs can a) block the activity of the activating ligand(s), that act as growth factors; b) directly bind to and block the MGFR portion of the receptor; or c) inhibit the activity of enzymes that modify the MUC1 receptor. It is expected that drugs that function by (a) will inhibit proliferation of a variety of cell types, while those that function according to (b) and (c) will selectively inhibit the proliferation of MUC1-presenting cells.

Figure 14:
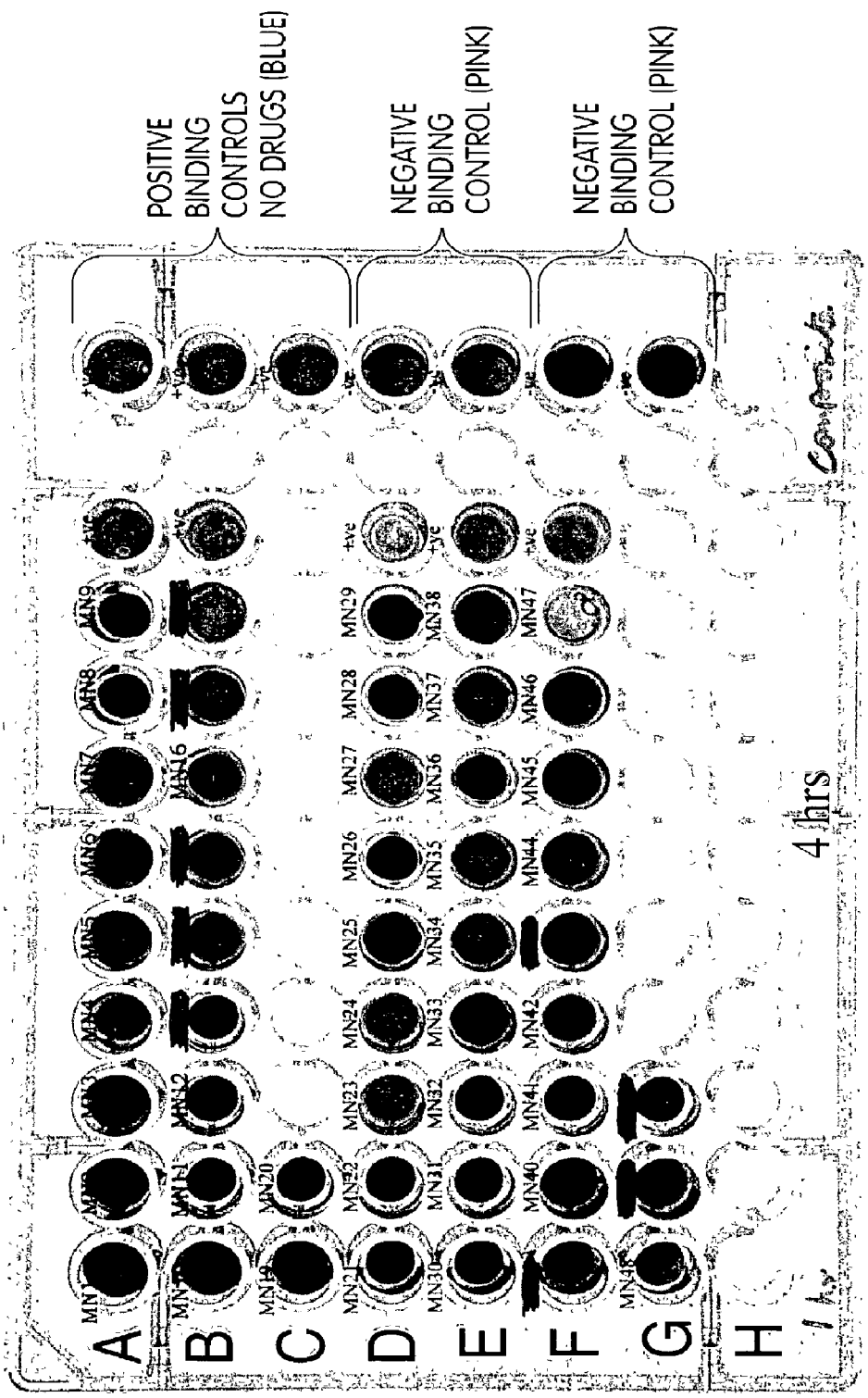
FIG. 14 is a black and white photocopy of an image of a 96-well plate illustrating a color-change drug-screening assay identifying several compounds that interfere with the interaction of the MGFR portion of the MUC1 receptor and a multimerizing ligand(s)
Figure 15:
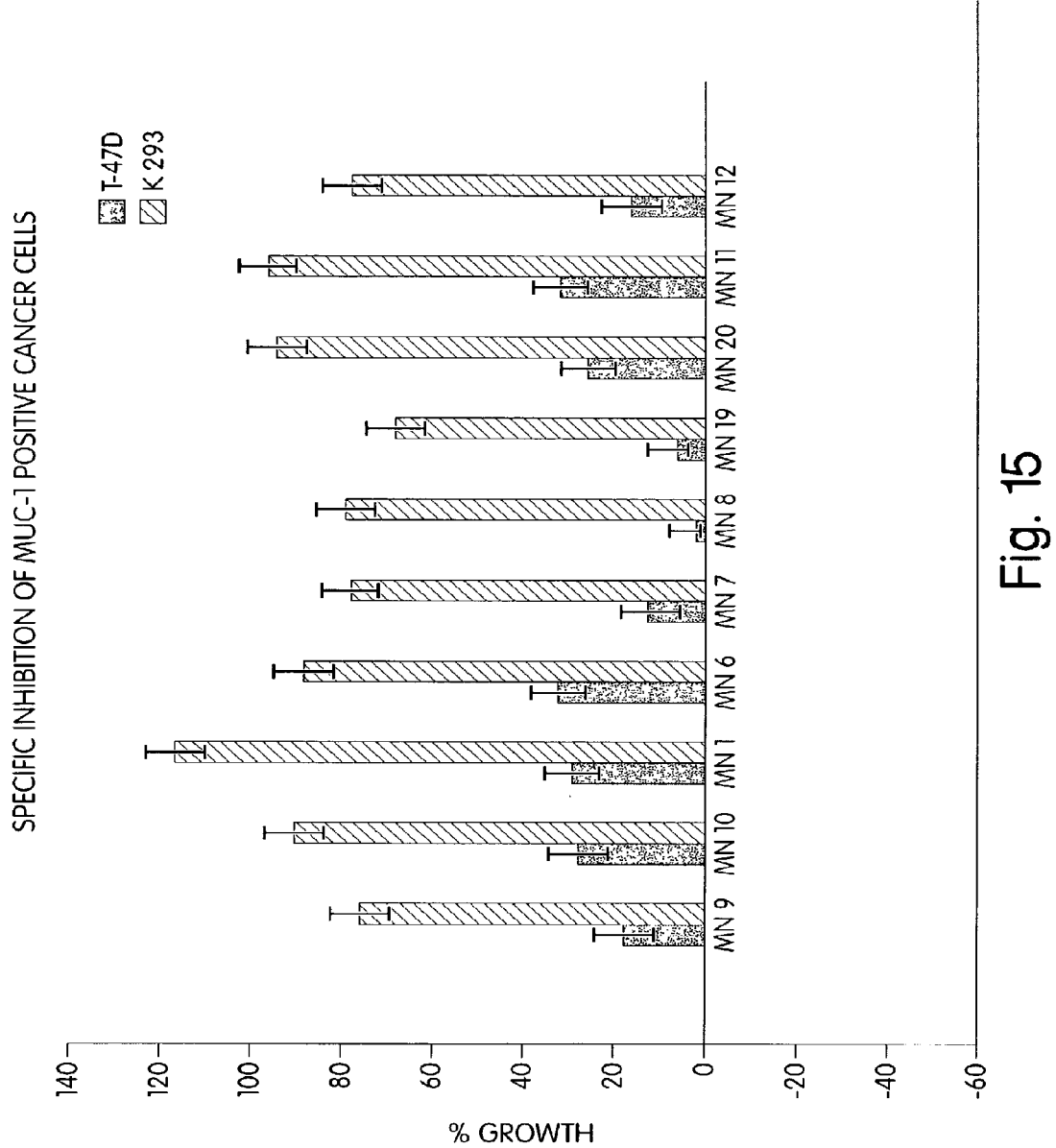
FIG. 15 shows a histogram illustrating the selective inhibition of proliferation of tumor cells that aberrantly express the MUC1 receptor, in response to treatment with drugs that specifically inhibit MUC1 positive cells.

FIG. 14 is an image of a multi-well plate in which the colorimetric drug screening assay (see Example 5a) identified several compounds (each designated by a MN#) that interfered with the interaction of the MGFR portion of the MUC1 receptor and a multimerizing ligand(s). All of the drug-containing wells demonstrate interference with ligand binding as evidenced by each of the wells either remaining pink or turning purple, indicative of binding being essentially eliminated or reduced over positive binding controls (top three wells of right-most column, which are blue). Wells in the top half of the plate (rows A-C) contain drugs that were shown in the functional cell proliferation assay (see Example 5b) to selectively inhibit the proliferation of MUC1-presenting tumor cells by either directly binding to the MGFR portion or by acting on its modifying enzymes. FIG. 15 is a bar graph that compares the percentage cell growth of MUC1 tumor cells (T47Ds) to a control cell line (K293s), in response to treatment with novel drugs, (described in greater detail in commonly-owned, co-pending U.S. provisional patent application Ser. Nos. 60/317,302 and 60/317,314, both filed on Sep. 5, 2001 and entitled COMPOSITIONS AND METHODS OF TREATMENT OF CANCER). As is readily apparent, this group of drugs dramatically inhibited or completely prevented the proliferation of MUC1-presenting tumor cells, while leaving the control cells, in most cases, unaffected.

Figure 16:
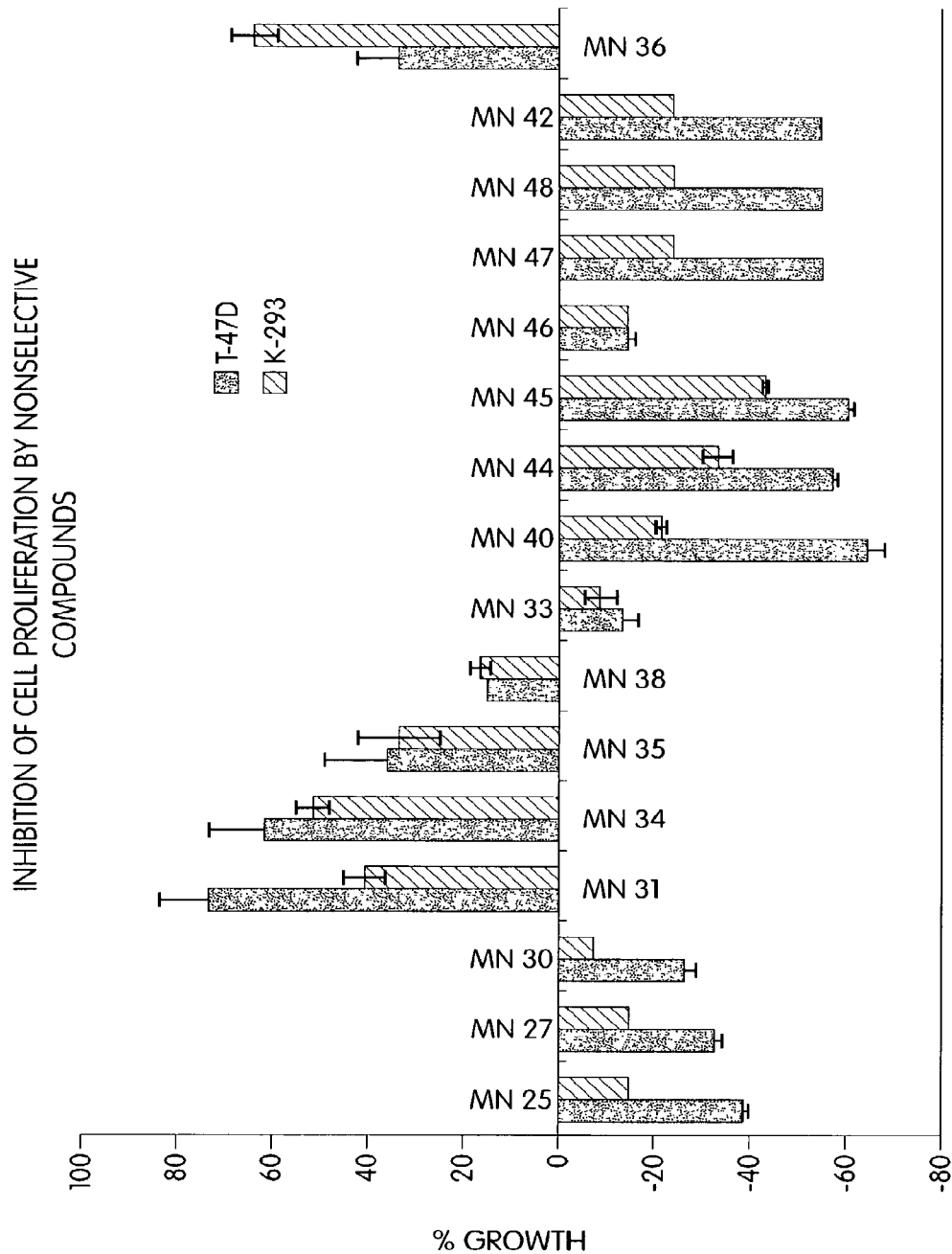
FIG. 16 shows a histogram illustrating the nonselective inhibition of proliferation of cells in response to treatment with drugs that non-specifically inhibit cell proliferation.

Wells in the bottom half of the plate (rows D-G) contain drugs that were shown in the cell proliferation assay to act non-selectively as they inhibited the proliferation of both cell types. FIG. 16 is a bar graph that shows the effect of these novel drugs (described in greater detail in commonly-owned, co-pending U.S. provisional patent application Ser. Nos. 60/317,302 and 60/317,314, both filed on Sep. 5, 2001 and entitled COMPOSITIONS AND METHODS OF TREATMENT OF CANCER) on cell growth for MUC1-presenting cells (T47D) and a control cell line (K293). Notably, this group of drugs, which presumably bind to growth factors, is toxic to the cells as one skilled in the art would expect for agents that act on growth factors.

Example 5c

Co-Elution of Drugs with PSMGFR Peptide Proves Direct Binding to MGFR

Figure 17:
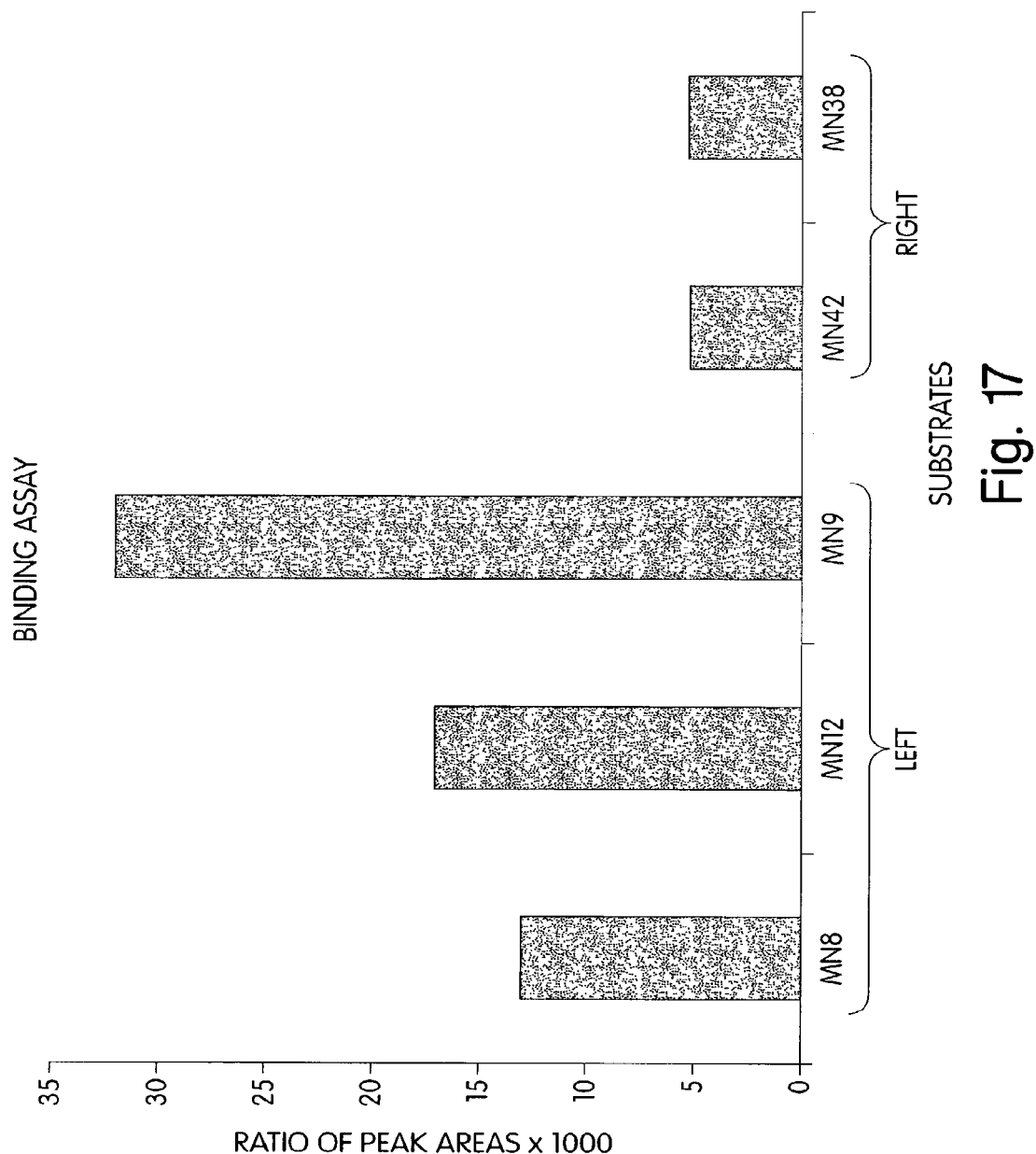
FIG. 17 shows a histogram illustrating that drugs that selectively inhibit proliferation of tumor cells that aberrantly express the MUC1 receptor bind to the PSMGFR, while drugs that non-selectively inhibit cell proliferation do not.

Herein, we show that several drugs inhibited MUC1-dependent cell proliferation by binding to the MGFR portion of the MUC1 receptor and disrupting the interaction between the MGFR portion and its cognate ligand. The direct binding of several drugs to the PSMGFR peptide was demonstrated using two methods. The His-PSMGFR peptide was attached to NTA-nickel agarose beads then separately incubated with each of the drug candidates. 100 µl beads were bound to saturation with 1 mg peptide, rinsed to remove unbound peptide, and incubated with 25 µl 2.7 mg/ml drug candidate in DMSO for one hour in 5 ml phosphate buffer. Unbound drugs were washed away with phosphate buffer, and the peptide was eluted from the beads with PBS, 250 mM imidazole. If the drug candidate bound to the peptide, it would co-elute with the peptide in the imidazole solution. Peptide-drug complexes were then separated by HPLC. HPLC elution peaks from the complex were compared to the elution peaks from the drug, injected alone, and the PSMGFR peptide alone. In a pilot study, 3 drugs, chosen randomly from the group of drugs that selectively inhibit MUC1 cell proliferation, were compared to 3 drugs chosen randomly from the group that non-selectively inhibited cell proliferation. As seen in FIG. 17, the drugs on the left, chosen from the selective group, bind to the PSMGFR peptide, while drugs on the right, chosen from the non-selective group, did not.

In a similar experiment, eluates from the beads were analyzed by TLC (thin layer chromatography). Two drugs, calcimycin and NS1619 which could be tracked by TLC, because they fluoresced under UV light, were tested. NTA-nickel bead-immobilized peptides were incubated with the drugs as described above, rinsed and eluted from the beads, then rotoevaporated to remove the aqueous buffer. The solid was then resuspended in ethylacetate, 5% methanol and spotted on TLC plates then run in the same organic solvent. Both drugs co-eluted with the PSMGFR peptide, showing conclusively that the drugs bind to the PSMGFR peptide. Calcimycin, gave a clear blue spot under 250 nm UV light and ran at a less polar position (as expected) than the peptide itself. The second drug, NS1619, gave a less visible spot at a slightly less polar position than the peptide. The TLC plate was stained with iodine to reveal the peptide spots, which are visible due to the presence of tyrosine and phenylalanine residues.

Prophetic Example 5d

Discriminating between drugs that Inhibit MUC1-Dependent Cell Proliferation by Binding to and Blocking the MGFR Portion of the MUC1 Receptor and Those that Inhibit Selective Proliferation by Acting on Enzymes that Modify the MGFR Portion This experiment is designed to distinguish drugs that selectively inhibit MUC1 cell proliferation by inhibiting modifying enzymes from drugs that inhibit by binding to and blocking the MGFR portion of the MUC1 receptor. Ex. 8 below shows that ligand(s) present in the MUC1 lysate were not able to bind PSMGFR peptide when the enzyme inhibitor PMSF was added to the lysate. This implied that the PSMGFR is first modified before it recognizes its cognate ligand(s). Using the drug screening assay described in Ex. 5a, one cannot differentiate between drugs that will selectively block the proliferation of MUC1-presenting cells and those that block the proliferation of a wide variety of cells, i.e. by inhibiting the MUC1 ligands that act as growth factors. To identify drugs that are selective for MUC1, drug hits are subjected to a secondary assay, which measures the percentage cell proliferation of MUC1 cells compared to control cells. Of the drugs that are selective for MUC1-presenting cells, neither assay can differentiate between drugs that bind to and block the MGFR and those that inhibit its modifying enzymes. Since enzyme modified peptides migrate through a gel at a slower rate than unmodified peptides, one can use this difference in gel mobility to determine which drugs act by inhibiting the enzyme(s).

To determine which drugs function via which of these two mechanisms, drugs are incubated with lysates and supernatants from MUC1-presenting cells, to allow the drugs to inhibit MUC1-modifying enzymes. The synthetic His-PSMGFR peptide, immobilized on commercially available NTA-nickel beads, are then mixed with this lysate mixture.

After a 30-minute incubation on ice, excess lysate and drug are discarded in the supernatant after the beads and attached peptide are pelleted by centrifugation. Peptides are then released from the beads by the addition of 100 μL of 25 mM of imidazole. Samples are then analyzed by standard methods of SDS-PAGE on a 15% polyacrylamide gel. The unmodified PSMGFR peptide runs with an apparent MW of 9 kd, while the modified peptide runs at an apparent MW of 11 kd. A shift to the MW characteristic of the unmodified peptide, after incubation with lysate and drug candidate, indicates that the drug under study acts by inhibiting a modifying enzyme.

Example 6

Modulation of Inhibitory Effect of Etomoxir on Cell Proliferation

Etomoxir, identified as a composition useful in treatment of MUC1-dependant tumors in this invention, was shown to be specific for MGFR by modulating its effect on cell proliferation via competitive inhibition of the MGFR/drug interaction by adding excess PSMGFR in cell growth media.

Figure 18:
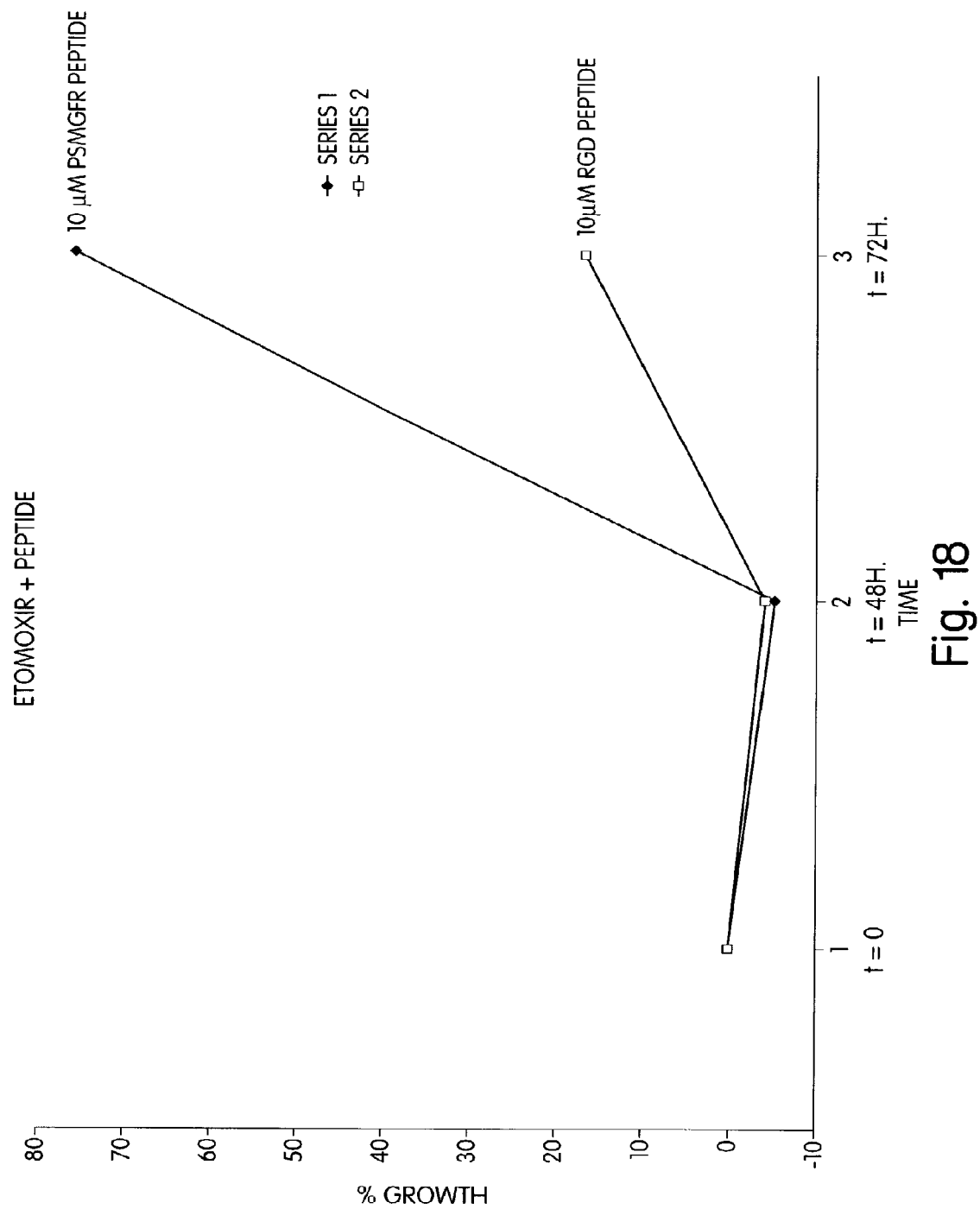
FIG. 18 is a graph showing that the inhibition of MUC1-dependent cell proliferation induced by an anti-tumor drug identified in accordance with the invention, is modulated when a synthetic peptide, corresponding to the portion of MUC1 that remains at the cell following cleavage, competitively inhibits the drug-cell surface receptor interaction.

The following experiment was performed in triplicate. T47D cells were grown to approximately 30% confluency. Etomoxir (approx. 100 micromolar) was added and cell proliferation was observed to be arrested. Then, a synthetic peptide (PSMGFR) was added to the cell growth media under normal cell growth conditions. Addition of PSMGFR caused increased cell proliferation, due to consumption of Etomoxir by PSMGFR (curve A of FIG. 18). As a control, cells were exposed to Etomoxir and a control peptide (RGD) of approximately the same molecular weight as PSMGFR and cell proliferation (curve B of FIG. 18) did not increase to the extent that occurred when PSMGFR was added.

Example 7

Evidence for Enzyme Modification of the MGFR Portion of the MUC1 Receptor

Figure 19:
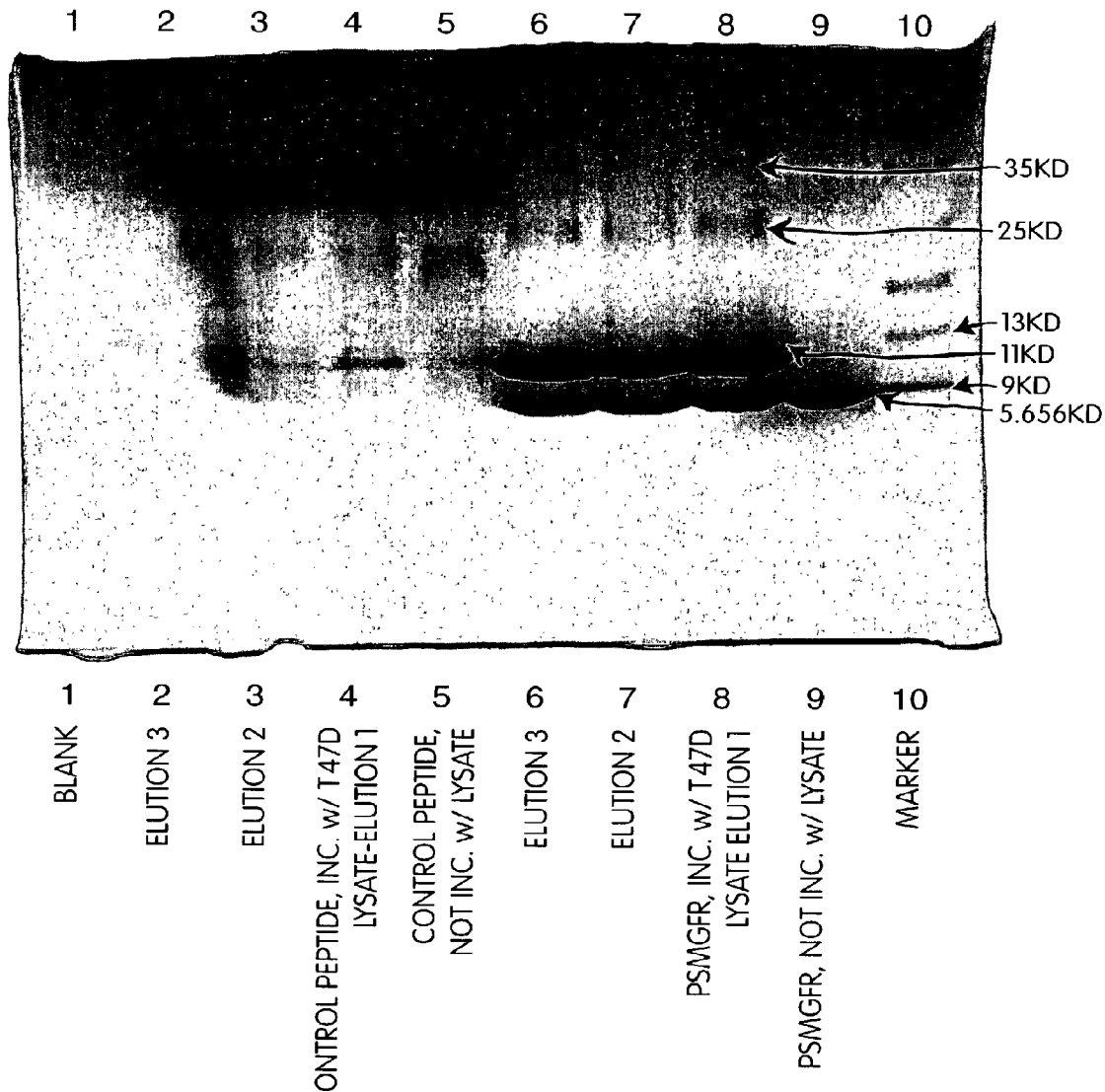
FIG. 19 is a black and white photocopy of a comassie blue-stained gel showing that the PSMGFR peptide runs at an apparently higher molecular weight after incubation with cell.

The following experiment was performed to investigate the possibility that the portion of the MUC1 receptor that remains attached to the cell surface after receptor cleavage (MGFR) is enzyme-modified. Synthetic, His-PSMGFR peptides, (SEQ ID NO: 2) were loaded onto NTA-Ni beads and either incubated with T47D cell lysates or as a negative control, incubated with cell growth media. Incubation was for 1 hour, on ice with intermittent mixing. As a second negative control, an irrelevant peptide, RGD (SEQ ID NO: 12) was attached to NTA-Ni beads and treated identically. Both sets of beads were washed 2× with phosphate buffer pH 7.4. Bound protein species were eluted by addition of 250 mM imidazole. Lanes were loaded as follows: (from right to left) (10) pre-stained protein ladder (Gibco); (9) bead immobilized PFMGFR peptide which was not incubated with cell lysates; (8-6) eluates of bead immobilized PFMGFR peptide which was incubated with T47D cell lysates; (5) eluates of bead immobilized negative control peptide which was not incubated with T47D cell lysate; (4-2) eluates of the negative control peptide was incubated with the lysate. Referring now to FIG. 19, comparing lanes 6-8 and 9 (control), it can be seen that after incubation with the lysates (6-8) the MUC1 PSMGFR peptide runs at a higher molecular weight than when it was incubated with cell growth media (9). Comparing lanes 5 and 2-4, there is no change in the apparent molecular weight of the control peptide after incubation with the cell lysate. These results are consistent with the idea that a ligand in the lysate of T47D cells is modifying the PSMGFR peptide portion of the MUC1 receptor.

These results are also consistent with the idea that the ligand is an enzyme that covalently couples two adjacent MGFR portions of the MUC1 receptor, causing dimerization of the receptors and initiates a cell proliferation signaling cascade. According to this mechanism, drugs of the invention interrupt cell proliferation by inhibiting the action of this enzyme.

Example 8

Demonstration that the MGFR Peptide is Enzymatically Modified Before its Natural Ligands Recognize it To test the hypothesis that the MGFR portion of the MUC1 receptor is enzymatically modified prior to binding to its ligand(s), the drug screening assay described in Example 5a was performed in the presence or absence of an enzyme inhibitor, PMSF (phenylmethylsulfonyl fluoride; Sigma chemical Co. St. Louis Mo., USA). T47D cells, which are breast tumor cells that aberrantly express MUC1, were grown to 70% confluency, treated with trypsin to detach from the flask, and pelleted by centrifugation. A lysate was prepared as follows from the pellets of two T75 flasks. Cell pellets were resuspended in 300 μL phosphate buffer (10 mM sodium phosphate, 100 mM NaCl, pH 7.4). The lysate was divided into two parts. One aliquot of lysate was used as is. To the second aliquot was added 9 μL of a 100 mM stock solution to achieve a final concentration 3 mM. The lysates were frozen and thawed four times with 15 seconds of vigorous mixing after each thawing. Lysates were then pelleted by centrifugation and the supernatant collected. Lysates were diluted by adding 6.2 ml of phosphate buffer. The drug screening assay was then performed as described in Example 5a, with the exception that no drugs were added. Rather the ability of the ligand(s) in the lysate to bind to the MGFR in a multimeric way, which would result in the solution color to change to blue, was tested. As can be seen in FIG. 20, solutions containing PMSF did not change color and remained pink. Wells A 1&2 turned from pink to blue within an hour and are the positive control wells, which contain the His-PSMGFR peptide immobilized on gold colloids and lysates/supernatants from T47D cells. Wells A 3&4 contain the same components as wells A 1&2, with the exception that the lysate/supernatant mixture was first treated with the enzyme inhibitor PMSF; wells containing PMSF do not undergo the solution color change and remain pink. Wells B 1&2 are negative control wells that contain the colloid-immobilized His-PSMGFR peptide but are incubated with buffer rather than lysates, and remain pink. Wells C 1&2 are also negative control wells in which the peptide immobilized on the colloids is an irrelevant peptide (RGD) that is incubated with the lysate, and they remain pink as well.

Prophetic Example Involving Screening for Drugs that Affect MUC 1 Cleavage State The release of the MUC 1 IBR can be correlated to the progression of cancer. The following is a description of a whole cell assay that identifies drug candidates that affect cleavage state of these receptors. The screen also identifies drug candidates that directly or indirectly modulate any step, including but not limited to enzyme cleavage, receptor production, expression, stability, transport or secretion, that ultimately results in a reduction of the self-aggregating portion of the receptor being shed and released from the cell.

Tumor derived cells expressing a cell surface receptor of the type described above, are cultured and treated with a drug candidate. Following some incubation period, a peptide aggregation assay is performed on the solution surrounding the cell. Colloids bearing a binding peptide e.g. an antibody against a constant region of the receptor, remote from the enzyme cleavage site (amino acid 425-479 for MUC1; numbers refer to Andrew Spicer et al., J. Biol. Chem Vol 266 No. 23, 1991 pgs. 15099-15109; these amino acid numbers correspond to numbers 985-1039 of GENBANK® accession number P15941; PID G547937), are added to the solution. If the shed portion of the receptor contains the self-aggregating portion, the receptors in solution will aggregate and cause the attached colloids to aggregate, causing a visibly detectable change in the solution, for example: color change or the formation of visible aggregates. An inhibition of this visible change indicates an agent that is effective for treating the disease state.

The list of sequences in Table 1 is representative of sequence fragments that are found within the overall sequence of the full-length peptide. Any set of at least 10 contiguous amino acids within any of the sequence fragments of Table 1 may be sufficient to identify the cognate binding motif. The list of sequences of Table 1 is meant to embrace each single sequence and when mentioning fragment size, it is intended that a range embrace the smallest fragment mentioned to the full-length of the sequence (less one amino acid so that it is a fragment), each and every fragment length intended as if specifically enumerated. Thus, if a fragment could be between 10 and 15 in length, it is explicitly meant to mean 10, 11, 12, 13, 14, or 15 in length.

With reference to Table 1, the receptor can be cleaved at a number of different sites to generate peptide fragments with alternative beginnings and endings. For these fragments of Table 1 any stretch of 8 to 10 contiguous amino acids, either upstream or downstream, may be enough to identify the particular fragment that is the binding entity referred to herein.

In addition to the diagnostics and screening assays of the invention, the invention relates to therapeutic methods for the treatment and prevention of cancer and related products. For instance, in one aspect the invention relates to a method for treating a subject having a cancer or at risk of developing cancer by administering to the subject an agent that reduces cleavage of a cell surface receptor IBR from a cell surface receptor.

Those skilled in the art would readily appreciate that all parameters listed herein are meant to be exemplary and that actual parameters will depend upon the specific application for which the methods and apparatus of the present invention are used. It is, therefore, to be understood that the foregoing embodiments are presented by way of example only and that, within the scope of the appended claims and equivalents thereto, the invention may be practiced otherwise than as specifically described. Specifically, those of ordinary skill in the art will recognize, or be able to ascertain using no more than routine experimentation, many equivalents to the specific embodiments of the invention described herein. Such equivalents are intended to be encompassed by the following claims.

Several methods are disclosed herein of administering a subject with a compound for prevention or treatment of a particular condition. It is to be understood that in each such aspect of the invention, the invention specifically includes, also, the compound for use in the treatment or prevention of that particular condition, as well as use of the compound for the manufacture of a medicament for the treatment or prevention of that particular condition.

In the claims, all transitional phrases such as "comprising", "including", "carrying", "having", "containing", "involving", and the like are to be understood to be open-ended, i.e. to mean including but not limited to. Only the transitional phrases "consisting of" and "consisting essentially of", respectively, shall be closed or semi-closed transitional phrases.

In the claims, amino acid sequence numbers are as listed in Andrew Spicer et al., J. Biol. Chem. Vol 266 No. 23, 1991 pgs. 15099-15109.

I claim:

1. A monoclonal antibody or antigen-binding fragment thereof, wherein the antibody or antigen-binding fragment thereof specifically binds to a peptide consisting of the amino acid sequence set forth at positions 1110-1154 of SEQ ID NO: 10.

2. An antibody or antigen-binding fragment thereof as recited in claim 1, wherein the antibody or antigen-binding fragment thereof is bivalent.

3. An antibody or antigen-binding fragment thereof as recited in claim 1, wherein the antibody or antigen-binding fragment thereof is monovalent.

4. A composition comprising the antibody or antigen-binding fragment of claim 1.

5. The composition as recited in claim 4, which is a pharmaceutical composition and further comprises a pharmaceutically acceptable carrier.

6. A kit comprising: the antibody or antigen-binding fragment thereof according to claim 1.

7. A monoclonal antibody or antigen-binding fragment thereof that specifically binds to an epitope of a MUC1 polypeptide comprising SEQ ID NO: 10, wherein said epitope is contained within the region of the polypeptide consisting of the amino acid sequence set forth at positions 1110-1154 of SEQ ID NO: 10.

8. A monoclonal antibody or antigen-binding fragment thereof, wherein the antibody or antigen-binding fragment thereof specifically binds to a peptide consisting of the amino acid sequence set forth at positions 1110-1142 of SEQ ID NO: 10.

9. A monoclonal antibody or antigen-binding fragment thereof that specifically binds to an epitope of a MUC1 polypeptide comprising SEQ ID NO: 10, wherein said epitope is contained within the region of the MUC1 polypeptide consisting of the amino acid sequence set forth at positions 1110-1142 of SEQ ID NO: 10.

10. A polyclonal antibody that specifically binds to an epitope of a MUC1 polypeptide comprising SEQ ID NO: 10, wherein said epitope is contained within the region of the MUC1 polypeptide consisting of the amino acid sequence set forth at positions 1110-1154 of SEQ ID NO: 10, but does not binds to an epitope of the MUC1 polypeptide outside of said region.

11. A polyclonal antibody that specifically binds to an epitope of a MUC1 polypeptide comprising SEQ ID NO: 10, wherein said epitope is contained within the region of the MUC1 polypeptide consisting of the amino acid sequence set forth at positions 1110-1142 of SEQ ID NO: 10, but does not binds to an epitope of the MUC1 polypeptide outside of said region.

12. A polyclonal antibody produced by immunizing an animal with an immunogen comprising a peptide consisting of the amino acid sequence set forth at positions 1110-1154 of SEQ ID NO: 10.

13. A polyclonal antibody produced by immunizing an animal with an immunogen comprising a peptide consisting of the amino acid sequence set forth at positions 1110-1154 of SEQ ID NO: 10, wherein said antibody specifically binds to an epitope of a MUC1 polypeptide comprising SEQ ID NO: 10, wherein said epitope is contained within the region of the polypeptide consisting of the amino acid sequence set forth at positions 1110-1154 of SEQ ID NO: 10.

* * * * *

SEQUENCE LISTING

<160> NUMBER OF SEQ ID NOS: 36

<210> SEQ ID NO 1
<211> LENGTH: 39
<212> TYPE: PRT
<213> ORGANISM: Artificial Sequence
<220> FEATURE:
<223> OTHER INFORMATION: Histidine-Tagged Truncated Receptor (His-TR)

<400> SEQUENCE: 1

Gly Thr Ile Asn Val His Asp Val Glu Thr Gln Phe Asn Gln Tyr Lys
1               5                   10                  15

Thr Glu Ala Ala Ser Pro Tyr Asn Leu Thr Ile Ser Asp Val Ser Val
            20                  25                  30

Ser His His His His His His
        35

<210> SEQ ID NO 2
<211> LENGTH: 51
<212> TYPE: PRT
<213> ORGANISM: Artificial Sequence
<220> FEATURE:
<223> OTHER INFORMATION: His-PSMGFR peptides -continued

```
<400> SEQUENCE: 2

Gly Thr Ile Asn Val His Asp Val Glu Thr Gln Phe Asn Gln Tyr Lys
1               5                   10                  15

Thr Glu Ala Ala Ser Pro Tyr Asn Leu Thr Ile Ser Asp Val Ser Val
                20                  25                  30

Ser Asp Val Pro Phe Pro Phe Ser Ala Gln Ser Gly Ala His His His
            35                  40                  45

His His His
    50

<210> SEQ ID NO 3
<211> LENGTH: 54
<212> TYPE: PRT
<213> ORGANISM: Artificial Sequence
<220> FEATURE:
<223> OTHER INFORMATION: "Extended Sequence of the MUC1 Growth Factor
      Receptor" (ESMGFR)

<400> SEQUENCE: 3

Val Gln Leu Thr Leu Ala Phe Arg Glu Gly Thr Ile Asn Val His Asp
1               5                   10                  15

Val Glu Thr Gln Phe Asn Gln Tyr Lys Thr Glu Ala Ala Ser Pro Tyr
                20                  25                  30

Asn Leu Thr Ile Ser Asp Val Ser Val Ser Asp Val Pro Phe Pro Phe
            35                  40                  45

His His His His His His
    50

<210> SEQ ID NO 4
<211> LENGTH: 31
<212> TYPE: PRT
<213> ORGANISM: Artificial Sequence
<220> FEATURE:
<223> OTHER INFORMATION: Histidine-Tagged Primary Sequence of the
      Interchain binding Region (His-PSIBR)

<400> SEQUENCE: 4

His His His His His His Gly Phe Leu Gly Leu Ser Asn Ile Lys Phe
1               5                   10                  15

Arg Pro Gly Ser Val Val Val Gln Leu Thr Leu Ala Phe Arg Glu
                20                  25                  30

<210> SEQ ID NO 5
<211> LENGTH: 46
<212> TYPE: PRT
<213> ORGANISM: Artificial Sequence
<220> FEATURE:
<223> OTHER INFORMATION: Histidine-Tagged Repeat Motif 2 (His-RM2)

<400> SEQUENCE: 5

Pro Asp Thr Arg Pro Ala Pro Gly Ser Thr Ala Pro Pro Ala His Gly
1               5                   10                  15

Val Thr Ser Ala Pro Asp Thr Arg Pro Ala Pro Gly Ser Thr Ala Pro
                20                  25                  30

Pro Ala His Gly Val Thr Ser Ala His His His His His His
            35                  40                  45

<210> SEQ ID NO 6
<211> LENGTH: 33
<212> TYPE: PRT
<213> ORGANISM: Artificial Sequence
<220> FEATURE:
<223> OTHER INFORMATION: Truncated Receptor (TR)
```

```
<400> SEQUENCE: 6

Gly Thr Ile Asn Val His Asp Val Glu Thr Gln Phe Asn Gln Tyr Lys
1               5                   10                  15

Thr Glu Ala Ala Ser Pro Tyr Asn Leu Thr Ile Ser Asp Val Ser Val
            20                  25                  30

Ser

<210> SEQ ID NO 7
<211> LENGTH: 45
<212> TYPE: PRT
<213> ORGANISM: Artificial Sequence
<220> FEATURE:
<223> OTHER INFORMATION: Primary Sequence of the MUC1 Growth Factor
      Receptor (PSMGFR)

<400> SEQUENCE: 7

Gly Thr Ile Asn Val His Asp Val Glu Thr Gln Phe Asn Gln Tyr Lys
1               5                   10                  15

Thr Glu Ala Ala Ser Pro Tyr Asn Leu Thr Ile Ser Asp Val Ser Val
            20                  25                  30

Ser Asp Val Pro Phe Pro Phe Ser Ala Gln Ser Gly Ala
        35                  40                  45

<210> SEQ ID NO 8
<211> LENGTH: 25
<212> TYPE: PRT
<213> ORGANISM: Artificial Sequence
<220> FEATURE:
<223> OTHER INFORMATION: Primary Sequence of the Interchain Binding
      Region) (PSIBR)

<400> SEQUENCE: 8

Gly Phe Leu Gly Leu Ser Asn Ile Lys Phe Arg Pro Gly Ser Val Val
1               5                   10                  15

Val Gln Leu Thr Leu Ala Phe Arg Glu
            20                  25

<210> SEQ ID NO 9
<211> LENGTH: 40
<212> TYPE: PRT
<213> ORGANISM: Artificial Sequence
<220> FEATURE:
<223> OTHER INFORMATION: Repeat Motif 2 (RM2)

<400> SEQUENCE: 9

Pro Asp Thr Arg Pro Ala Pro Gly Ser Thr Ala Pro Pro Ala His Gly
1               5                   10                  15

Val Thr Ser Ala Pro Asp Thr Arg Pro Ala Pro Gly Ser Thr Ala Pro
            20                  25                  30

Pro Ala His Gly Val Thr Ser Ala
        35                  40

<210> SEQ ID NO 10
<211> LENGTH: 1255
<212> TYPE: PRT
<213> ORGANISM: Artificial Sequence
<220> FEATURE:
<223> OTHER INFORMATION: Mucin 1 Precursor, Genbank Accession Number:
      P15941

<400> SEQUENCE: 10

Met Thr Pro Gly Thr Gln Ser Pro Phe Phe Leu Leu Leu Leu Leu Thr
1               5                   10                  15
```

```
Val Leu Thr Val Val Thr Gly Ser Gly His Ala Ser Ser Thr Pro Gly
         20                  25                  30

Gly Glu Lys Glu Thr Ser Ala Thr Gln Arg Ser Ser Val Pro Ser Ser
         35                  40                  45

Thr Glu Lys Asn Ala Val Ser Met Thr Ser Ser Val Leu Ser Ser His
     50                  55                  60

Ser Pro Gly Ser Gly Ser Ser Thr Thr Gln Gly Gln Asp Val Thr Leu
 65                  70                  75                  80

Ala Pro Ala Thr Glu Pro Ala Ser Gly Ser Ala Ala Thr Trp Gly Gln
                 85                  90                  95

Asp Val Thr Ser Val Pro Val Thr Arg Pro Ala Leu Gly Ser Thr Thr
                100                 105                 110

Pro Pro Ala His Asp Val Thr Ser Ala Pro Asp Asn Lys Pro Ala Pro
                115                 120                 125

Gly Ser Thr Ala Pro Pro Ala His Gly Val Thr Ser Ala Pro Asp Thr
130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
                180                 185                 190

Pro Pro Ala His Gly Val Thr Ser Ala Pro Asp Thr Arg Pro Ala Pro
                195                 200                 205

Gly Ser Thr Ala Pro Pro Ala His Gly Val Thr Ser Ala Pro Asp Thr
210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
                260                 265                 270

Pro Pro Ala His Gly Val Thr Ser Ala Pro Asp Thr Arg Pro Ala Pro
                275                 280                 285

Gly Ser Thr Ala Pro Pro Ala His Gly Val Thr Ser Ala Pro Asp Thr
                290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Thr Arg Pro Ala Pro Gly Ser Thr Ala
                340                 345                 350

Pro Pro Ala His Gly Val Thr Ser Ala Pro Asp Thr Arg Pro Ala Pro
                355                 360                 365

Gly Ser Thr Ala Pro Pro Ala His Gly Val Thr Ser Ala Pro Asp Thr
                370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
                405                 410                 415

Gly Val Thr Ser Ala Pro Asp Thr Arg Pro Ala Pro Gly Ser Thr Ala
                420                 425                 430

Pro Pro Ala His Gly Val Thr Ser Ala Pro Asp Thr Arg Pro Ala Pro
```

```
                435                 440                 445
Gly Ser Thr Ala Pro Pro Ala His Gly Val Thr Ser Ala Pro Asp Thr
    450                 455                 460

Arg Pro Ala Pro Gly Ser Thr Ala Pro Pro Ala His Gly Val Thr Ser
465                 470                 475                 480

Ala Pro Asp Thr Arg Pro Ala Pro Gly Ser Thr Ala Pro Pro Ala His
                485                 490                 495

Gly Val Thr Ser Ala Pro Asp Thr Arg Pro Ala Pro Gly Ser Thr Ala
            500                 505                 510

Pro Pro Ala His Gly Val Thr Ser Ala Pro Asp Thr Arg Pro Ala Pro
        515                 520                 525

Gly Ser Thr Ala Pro Pro Ala His Gly Val Thr Ser Ala Pro Asp Thr
    530                 535                 540

Arg Pro Ala Pro Gly Ser Thr Ala Pro Pro Ala His Gly Val Thr Ser
545                 550                 555                 560

Ala Pro Asp Thr Arg Pro Ala Pro Gly Ser Thr Ala Pro Pro Ala His
                565                 570                 575

Gly Val Thr Ser Ala Pro Asp Thr Arg Pro Ala Pro Gly Ser Thr Ala
            580                 585                 590

Pro Pro Ala His Gly Val Thr Ser Ala Pro Asp Thr Arg Pro Ala Pro
        595                 600                 605

Gly Ser Thr Ala Pro Pro Ala His Gly Val Thr Ser Ala Pro Asp Thr
    610                 615                 620

Arg Pro Ala Pro Gly Ser Thr Ala Pro Pro Ala His Gly Val Thr Ser
625                 630                 635                 640

Ala Pro Asp Thr Arg Pro Ala Pro Gly Ser Thr Ala Pro Pro Ala His
                645                 650                 655

Gly Val Thr Ser Ala Pro Asp Thr Arg Pro Ala Pro Gly Ser Thr Ala
            660                 665                 670

Pro Pro Ala His Gly Val Thr Ser Ala Pro Asp Thr Arg Pro Ala Pro
        675                 680                 685

Gly Ser Thr Ala Pro Pro Ala His Gly Val Thr Ser Ala Pro Asp Thr
    690                 695                 700

Arg Pro Ala Pro Gly Ser Thr Ala Pro Pro Ala His Gly Val Thr Ser
705                 710                 715                 720

Ala Pro Asp Thr Arg Pro Ala Pro Gly Ser Thr Ala Pro Pro Ala His
                725                 730                 735

Gly Val Thr Ser Ala Pro Asp Thr Arg Pro Ala Pro Gly Ser Thr Ala
            740                 745                 750

Pro Pro Ala His Gly Val Thr Ser Ala Pro Asp Thr Arg Pro Ala Pro
        755                 760                 765

Gly Ser Thr Ala Pro Pro Ala His Gly Val Thr Ser Ala Pro Asp Thr
    770                 775                 780

Arg Pro Ala Pro Gly Ser Thr Ala Pro Pro Ala His Gly Val Thr Ser
785                 790                 795                 800

Ala Pro Asp Thr Arg Pro Ala Pro Gly Ser Thr Ala Pro Pro Ala His
                805                 810                 815

Gly Val Thr Ser Ala Pro Asp Thr Arg Pro Ala Pro Gly Ser Thr Ala
            820                 825                 830

Pro Pro Ala His Gly Val Thr Ser Ala Pro Asp Thr Arg Pro Ala Pro
        835                 840                 845

Gly Ser Thr Ala Pro Pro Ala His Gly Val Thr Ser Ala Pro Asp Thr
    850                 855                 860
```

Arg Pro Ala Pro Gly Ser Thr Ala Pro Ala His Gly Val Thr Ser
865                 870                 875                 880

Ala Pro Asp Thr Arg Pro Ala Pro Gly Ser Thr Ala Pro Pro His
            885                 890                 895

Gly Val Thr Ser Ala Pro Asp Thr Arg Pro Ala Pro Gly Ser Thr Ala
        900                 905                 910

Pro Pro Ala His Gly Val Thr Ser Ala Pro Asp Thr Arg Pro Ala Pro
            915                 920                 925

Gly Ser Thr Ala Pro Pro Ala His Gly Val Thr Ser Ala Pro Asp Asn
930                 935                 940

Arg Pro Ala Leu Gly Ser Thr Ala Pro Val His Asn Val Thr Ser
945                 950                 955                 960

Ala Ser Gly Ser Ala Ser Gly Ser Ala Ser Thr Leu Val His Asn Gly
            965                 970                 975

Thr Ser Ala Arg Ala Thr Thr Thr Pro Ala Ser Lys Ser Thr Pro Phe
            980                 985                 990

Ser Ile Pro Ser His His Ser Asp Thr Pro Thr Thr Leu Ala Ser His
            995                 1000                1005

Ser Thr Lys Thr Asp Ala Ser Ser Thr His His Ser Ser Val Pro
1010                1015                1020

Pro Leu Thr Ser Ser Asn His Ser Thr Ser Pro Gln Leu Ser Thr
1025                1030                1035

Gly Val Ser Phe Phe Phe Leu Ser Phe His Ile Ser Asn Leu Gln
1040                1045                1050

Phe Asn Ser Ser Leu Glu Asp Pro Ser Thr Asp Tyr Tyr Gln Glu
1055                1060                1065

Leu Gln Arg Asp Ile Ser Glu Met Phe Leu Gln Ile Tyr Lys Gln
1070                1075                1080

Gly Gly Phe Leu Gly Leu Ser Asn Ile Lys Phe Arg Pro Gly Ser
1085                1090                1095

Val Val Val Gln Leu Thr Leu Ala Phe Arg Glu Gly Thr Ile Asn
1100                1105                1110

Val His Asp Val Glu Thr Gln Phe Asn Gln Tyr Lys Thr Glu Ala
1115                1120                1125

Ala Ser Arg Tyr Asn Leu Thr Ile Ser Asp Val Ser Val Ser Asp
1130                1135                1140

Val Pro Phe Pro Phe Ser Ala Gln Ser Gly Ala Gly Val Pro Gly
1145                1150                1155

Trp Gly Ile Ala Leu Leu Val Leu Val Cys Val Leu Val Ala Leu
1160                1165                1170

Ala Ile Val Tyr Leu Ile Ala Leu Ala Val Cys Gln Cys Arg Arg
1175                1180                1185

Lys Asn Tyr Gly Gln Leu Asp Ile Phe Pro Ala Arg Asp Thr Tyr
1190                1195                1200

His Pro Met Ser Glu Tyr Pro Thr Tyr His Thr His Gly Arg Tyr
1205                1210                1215

Val Pro Pro Ser Ser Thr Asp Arg Ser Pro Tyr Glu Lys Val Ser
1220                1225                1230

Ala Gly Asn Gly Gly Ser Ser Leu Ser Tyr Thr Asn Pro Ala Val
1235                1240                1245

Ala Ala Ala Ser Ala Asn Leu
1250                1255

<210> SEQ ID NO 11

<211> LENGTH: 302
<212> TYPE: PRT
<213> ORGANISM: Artificial Sequence
<220> FEATURE:
<223> OTHER INFORMATION: Proopiomelanocortin
(adrenocorticotropin/beta-lipotropin/alpha-mela- nocyte
stimulating hormone/beta-melanocyte stimulating
hormone/beta-endorphin) [Homo sapiens]. Accession number:

<400> SEQUENCE: 11

```
Ala Ala Ala Lys Glu Gly Lys Lys Ser Arg Asp Arg Glu Arg Pro Pro
 1               5                  10                  15
Ser Val Pro Ala Leu Arg Glu Gln Pro Pro Glu Thr Glu Pro Gln Pro
            20                  25                  30
Ala Trp Lys Met Pro Arg Ser Cys Cys Ser Arg Ser Gly Ala Leu Leu
        35                  40                  45
Leu Ala Leu Leu Leu Gln Ala Ser Met Glu Val Arg Gly Trp Cys Leu
    50                  55                  60
Glu Ser Ser Gln Cys Gln Asp Leu Thr Thr Glu Ser Asn Leu Leu Glu
65                  70                  75                  80
Cys Ile Arg Ala Cys Lys Pro Asp Leu Ser Ala Glu Thr Pro Met Phe
                85                  90                  95
Pro Gly Asn Gly Asp Glu Gln Pro Leu Thr Glu Asn Pro Arg Lys Tyr
            100                 105                 110
Val Met Gly His Phe Arg Trp Asp Arg Phe Gly Arg Arg Asn Ser Ser
        115                 120                 125
Ser Ser Gly Ser Ser Gly Ala Gly Gln Lys Arg Glu Asp Val Ser Ala
    130                 135                 140
Gly Glu Asp Cys Gly Pro Leu Pro Glu Gly Gly Pro Glu Pro Arg Ser
145                 150                 155                 160
Asp Gly Ala Lys Pro Gly Pro Arg Glu Gly Lys Arg Ser Tyr Ser Met
                165                 170                 175
Glu His Phe Arg Trp Gly Lys Pro Val Gly Lys Lys Arg Arg Pro Val
            180                 185                 190
Lys Val Tyr Pro Asn Gly Ala Glu Asp Glu Ser Ala Glu Ala Phe Pro
        195                 200                 205
Leu Glu Phe Lys Arg Glu Leu Thr Gly Gln Arg Leu Arg Glu Gly Asp
    210                 215                 220
Gly Pro Asp Gly Pro Ala Asp Asp Gly Ala Gly Ala Gln Ala Asp Leu
225                 230                 235                 240
Glu His Ser Leu Leu Val Ala Leu Glu Lys Lys Asp Glu Gly Pro Tyr
                245                 250                 255
Arg Met Glu His Phe Arg Trp Gly Ser Pro Pro Lys Asp Lys Arg Tyr
            260                 265                 270
Gly Gly Phe Met Thr Ser Glu Lys Ser Gln Thr Pro Leu Val Thr Leu
        275                 280                 285
Phe Lys Asn Ala Ile Ile Lys Asn Ala Tyr Lys Lys Gly Glu
    290                 295                 300
```

<210> SEQ ID NO 12
<211> LENGTH: 31
<212> TYPE: PRT
<213> ORGANISM: Artificial Sequence
<220> FEATURE:
<223> OTHER INFORMATION: RGD

<400> SEQUENCE: 12

```
His His His His His His Ser Ser Ser Gly Ser Ser Ser Ser Gly
 1               5                  10                  15
```

```
Ser Ser Ser Ser Gly Gly Arg Gly Asp Ser Gly Arg Gly Asp Ser
            20                  25                  30

<210> SEQ ID NO 13
<211> LENGTH: 19
<212> TYPE: PRT
<213> ORGANISM: Artificial Sequence
<220> FEATURE:
<223> OTHER INFORMATION: Irrelevant peptide

<400> SEQUENCE: 13

His His His His His His Arg Gly Glu Phe Thr Gly Thr Tyr Ile Thr
1               5                   10                  15

Ala Val Thr

<210> SEQ ID NO 14
<211> LENGTH: 12
<212> TYPE: PRT
<213> ORGANISM: Artificial Sequence
<220> FEATURE:
<223> OTHER INFORMATION: Metastasis inhibition factor NM23

<400> SEQUENCE: 14

Thr Phe Ile Ala Ile Lys Pro Asp Gly Val Gln Arg
1               5                   10

<210> SEQ ID NO 15
<211> LENGTH: 18
<212> TYPE: PRT
<213> ORGANISM: Artificial Sequence
<220> FEATURE:
<223> OTHER INFORMATION: Metastasis inhibition factor NM23
<220> FEATURE:
<221> NAME/KEY: misc_feature
<222> LOCATION: (3)..(3)
<223> OTHER INFORMATION: Xaa can be any naturally occurring amino acid

<400> SEQUENCE: 15

Val Met Xaa Leu Gly Glu Thr Asn Pro Ala Asp Ser Lys Pro Gly Thr
1               5                   10                  15

Ile Arg

<210> SEQ ID NO 16
<211> LENGTH: 17
<212> TYPE: PRT
<213> ORGANISM: Artificial Sequence
<220> FEATURE:
<223> OTHER INFORMATION: Metastasis inhibition factor NM23

<400> SEQUENCE: 16

Val Met Leu Gly Glu Thr Asn Pro Ala Asp Ser Lys Pro Gly Thr Ile
1               5                   10                  15

Arg

<210> SEQ ID NO 17
<211> LENGTH: 10
<212> TYPE: PRT
<213> ORGANISM: Artificial Sequence
<220> FEATURE:
<223> OTHER INFORMATION: Metastasis inhibition factor NM23

<400> SEQUENCE: 17

Asn Ile Ile His Gly Ser Asp Ser Val Lys
1               5                   10
```

```
<210> SEQ ID NO 18
<211> LENGTH: 9
<212> TYPE: PRT
<213> ORGANISM: Artificial Sequence
<220> FEATURE:
<223> OTHER INFORMATION: Metastasis inhibition factor NM23

<400> SEQUENCE: 18

Gly Leu Val Gly Glu Ile Ile Lys Arg
1               5

<210> SEQ ID NO 19
<211> LENGTH: 8
<212> TYPE: PRT
<213> ORGANISM: Artificial Sequence
<220> FEATURE:
<223> OTHER INFORMATION: Metastasis inhibition factor NM23

<400> SEQUENCE: 19

Gly Leu Val Gly Glu Ile Ile Lys
1               5

<210> SEQ ID NO 20
<211> LENGTH: 12
<212> TYPE: PRT
<213> ORGANISM: Artificial Sequence
<220> FEATURE:
<223> OTHER INFORMATION: Metastasis inhibition factor NM23

<400> SEQUENCE: 20

Thr Phe Ile Ala Ile Lys Pro Asp Gly Val Gln Arg
1               5                   10

<210> SEQ ID NO 21
<211> LENGTH: 21
<212> TYPE: PRT
<213> ORGANISM: Artificial Sequence
<220> FEATURE:
<223> OTHER INFORMATION: Metastasis inhibition factor NM23
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 21

Tyr Met Xaa His Ser Gly Pro Val Val Ala Met Xaa Val Trp Glu Gly
1               5                   10                  15

Leu Asn Val Val Lys
            20

<210> SEQ ID NO 22
<211> LENGTH: 19
<212> TYPE: PRT
<213> ORGANISM: Artificial Sequence
<220> FEATURE:
<223> OTHER INFORMATION: 14-3-3 epsilon

<400> SEQUENCE: 22

Ala Ala Phe Asp Asp Ala Ile Ala Glu Leu Asp Thr Leu Ser Glu Glu
1               5                   10                  15

Ser Tyr Lys

<210> SEQ ID NO 23
<211> LENGTH: 18
```

```
<212> TYPE: PRT
<213> ORGANISM: Artificial Sequence
<220> FEATURE:
<223> OTHER INFORMATION: 14-3-3 epsilon
<220> FEATURE:
<221> NAME/KEY: misc_feature
<222> LOCATION: (8)..(8)
<223> OTHER INFORMATION: Xaa can be any naturally occurring amino acid

<400> SEQUENCE: 23

Ala Ala Ser Asp Ile Ala Met Xaa Thr Glu Leu Pro Pro Thr His Pro
1               5                   10                  15

Ile Arg

<210> SEQ ID NO 24
<211> LENGTH: 11
<212> TYPE: PRT
<213> ORGANISM: Artificial Sequence
<220> FEATURE:
<223> OTHER INFORMATION: 14-3-3 epsilon

<400> SEQUENCE: 24

Tyr Leu Ala Glu Phe Ala Thr Gly Asn Asp Arg
1               5                   10

<210> SEQ ID NO 25
<211> LENGTH: 10
<212> TYPE: PRT
<213> ORGANISM: Artificial Sequence
<220> FEATURE:
<223> OTHER INFORMATION: 14-3-3 epsilon

<400> SEQUENCE: 25

Asp Ser Thr Leu Ile Met Gln Leu Leu Arg
1               5                   10

<210> SEQ ID NO 26
<211> LENGTH: 9
<212> TYPE: PRT
<213> ORGANISM: Artificial Sequence
<220> FEATURE:
<223> OTHER INFORMATION: 14-3-3 epsilon

<400> SEQUENCE: 26

Tyr Asp Glu Met Val Glu Ser Met Lys
1               5

<210> SEQ ID NO 27
<211> LENGTH: 14
<212> TYPE: PRT
<213> ORGANISM: Artificial Sequence
<220> FEATURE:
<223> OTHER INFORMATION: 14-3-3 epsilon
<220> FEATURE:
<221> NAME/KEY: misc_feature
<222> LOCATION: (5)..(5)
<223> OTHER INFORMATION: Xaa can be any naturally occurring amino acid

<400> SEQUENCE: 27

Val Ala Gly Met Xaa Asp Val Glu Leu Thr Val Glu Glu Arg
1               5                   10

<210> SEQ ID NO 28
<211> LENGTH: 12
<212> TYPE: PRT
<213> ORGANISM: Artificial Sequence
<220> FEATURE:
<223> OTHER INFORMATION: 14-3-3 epsilon
```

-continued

```
<400> SEQUENCE: 28

His Leu Ile Pro Ala Ala Asn Thr Gly Glu Ser Lys
1               5                   10

<210> SEQ ID NO 29
<211> LENGTH: 19
<212> TYPE: PRT
<213> ORGANISM: Artificial Sequence
<220> FEATURE:
<223> OTHER INFORMATION: cathepsin D
<220> FEATURE:
<221> NAME/KEY: misc_feature
<222> LOCATION: (12)..(12)
<223> OTHER INFORMATION: Xaa can be any naturally occurring amino acid

<400> SEQUENCE: 29

Asp Pro Asp Ala Gln Pro Gly Gly Glu Leu Met Xaa Leu Gly Gly Thr
1               5                   10                  15

Asp Ser Lys

<210> SEQ ID NO 30
<211> LENGTH: 18
<212> TYPE: PRT
<213> ORGANISM: Artificial Sequence
<220> FEATURE:
<223> OTHER INFORMATION: cathepsin D

<400> SEQUENCE: 30

Asp Pro Asp Ala Gln Pro Gly Gly Glu Leu Met Leu Gly Gly Thr Asp
1               5                   10                  15

Ser Lys

<210> SEQ ID NO 31
<211> LENGTH: 18
<212> TYPE: PRT
<213> ORGANISM: Artificial Sequence
<220> FEATURE:
<223> OTHER INFORMATION: cathepsin D
<220> FEATURE:
<221> NAME/KEY: misc_feature
<222> LOCATION: (15)..(15)
<223> OTHER INFORMATION: Xaa can be any naturally occurring amino acid

<400> SEQUENCE: 31

Ile Ser Val Asn Asn Val Leu Pro Val Phe Asp Asn Leu Met Xaa Gln
1               5                   10                  15

Gln Lys

<210> SEQ ID NO 32
<211> LENGTH: 17
<212> TYPE: PRT
<213> ORGANISM: Artificial Sequence
<220> FEATURE:
<223> OTHER INFORMATION: cathepsin D

<400> SEQUENCE: 32

Ile Ser Val Asn Asn Val Leu Pro Val Phe Asp Asn Leu Met Gln Gln
1               5                   10                  15

Lys

<210> SEQ ID NO 33
<211> LENGTH: 10
<212> TYPE: PRT
<213> ORGANISM: Artificial Sequence
<220> FEATURE:
<223> OTHER INFORMATION: cathepsin D
```

```
<400> SEQUENCE: 33

Gln Pro Gly Ile Thr Phe Ile Ala Ala Lys
1               5                   10

<210> SEQ ID NO 34
<211> LENGTH: 16
<212> TYPE: PRT
<213> ORGANISM: Artificial Sequence
<220> FEATURE:
<223> OTHER INFORMATION: human annexin V with Proline substitution by
      Thrionine

<400> SEQUENCE: 34

Gly Leu Gly Thr Asp Glu Glu Ser Ile Leu Thr Leu Leu Thr Ser Arg
1               5                   10                  15

<210> SEQ ID NO 35
<211> LENGTH: 13
<212> TYPE: PRT
<213> ORGANISM: Artificial Sequence
<220> FEATURE:
<223> OTHER INFORMATION: human annexin V with Proline substituion by
      Thrionine

<400> SEQUENCE: 35

Asp Leu Leu Asp Asp Leu Lys Ser Glu Leu Thr Gly Lys
1               5                   10

<210> SEQ ID NO 36
<211> LENGTH: 9
<212> TYPE: PRT
<213> ORGANISM: Artificial Sequence
<220> FEATURE:
<223> OTHER INFORMATION: human annexin V with Proline substituion by
      Thrionine

<400> SEQUENCE: 36

Ser Glu Ile Asp Leu Phe Asn Ile Arg
1               5
```